United States Patent
Tanabe et al.

(10) Patent No.: US 9,920,050 B2
(45) Date of Patent: Mar. 20, 2018

(54) FUSED HETEROCYCLIC COMPOUND AND PEST CONTROL USE THEREOF

(71) Applicant: Sumitomo Chemical Company, Limited, Tokyo (JP)

(72) Inventors: Takamasa Tanabe, Takarazuka (JP); Hajime Mizuno, Takarazuka (JP); Ayaka Tanaka, Takarazuka (JP); Shinya Nishimura, Takarazuka (JP); Yoshihiko Nokura, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 128 days.

(21) Appl. No.: 14/901,926

(22) PCT Filed: Jun. 25, 2014

(86) PCT No.: PCT/JP2014/067603
§ 371 (c)(1),
(2) Date: Dec. 29, 2015

(87) PCT Pub. No.: WO2015/002211
PCT Pub. Date: Jan. 8, 2015

(65) Prior Publication Data
US 2016/0368915 A1 Dec. 22, 2016

(30) Foreign Application Priority Data
Jul. 1, 2013 (JP) .................. 2013-137783

(51) Int. Cl.
*C07D 471/04* (2006.01)
*A01N 47/40* (2006.01)
(Continued)

(52) U.S. Cl.
CPC ........... *C07D 471/04* (2013.01); *A01N 43/52* (2013.01); *A01N 43/76* (2013.01); *A01N 43/78* (2013.01);
(Continued)

(58) Field of Classification Search
CPC .. C07D 471/04; C07D 413/04; C07D 413/14; C07D 471/14; A01N 47/40; A01N 43/52;
(Continued)

(56) References Cited

U.S. PATENT DOCUMENTS 9,549,559 B2 * 1/2017 Shimizu .................. A01N 43/90
2003/0114311 A1 6/2003 Balko et al.
(Continued)

FOREIGN PATENT DOCUMENTS

| JP | 2005505523 A | 2/2005 |
|----|----|----|
| WO | 0202540 A1 | 1/2002 |
| WO | 2013018928 A1 | 2/2013 |

OTHER PUBLICATIONS

Dua, R., "Pharmacological significance of synthetic heterocycles scaffold: a review." Advances in Biological Research 5.3 (2011): 120-144.*

(Continued)

*Primary Examiner* — John M Mauro
(74) *Attorney, Agent, or Firm* — Panitch Schwarze Belisario & Nadel LLP

(57) ABSTRACT

A fused heterocyclic compound is provided represented by the following formula (1) or an N-oxide thereof, wherein $A^1$ represents $NR^5$, oxygen or sulfur, $A^2$ and $A^3$ represent a nitrogen atom or the like, $R^1$ represents a C1 to C6 chain hydrocarbon group or the like, $R^2$ represents a C1 to C6 chain hydrocarbon group or the like, $R^3$ and $R^4$ are the same or different and represent a C1 to C6 chain hydrocarbon group or the like, n represents 0, 1 or 2, and G represents any of the following formulae, wherein Q represents an oxygen or sulfur atom, p represents 0 or 1, and $R^{10}$ to $R^{24}$ are the same or different and represent a C1 to C6 chain hydrocarbon group or the like. The compound has an excellent control effect on pests.

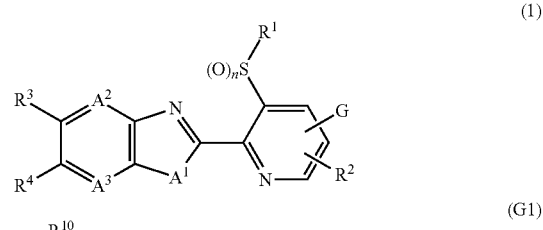

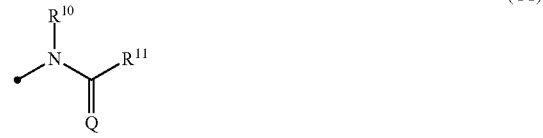

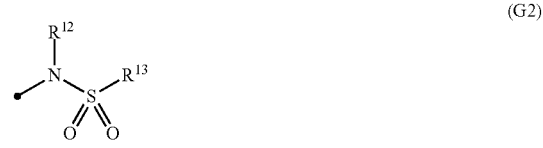

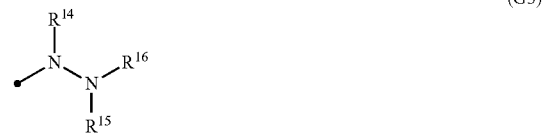

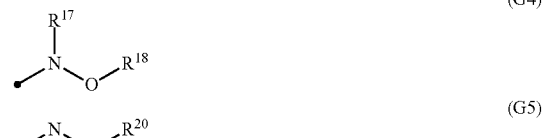

(Continued)

-continued

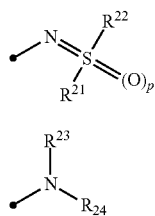

20 Claims, No Drawings

(51) Int. Cl.
| | | |
|---|---|---|
| A01N 43/52 | (2006.01) | |
| A01N 47/20 | (2006.01) | |
| C07D 413/04 | (2006.01) | |
| C07D 413/14 | (2006.01) | |
| C07D 471/14 | (2006.01) | |
| A01N 47/18 | (2006.01) | |
| A01N 43/90 | (2006.01) | |
| A01N 43/78 | (2006.01) | |
| A01N 43/76 | (2006.01) | |
| A01N 47/36 | (2006.01) | |

(52) U.S. Cl.
CPC ............. *A01N 43/90* (2013.01); *A01N 47/18* (2013.01); *A01N 47/20* (2013.01); *A01N 47/36* (2013.01); *A01N 47/40* (2013.01); *C07D 413/04* (2013.01); *C07D 413/14* (2013.01); *C07D 471/14* (2013.01)

(58) Field of Classification Search
CPC ........ A01N 47/20; A01N 47/18; A01N 43/90; A01N 43/78; A01N 43/76; A01N 47/36
See application file for complete search history.

(56) References Cited

U.S. PATENT DOCUMENTS

| | | |
|---|---|---|
| 2004/0014977 A1 | 1/2004 | Fukuda et al. |
| 2005/0233909 A1 | 10/2005 | Fukuda et al. |
| 2014/0194290 A1 | 7/2014 | Takahashi et al. |

OTHER PUBLICATIONS

International Search Report dated Aug. 26, 2014 in International Application No. PCT/JP2014/067603.

\* cited by examiner

FUSED HETEROCYCLIC COMPOUND AND PEST CONTROL USE THEREOF

CROSS-REFERENCE TO RELATED APPLICATION

This application is a Section 371 of International Application No. PCT/JP2014/067603, filed Jun. 25, 2014, which was published in the Japanese language on Jan. 8, 2015, under International Publication No. WO 2015/002211 A1, and the disclosure of which is incorporated herein by reference.

TECHNICAL FIELD

The present invention relates to a certain type of a fused heterocyclic compound and a use thereof for pest control.

BACKGROUND ART

So far, for the purpose of pest control, various compounds have been studied and put to practical use. In addition, a certain type of a fused heterocyclic compound (for example, see Patent Document 1) is known.

PRIOR ART DOCUMENT

Patent Document

Patent Document 1: WO2013/018928

SUMMARY OF THE INVENTION

Problems to be Solved by the Invention

An object of the present invention is to provide a compound having an excellent control effect on pests and a method for controlling pests using the compound.

Means for Solving the Problems

As a result of an intensive study to solve the above problem, the present inventors have found that a fused heterocyclic compound represented by the following formula (1) has an excellent control effect on pests, and thereby reaching the present invention.

More specifically, the present invention is as described below.

[1] A fused heterocyclic compound represented by formula (1):

$$\text{(1)}$$

wherein
$A^1$ represents $NR^5$, an oxygen atom, or a sulfur atom,
$A^2$ represents a nitrogen atom or $CR^6$,
$A^3$ represents a nitrogen atom or $CR^7$,
$R^1$ represents a C1 to C6 chain hydrocarbon group optionally having one or more atoms or groups selected from group U or a C3 to C9 alicyclic hydrocarbon group optionally having one or more atoms or groups selected from group V,
$R^2$ represents a C1 to C6 chain hydrocarbon group optionally having one or more atoms or groups selected from group U, a phenyl group optionally having one or more atoms or groups selected from group W, a 5- or 6-membered heterocyclic group optionally having one or more atoms or groups selected from group W, $OR^8$, $S(O)_mR^8$, $S(O)_2NR^8R^9$, $NR^8R^9$, $NR^8CO_2R^9$, $NR^8C(O)R^9$, $CO_2R^8$, $C(O)R^8$, $C(O)NR^8R^9$, $SF_5$, a cyano group, a nitro group, a halogen atom, or a hydrogen atom, G represents a group represented by group G1, group G2, group G3, group G4, group G5, group G6 or group G7 of the following formulae:

$$\text{(G1)}$$
$$\text{(G2)}$$
$$\text{(G3)}$$
$$\text{(G4)}$$
$$\text{(G5)}$$
$$\text{(G6)}$$
$$\text{(G7)}$$

wherein
Q represents an oxygen atom or a sulfur atom,
p represents 0 or 1,
$R^{10}$ represents a C1 to C6 chain hydrocarbon group optionally having one or more atoms or groups selected from group U, a phenyl group optionally having one or more atoms or groups selected from group W, a hydrogen atom, a C1 to C6 chain hydrocarbon group having one or more atoms or groups selected from group Z, a C3 to C9 alicyclic hydrocarbon group optionally having one or more atoms or groups selected from group V, a 4-, 5- or 6-membered heterocyclic group optionally having one or more atoms or groups selected from group W, $CO_2R^8$, $C(O)R^8$, or $C(O)NR^8R^9$,
$R^{11}$ represents $R^{25}$, $R^{26}$, $OR^{27}$, $OR^{28}$, $SR^{29}$, $NR^{30}R^{31}$ or $C(O)R^{32}$, wherein $R^{25}$ represents a C1 to C6 chain hydrocarbon group having one or more atoms or groups selected from group Z, a C3 to C9 alicyclic hydrocarbon group optionally having one or more atoms or groups selected from group V, or a 4-, 5- or 6-membered heterocyclic group optionally having one or more atoms or groups selected from group W; $R^{26}$ represents a C1 to C6 chain hydrocarbon group optionally having one or more atoms or groups selected from group U, a phenyl group optionally having one or more atoms or groups selected from group W, or a hydrogen atom; $R^{27}$ represents a C1 to C6 chain hydrocarbon group having one or more atoms or groups selected from group Z, a C3 to C9 alicyclic hydrocarbon group optionally having one or more atoms or groups selected from group V, or a 4-, 5- or 6-membered heterocyclic group optionally having one or more atoms or groups selected from group W; $R^{28}$ represents a C1 to C6 chain hydrocarbon group optionally having one or more atoms or groups selected from group U, a phenyl group optionally having one or more atoms or groups selected from group W, or a hydrogen atom; $R^{29}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 5- or 6-membered heterocyclic group optionally having one or more atoms or groups selected from group W, or a hydrogen atom; $R^{30}$ and $R^{31}$ are the same or different and represent a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, $SO_2R^8$, $CO_2R^8$, $C(O)R^8$, or a hydrogen atom; and $R^{32}$ represents a C1 to C6 chain hydrocarbon group optionally having one or more atoms or groups selected from group Y, $OR^8$, $NR^8R^9$, or a hydrogen atom, when $R^{11}$ represents $R^{25}$, $OR^{27}$, $SR^{29}$, $NR^{30}R^{31}$, or $C(O)R^{32}$, $R^{10}$ represents a C1 to C6 chain hydrocarbon group optionally having one or more atoms or groups selected from group U, a phenyl group optionally having one or more atoms or groups selected from group W, a hydrogen atom, a C1 to C6 chain hydrocarbon group having one or more atoms or groups selected from group Z, a C3 to C9 alicyclic hydrocarbon group optionally having one or more atoms or groups selected from group V, a 4-, 5- or 6-membered heterocyclic group optionally having one or more atoms or groups selected from group W, $CO_2R^8$, $C(O)R^8$, or $C(O)NR^8R^9$, when $R^{11}$ represents $R^{26}$ or $OR^{28}$, $R^{10}$ represents a C1 to C6 chain hydrocarbon group having one or more atoms or groups selected from group Z, a C3 to C9 alicyclic hydrocarbon group optionally having one or more atoms or groups selected from group V, a 4-, 5- or 6-membered heterocyclic group optionally having one or more atoms or groups selected from group W, $CO_2R^8$, $C(O)R^8$, or $C(O)NR^8R^9$, $R^{12}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, a hydrogen atom, $SO_2R^8$, $CO_2R^8$, $C(O)R^8$, or $C(O)NR^8R^9$, $R^{13}$ represents $R^{33}$, wherein $R^{33}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, or a 4-, 5- or 6-membered heterocyclic group optionally having one or more atoms or groups selected from group W, $OR^{34}$, wherein $R^{34}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, or a hydrogen atom, or $NR^{35}R^{36}$, wherein $R^{35}$ and $R^{36}$ are the same or different and represent a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, or a hydrogen atom, $R^{14}$ and $R^{15}$ are the same or different and represent a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, a hydrogen atom, $SO_2R^8$, $CO_2R^8$, $C(O)R^8$, or $C(O)NR^8R^9$, $R^{16}$ represents $R^{37}$, wherein $R^{37}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, or a hydrogen atom, $C(O)R^{38}$, wherein $R^{38}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, or a hydrogen atom, $CO_2R^{39}$, wherein $R^{39}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, or a hydrogen atom, C(O)SR$^{40}$, wherein R$^{40}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, or a 4-, 5- or 6-membered heterocyclic group optionally having one or more atoms or groups selected from group W, C(O)NR$^{41}$R$^{42}$, wherein R$^{41}$ and R$^{42}$ are the same or different and represent a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, or a hydrogen atom, SO$_2$R$^{43}$, wherein R$^{43}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, or a 4-, 5- or 6-membered heterocyclic group optionally having one or more atoms or groups selected from group W, S(O)$_2$OR$^{44}$, wherein R$^{44}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, or a 4-, 5- or 6-membered heterocyclic group optionally having one or more atoms or groups selected from group W, or S(O)$_2$NR$^{45}$R$^{46}$, wherein R$^{45}$ and R$^{46}$ are the same or different and represent a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, or a hydrogen atom, R$^{17}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, a hydrogen atom, SO$_2$R$^8$, CO$_2$R$^8$, C(O)R$^8$, or C(O)NR$^8$R$^9$, R$^{18}$ represents R$^{47}$, wherein R$^{47}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, or a hydrogen atom, C(Q)R$^{48}$, wherein R$^{48}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, or a hydrogen atom, C(Q)OR$^{49}$, wherein R$^{49}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, or a hydrogen atom, or C(Q)NR$^{50}$R$^{51}$, wherein R$^{50}$ and R$^{51}$ are the same or different and represent a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, or a hydrogen atom, R$^{19}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 5- or 6-membered heterocyclic group optionally having one or more atoms or groups selected from group W, or a hydrogen atom, R$^{20}$ represents R$^{52}$, wherein R$^{52}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, or a hydrogen atom, OR$^{53}$, wherein R$^{53}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, or a 4-, 5- or 6-membered heterocyclic group optionally having one or more atoms or groups selected from group W, or NR$^{54}$R$^{55}$, wherein R$^{54}$ and R$^{55}$ are the same or different and represent a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, or a hydrogen atom, R$^{21}$ and R$^{22}$ are the same or different and represent a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, or a 4-, 5- or 6-membered heterocyclic group optionally having one or more atoms or groups selected from group W, R$^{23}$ represents a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, or a hydrogen atom, $R^{24}$ represents a C1 to C6 chain hydrocarbon group having one or more atoms or groups selected from group Z, a C3 to C9 alicyclic hydrocarbon group optionally having one or more atoms or groups selected from group V, or a 4-, 5- or 6-membered heterocyclic group optionally having one or more atoms or groups selected from group W, $R^3$ and $R^4$ are the same or different and represent a C1 to C6 chain hydrocarbon group optionally having one or more atoms or groups selected from group U, a phenyl group optionally having one or more atoms or groups selected from group W, a 5- or 6-membered heterocyclic group optionally having one or more atoms or groups selected from group W, $OR^8$, $S(O)_m R^8$, $SO_2 NR^8 R^9$, $NR^8 R^9$, $NR^8 CO_2 R^9$, $NR^8 C(O)R^9$, $CO_2 R^8$, $C(O)R^8$, $C(O)NR^8 R^9$, $SF_5$, a cyano group, a nitro group, a halogen atom, or a hydrogen atom, or $R^3$ and $R^4$, together with the carbon atoms to which they are attached, form a benzene ring optionally having one or more atoms or groups selected from group W, a 5- or 6-membered heterocyclic ring optionally having one or more atoms or groups selected from group W, or a 5-, 6-, 7- or 8-membered nonaromatic ring optionally having one or more atoms or groups selected from group V, $R^5$ represents a C1 to C6 chain hydrocarbon group optionally having one or more atoms or groups selected from group X, a C1 to C6 chain hydrocarbon group having a phenyl group, wherein the phenyl group optionally has one or more atoms or groups selected from group W, a C1 to C6 chain hydrocarbon group having a 5- or 6-membered heterocyclic group, wherein the 5- or 6-membered heterocyclic group optionally has one or more atoms or groups selected from group W, $CO_2 R^8$, $C(O)R^8$, a C3 to C9 alicyclic hydrocarbon group optionally having one or more atoms or groups selected from group V, or a hydrogen atom, $R^6$ and $R^7$ are the same or different and represent a C1 to C6 chain hydrocarbon group optionally having one or more halogen atoms, $OR^8$, $S(O)_m R^8$, $NR^8 R^9$, $CO_2 R^8$, $C(O)R^8$, a cyano group, a nitro group, a halogen atom, or a hydrogen atom, $R^8$ and $R^9$ are the same or different and represent a C1 to C6 chain hydrocarbon group optionally having one or more atoms or groups selected from group Y, a C3 to C9 alicyclic hydrocarbon group optionally having one or more atoms or groups selected from group V, a phenyl group optionally having one or more atoms or groups selected from group W, a 4-, 5- or 6-membered heterocyclic group optionally having one or more atoms or groups selected from group W, or a hydrogen atom, and m each independently represents 0, 1, or 2, and n represents 0, 1, or 2, wherein when m is 1 or 2 in $S(O)_m R^8$, $R^8$ does not represent a hydrogen atom;

Group U: a group consisting of C1 to C6 alkoxy groups optionally having one or more halogen atoms, C2 to C6 alkenyloxy groups optionally having one or more halogen atoms, C2 to C6 alkynyloxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C3 to C9 cycloalkyl groups optionally having one or more halogen atoms or one or more C1 to C3 alkyl groups, cyano groups, hydroxy groups, and halogen atoms, Group V: a group consisting of C1 to C6 chain hydrocarbon groups optionally having one or more halogen atoms, C1 to C6 alkoxy groups optionally having one or more halogen atoms, C2 to C6 alkenyloxy groups optionally having one or more halogen atoms, C2 to C6 alkynyloxy groups optionally having one or more halogen atoms, and halogen atoms, Group W: a group consisting of C1 to C6 chain hydrocarbon groups optionally having one or more halogen atoms, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C1 to C6 alkylamino groups optionally having one or more halogen atoms, C2 to C8 dialkylamino groups optionally having one or more halogen atoms, C2 to C6 alkylcarbonyl groups optionally having one or more halogen atoms, C2 to C6 alkoxycarbonyl groups optionally having one or more halogen atoms, halogen atoms, cyano groups, and nitro groups, Group X: a group consisting of C3 to C9 cycloalkyl groups optionally having one or more halogen atoms, C1 to C6 alkoxy groups optionally having one or more halogen atoms, C2 to C6 alkenyloxy groups optionally having one or more halogen atoms, C2 to C6 alkynyloxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, hydroxy groups, halogen atoms, and cyano groups, Group Y: a group consisting of C3 to C9 alicyclic hydrocarbon groups optionally having one or more atoms or groups selected from group V, C1 to C6 alkoxy groups optionally having one or more halogen atoms, C2 to C6 alkenyloxy groups optionally having one or more halogen atoms, C2 to C6 alkynyloxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C1 to C6 alkylaminosulfonyl groups optionally having one or more halogen atoms, C2 to C8 dialkylaminosulfonyl groups optionally having one or more halogen atoms, C1 to C6 alkylamino groups optionally having one or more halogen atoms, C2 to C8 dialkylamino groups optionally having one or more halogen atoms, C2 to C6 alkylcarbonylamino groups optionally having one or more halogen atoms, C2 to C6 alkoxycarbonylamino groups optionally having one or more halogen atoms, C2 to C6 alkylcarbonyl groups optionally having one or more halogen atoms, C2 to C6 alkoxycarbonyl groups optionally having one or more halogen atoms, C2 to C6 alkylaminocarbonyl groups optionally having one or more halogen atoms, C3 to C10 dialkylaminocarbonyl groups optionally having one or more halogen atoms, cyano groups, hydroxy groups, and halogen atoms, Group Z: a group consisting of phenyl groups optionally having one or more atoms or groups selected from group W, 4-, 5- or 6-membered heterocyclic groups optionally having one or more atoms or groups selected from group W, C1 to C6 alkylamino groups optionally having one or more halogen atoms, C2 to C8 dialkylamino groups optionally having one or more halogen atoms, C2 to C6 alkylcarbonylamino groups optionally having one or more halogen atoms, C2 to C6 alkoxycarbonylamino groups optionally having one or more halogen atoms, C2 to C6 alkylaminocarbonyl groups optionally having one or more halogen atoms, and C3 to C10 dialkylaminocarbonyl groups optionally having one or more halogen atoms, or an N-oxide thereof (hereinafter, the fused heterocyclic compound represented by the formula (1) and the N-oxide thereof are referred to as the compound of the present invention).

[2] The compound according to [1], wherein $R^1$ is a C1 to C6 alkyl group optionally having one or more atoms or groups selected from the group consisting of halogen atoms and cyclopropyl groups, wherein the cyclopropyl group optionally has one or more halogen atoms or one or more C1 to C3 alkyl groups, a C2 to C6 alkenyl group optionally having one or more halogen atoms, a C2 to C6 alkynyl group optionally having one or more halogen atoms, or a C3 to C6 cycloalkyl group optionally having one or more atoms or groups selected from the group consisting of halogen atoms and C1 to C6 alkyl groups optionally having one or more halogen atoms, $R^2$ is a halogen atom or a hydrogen atom, $R^3$ and $R^4$ are the same or different and are a C1 to C6 chain hydrocarbon group optionally having one or more atoms or groups selected from group U, $OR^8$, $S(O)_m R^8$, a halogen atom, or a hydrogen atom, and $R^5$ is a C1 to C6 chain hydrocarbon group optionally having one or more atoms or groups selected from group X, $CO_2R^8$, $C(O)R^8$, a C3 to C9 alicyclic hydrocarbon group optionally having one or more atoms or groups selected from group V, or a hydrogen atom.

[3] The compound according to [1] or [2], wherein $A^1$ is $NR^5$.

[4] The compound according to [1] or [2], wherein $A^1$ is an oxygen atom.

[5] The compound according to [1] or [2], wherein $A^1$ is a sulfur atom.

[6] The compound according to any one of [1] to [5], wherein $A^2$ is $CR^6$, and $A^3$ is a nitrogen atom.

[7] The compound according to any one of [1] to [5], wherein $A^2$ is $CR^6$, and $A^3$ is $CR^7$.

[8] The compound according to any one of [1] to [7], wherein G is group G1.

[9] The compound according to any one of [1] to [7], wherein G is group G2.

[10] The compound according to any one of [1] to [7], wherein G is group G3.

[11] The compound according to any one of [1] to [7], wherein G is group G4.

[12] The compound according to any one of [1] to [7], wherein G is group G5.

[13] The compound according to any one of [1] to [7], wherein G is group G6.

[14] The compound according to any one of [1] to [7], wherein G is group G7.

[15] The compound according to any one of [1] to [7], wherein G is group G1, and
$R^{11}$ is $R^{25}$, $OR^{27}$, $SR^{29}$, $NR^{30}R^{31}$, or $C(O)R^{32}$.

[16] The compound according to any one of [1] to [7], wherein G is group G1, and
$R^{11}$ is $R^{26}$ or $OR^{28}$.

[17] A compound represented by formula (1A),

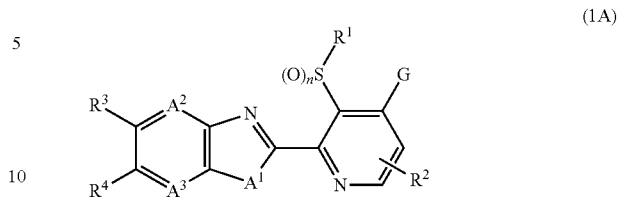

wherein symbols represent the same meaning as in the formula (1).

[18] A compound represented by formula (1B),

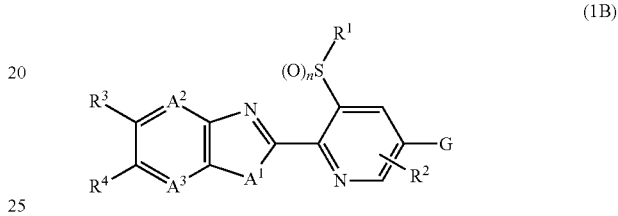

wherein symbols represent the same meaning as in the formula (1).

[19] A compound represented by formula (1C),

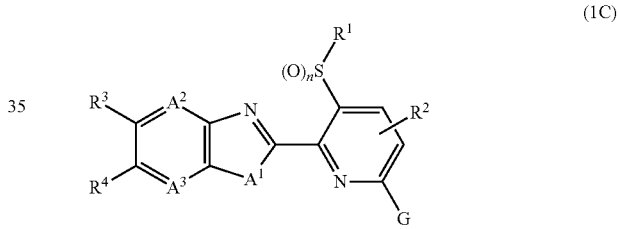

wherein symbols represent the same meaning as in the formula (1).

[20] A pest controlling agent which comprises the compound as defined in any one of [1] to [19], and an inert carrier.

[21] A method for controlling pests comprising applying an effective amount of the compound as defined in any one of [1] to [19] to a pest or a pest-infested area.

MODE FOR CARRYING OUT THE INVENTION

The groups used in the description of the present specification will be described below with examples.

The "halogen atom" in this invention refers to a fluorine atom, a chlorine atom, a bromine atom, and an iodine atom. The "C1 to C6 chain hydrocarbon group" in this invention represents a C1 to C6 alkyl group, a C2 to C6 alkenyl group, and a C2 to C6 alkynyl group.

Examples of the "C1 to C6 alkyl group" in this invention include C1 to C6 alkyl groups such as a methyl group, an ethyl group, a propyl group, an isopropyl group, a butyl group, an isobutyl group, a sec-butyl group, a tert-butyl group, a pentyl group, a neopentyl group, a hexyl group, and the like. Examples of the "C2 to C6 alkenyl group" in this invention include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, and the like.

Examples of the "C2 to C6 alkynyl group" in this invention include an ethynyl group, a propargyl group, a 2-butynyl group, a 3-butynyl group, a 1-pentynyl group, a 1-hexynyl group, and the like.

The notation of the "C1 to C6 chain hydrocarbon group optionally having one or more atoms or groups selected from group U" in this invention represents a straight-chain or branched-chain hydrocarbon group comprising a carbon atom number of 1 to 6, in which a hydrogen atom bound to the carbon atom is optionally substituted by an atom or group selected from group U, and at that time, when having two or more atoms or groups selected from group U, the atoms or groups selected from group U may be the same or different from each other. Examples of the "C1 to C6 chain hydrocarbon group optionally having one or more atoms or groups selected from group U" include C1 to C6 alkyl groups optionally having one or more atoms or groups selected from group U such as a methyl group, an ethyl group, a propyl group, an isopropyl group, a butyl group, an isobutyl group, a sec-butyl group, a tert-butyl group, a pentyl group, a neopentyl group, a hexyl group, a methoxymethyl group, an ethoxymethyl group, a propyloxymethyl group, an isopropyloxymethyl group, a butyloxymethyl group, a sec-butyloxymethyl group, a tert-butyloxymethyl group, a 2-methoxyethyl group, a 2-ethoxyethyl group, a 2-propyloxyethyl group, a 2-isopropyloxyethyl group, a 2-butyloxyethyl group, a 2-sec-butyloxyethyl group, a 2-tert-butyloxyethyl group, a trifluoromethyl group, a trichloromethyl group, a 2-fluoroethyl group, a 2,2-difluoroethyl group, a 2,2,2,-trifluoroethyl group, a pentafluoroethyl group, a 2-(methylsulfanyl)ethyl group, a 2-(ethylsulfanyl)ethyl group, a 2-(methylsulfinyl)ethyl group, a 2-(methylsulfonyl)ethyl group, a 2-hydroxyethyl group, a cyclopropylmethyl group, a 1-methylcyclopropylmethyl group, and a 2,2-difluorocyclopropylmethyl group;

C2 to C6 alkenyl groups optionally having one or more atoms or groups selected from group U such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group; and C2 to C6 alkynyl groups optionally having one or more atoms or groups selected from group U such as an ethynyl group, a propargyl group, a 2-butynyl group, a 3-butynyl group, a 1-pentynyl group, a 1-hexynyl group, and a 4,4,4-trifluoro-2-butynyl group.

The notation of the "C1 to C6 chain hydrocarbon group optionally having one or more atoms or groups selected from group X" in this invention represents a straight-chain or branched-chain hydrocarbon group comprising a carbon atom number of 1 to 6, in which a hydrogen atom bound to the carbon atom is optionally substituted by an atom or group selected from group X, and at that time, when having two or more atoms or groups selected from group X, the atoms or groups selected from group X may be the same or different from each other.

Examples of the "C1 to C6 chain hydrocarbon group optionally having one or more atoms or groups selected from group X" include C1 to C6 alkyl groups optionally having one or more atoms or groups selected from group X such as a methyl group, an ethyl group, a propyl group, an isopropyl group, a butyl group, an isobutyl group, a sec-butyl group, a tert-butyl group, a pentyl group, a neopentyl group, a hexyl group, a methoxymethyl group, an ethoxymethyl group, a propyloxymethyl group, an isopropyloxymethyl group, a butyloxymethyl group, a sec-butyloxymethyl group, a tert-butyloxymethyl group, a 2-methoxyethyl group, a 2-ethoxyethyl group, a 2-propyloxyethyl group, a 2-isopropyloxyethyl group, a 2-butyloxyethyl group, a 2-sec-butyloxyethyl group, a 2-tert-butyloxyethyl group, a trifluoromethyl group, a trichloromethyl group, a 2-fluoroethyl group, a 2,2-difluoroethyl group, a 2,2,2,-trifluoroethyl group, a pentafluoroethyl group, a 2-(methylsulfanyl)ethyl group, a 2-(ethylsulfanyl)ethyl group, a 2-(methylsulfinyl)ethyl group, a 2-(methylsulfonylethyl) group, a 2-hydroxyethyl group, a cyclopropylmethyl group, a 1-methylcyclopropylmethyl group, a 2,2-difluorocyclopropylmethyl group, a phenylmethyl group, a 4-chlorophenylmethyl group, a 4-trifluoromethylphenylmethyl group, a tetrahydrofuran-2-ylmethyl group, a tetrahydropyran-2-ylmethyl group, a tetrahydropyran-3-ylmethyl group, a thiazol-5-ylmethyl group, a 2-chlorothiazol-5-ylmethyl group, a pyridin-3-ylmethyl group, a 6-chloropyridin-3-ylmethyl group, and a 6-trifluoromethylpyridin-3-ylmethyl group;

C2 to C6 alkenyl groups optionally having one or more atoms or groups selected from group X such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group; and C2 to C6 alkynyl groups optionally having one or more atoms or groups selected from group X such as an ethynyl group, a propargyl group, a 2-butynyl group, a 3-butynyl group, a 1-pentynyl group, a 1-hexynyl group, and a 4,4,4-trifluoro-2-butynyl group.

The notation of the "C1 to C6 chain hydrocarbon group optionally having one or more atoms or groups selected from group Y" in this invention represents a straight-chain or branched-chain hydrocarbon group comprising a carbon atom number of 1 to 6, in which a hydrogen atom bound to the carbon atom is optionally substituted by an atom or group selected from group Y, and at that time, when having two or more atoms or groups selected from group Y, the atoms or groups selected from group Y may be the same or different from each other. Examples of the "C1 to C6 chain hydrocarbon group optionally having one or more atoms or groups selected from group Y" include C1 to C6 alkyl groups optionally having one or more atoms or groups selected from group Y such as a methyl group, an ethyl group, a propyl group, an isopropyl group, a butyl group, an isobutyl group, a sec-butyl group, a tert-butyl group, a pentyl group, a neopentyl group, a hexyl group, a methoxymethyl group, an ethoxymethyl group, a propyloxymethyl group, an isopropyloxymethyl group, a butyloxymethyl group, a sec-butyloxymethyl group, a tert-butyloxymethyl group, a 2-methoxyethyl group, a 2-ethoxyethyl group, a 2-propyloxyethyl group, a 2-isopropyloxyethyl group, a 2-butyloxyethyl group, a 2-sec-butyloxyethyl group, a 2-tert-butyloxyethyl group, a trifluoromethyl group, a trichloromethyl group, a 2-fluoroethyl group, a 2,2-difluoroethyl group, a 2,2,2,-trifluoroethyl group, a pentafluoroethyl group, a 2-(methylsulfanyl)ethyl group, a 2-(ethylsulfanyl)ethyl group, a 2-(methylsulfinyl)ethyl group, a 2-(methylsulfonylethyl) group, a 2-hydroxyethyl group, a cyclopropylmethyl group, a 1-methylcyclopropylmethyl group, a 2,2-difluorocyclopropylmethyl group, a phenylmethyl group, a 4-chlorophenylmethyl group, a 4-trifluoromethylphenylmethyl group, a tetrahydrofuran-2-ylmethyl group, a tetrahydropyran-2-ylmethyl group, a tetrahydropyran-3-ylmethyl group, a thiazol-5-ylmethyl group, a 2-chlorothiazol-5-ylmethyl group, a pyridin-3-ylmethyl group, a 6-chloropyridin-3-ylmethyl group and a 6-trifluoromethylpyridin-3-ylmethyl group;
C2 to C6 alkenyl groups optionally having one or more atoms or groups selected from group 0 such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group; and
C2 to C6 alkynyl groups optionally having one or more atoms or groups selected from group Y such as an ethynyl group, a propargyl group, a 2-butynyl group, a 3-butynyl group, a 1-pentynyl group, a 1-hexynyl group, and a 4,4,4-trifluoro-2-butynyl group.

The notation of the "C1 to C6 chain hydrocarbon group optionally having one or more atoms or groups selected from group Z" in this invention represents a straight-chain or branched-chain hydrocarbon group comprising a carbon atom number of 1 to 6, in which a hydrogen atom bound to the carbon atom is optionally substituted by an atom or group selected from group Z, and at that time, when having two or more atoms or groups selected from group Z, the atoms or groups selected from group Z may be the same or different from each other. Examples of the "C1 to C6 chain hydrocarbon group optionally having one or more atoms or groups selected from group Z" include C1 to C6 alkyl groups optionally having one or more atoms or groups selected from group Z such as a methyl group, an ethyl group, a propyl group, an isopropyl group, a butyl group, an isobutyl group, a sec-butyl group, a tert-butyl group, a pentyl group, a neopentyl group, a hexyl group, a cyclopropylmethyl group, a 1-methylcyclopropylmethyl group, a 2,2-difluorocyclopropylmethyl group, a phenylmethyl group, a 4-chlorophenylmethyl group, a 4-trifluoromethylphenylmethyl group, a tetrahydrofuran-2-ylmethyl group, a tetrahydropyran-2-ylmethyl group, a tetrahydropyran-3-ylmethyl group, a thiazol-5-ylmethyl group, a 2-chlorothiazol-5-ylmethyl group, a pyridin-3-ylmethyl group, a 6-chloropyridin-3-ylmethyl group, a 6-trifluoromethylpyridin-3-ylmethyl group, a 2-(methylamino)ethyl group, a 2-(dimethylamino)ethyl group, a 2-(acetylaminocarbonyl)ethyl group, a 2-(methoxycarbonylamino)ethyl group, a 2-(methylaminocarbonyl)ethyl group, and a 2-(dimethylaminocarbonyl)ethyl group;
C2 to C6 alkenyl groups optionally having one or more atoms or groups selected from group Z such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 2-cyclopropylvinyl group, a 2-phenylvinyl group, a 3-phenyl-2-propenyl group, a 2-(pyridin-3-yl)vinyl group, and a 3-(dimethylamino)-2-propenyl group; and
C2 to C6 alkynyl groups optionally having one or more atoms or groups selected from group Z such as an ethynyl group, a propargyl group, a 2-butynyl group, a 3-butynyl group, a 1-pentynyl group, a 1-hexynyl group, a 2-phenylethynyl group, and a 2-(pyridin-3-yl)ethynyl group.

Examples of the "C1 to C6 chain hydrocarbon group optionally having one or more halogen atoms" in this invention include C1 to C6 alkyl groups optionally having one or more halogen atoms such as a methyl group, an ethyl group, a propyl group, an isopropyl group, a butyl group, an isobutyl group, a sec-butyl group, a tert-butyl group, a pentyl group, a neopentyl group, a hexyl group, a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group;
C2 to C6 alkenyl groups optionally having one or more halogen atoms such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group; and
C2 to C6 alkynyl groups optionally having one or more halogen atoms such as an ethynyl group, a propargyl group, a 2-butynyl group, a 3-butynyl group, a 1-pentynyl group, a 1-hexynyl group and a 4,4,4-trifluoro-2-butynyl group.

Examples of the "C1 to C6 alkyl group optionally having one or more atoms or groups selected from the group consisting of halogen atoms and cyclopropyl groups, wherein the cyclopropyl group optionally has one or more halogen atoms or one or more C1 to C3 alkyl groups" in this invention include a methyl group, an ethyl group, a propyl group, an isopropyl group, a butyl group, an isobutyl group, a sec-butyl group, a tert-butyl group, a pentyl group, a neopentyl group, a hexyl group, a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2,-trifluoroethyl group, a pentafluoroethyl group, a heptafluoropropyl group, a heptafluoroisopropyl group, a cyclopropylmethyl group, a 2-cyclopropylethyl group, a 1-cyclopropylethyl group, and the like.

Examples of the "C1 to C6 alkyl group optionally having one or more halogen atoms" in this invention include a methyl group, an ethyl group, a propyl group, an isopropyl group, a butyl group, an isobutyl group, a sec-butyl group, a tert-butyl group, a pentyl group, a neopentyl group, a hexyl group, a fluoromethyl group, a chloromethyl group, a bromomethyl group, an iodomethyl group, a difluoromethyl group, a dichloromethyl group, a trifluoromethyl group, a bromodifluoromethyl group, a chlorodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, a heptafluoroisopropyl group, and the like.

Examples of the "C1 to C6 chain hydrocarbon group having one phenyl group, wherein the phenyl group may have one or more atoms or groups selected from group W" in this invention include a phenylmethyl group, a 4-chlorophenylmethyl group, a 4-trifluoromethylphenylmethyl group, and the like. At that time, when having two or more atoms or groups selected from group W, the atoms or groups selected from group W may be the same or different from each other.

Examples of the "C1 to C6 chain hydrocarbon group having one 5- or 6-membered heterocyclic group, wherein the 5- or 6-membered heterocyclic group may have one or more atoms or groups selected from group W" in this invention include a tetrahydrofuran-2-ylmethyl group, a tetrahydropyran-2-ylmethyl group and a tetrahydropyran-3-ylmethyl group, a thiozol-5-ylmethyl group, a 2-chlorothiozol-5-ylmethyl group, a pyridin-3-ylmethyl group, a 6-chloropyridin-3-ylmethyl group, a 6-trifluoromethylpyridin-3-ylmethyl group, and the like. At that time, when having two or more atoms or groups selected from group W, the atoms or groups selected from group W may be the same or different from each other. Examples of the "C2 to C6 alkenyl group optionally having one or more halogen atoms" in this invention include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, a pentafluoroallyl group, and the like.

Examples of the "C2 to C6 alkynyl group optionally having one or more halogen atoms" in this invention include an ethynyl group, a propargyl group, a 2-butynyl group, a 3-butynyl group, a 1-pentynyl group, a 1-hexynyl group, a 4,4,4-trifluoro-2-butynyl group, and the like.

The notation of the "C3 to C9 alicyclic hydrocarbon group optionally having one or more atoms or groups selected from group V" in this invention represents a cyclic nonaromatic hydrocarbon group comprising a carbon atom number of 3 to 9, in which a hydrogen atom bound to the carbon atom is optionally substituted by an atom or group selected from group V, and at that time, when having two or more atoms or groups selected from group V, the atoms or groups selected from group V may be the same or different from each other. Examples of the "C3 to C9 alicyclic hydrocarbon group optionally having one or more atoms or groups selected from group V" include a cyclopropyl group, a cyclobutyl group, a cyclopentyl group, a cyclohexyl group, a cycloheptyl group, a cyclooctyl group, a cyclononanyl group, a 1-cyclohexenyl group, a 2-cyclohexenyl group, a 3-cyclohexenyl group, a 1-methylcyclohexyl group, a 2-methylcyclohexyl group, a 3-methylcyclohexyl group, a 4-methylcyclohexyl group, a 2-methoxycyclohexyl group, a 3-methoxycyclohexyl group, a 4-methoxylcyclohexyl group, a 1-fluorocyclohexyl group, a 2-fluorocyclohexyl group, a 3-fluorocyclohexyl group, and a 4-fluorocyclohexyl group.

Examples of the "C3 to C6 cycloalkyl group" in this invention include a cyclopropyl group, a cyclobutyl group, a cyclopentyl group, and a cyclohexyl group.

Examples of the "C3 to C6 cycloalkyl group optionally having one or more atoms or groups selected from the group consisting of halogen atoms and C1 to C6 alkyl groups optionally having one or more halogen atoms" in this invention include a cyclopropyl group, a 1-methylcyclopropyl group, a 2-methylcyclopropyl group, a 1-fluorocyclopropyl group, a 2,2-difluorocyclopropyl group, a 2,2-dichlorocyclopropyl group, a 2,2-dibromocyclopropyl group, a cyclobutyl group, a cyclopentyl group, and a cyclohexyl group.

Examples of the "C3 to C9 cycloalkyl groups optionally having one or more halogen atoms" in this invention include a cyclopropyl group, a 1-fluorocyclopropyl group, a 2,2-difluorocyclopropyl group, a 2,2-dichlorocyclopropyl group, a 2,2-dibromocyclopropyl group, a cyclobutyl group, a cyclopentyl group, and a cyclohexyl group.

Examples of the "C3 to C9 cycloalkyl groups optionally having one or more halogen atoms or one or more C1 to C3 alkyl groups" in this invention include a cyclopropyl group, a 1-methylcyclopropyl group, a 2-dimethylcyclopropyl group, a 1-fluorocyclopropyl group, a 2,2-difluorocyclopropyl group, a 2, 2-dichlorocyclopropyl group, a 2, 2-dibromocyclopropyl group, a cyclobutyl group, a cyclopentyl group, and a cyclohexyl group. The notation of the "phenyl group optionally having one or more atoms or groups selected from group W" in this invention represents a phenyl group in which a hydrogen atom of the phenyl group is optionally substituted by an atom or group selected from group W, and at that time, when having two or more atoms or groups selected from group W, the atoms or groups selected from group W may be the same or different from each other. Examples of the "phenyl group optionally having one or more atoms or groups selected from group W" include a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethylphenyl group, a 3-trifluoromethylphenyl group, a 4-trifluoromethylphenyl group, a 2-trifluoromethoxyphenyl group, a 3-trifluoromethoxyphenyl group, a 4-trifluoromethoxyphenyl group, a 2-trifluoromethylsulfanylphenyl group, a 3-trifluoromethylsulfanylphenyl group, a 4-trifluoromethylsulfanylphenyl group, a 4-methoxycarbonylphenyl group, a 4-nitrophenyl group, a 4-cyanophenyl group, a 4-methylaminophenyl group, a 4-dimethylaminophenyl group, a 4-methylsulfinylphenyl group, a 4-methylsulfonylphenyl group, a 4-acetylphenyl group, and a 4-methoxycarbonylphenyl group.

The "heterocyclic group" in this invention represents a heterocyclic compound residue containing one or more nitrogen atoms, oxygen atoms or sulfur atoms, other than carbon atoms, as ring-constituting atoms, in the ring structure. Examples of the "heterocyclic group" include 5-membered nonaromatic heterocyclic heterocyclic groups such as a pyrrolidine ring, a tetrahydrofuran ring and a tetrahydrothiophene ring, 5-membered aromatic heterocyclic heterocyclic groups such as a pyrrole ring, a pyrazole ring, an imidazole ring, a furan ring, a thiophene ring, an oxazole ring and a thiazole ring, 6-membered nonaromatic heterocyclic heterocyclic groups such as a piperidine ring, a tetrahydropyran ring, a tetrahydrothiopyran ring, a piperazine ring and a morpholine group, and 6-membered aromatic heterocyclic heterocyclic groups such as a pyridine ring, a pyrimidine ring, a pyridazine ring and a pyrazine ring.

In addition, in this invention, the 5-membered heterocyclic group refers to a 5-membered nonaromatic heterocyclic group and a 5-membered aromatic heterocyclic group, and the 6-membered heterocyclic group refers to a 6-membered nonaromatic heterocyclic group and a 6-membered aromatic heterocyclic group. Examples of the "5- or 6-membered heterocyclic group optionally having one or more atoms or groups selected from group W" in this invention include 5- or 6-membered nonaromatic heterocyclic groups optionally having one or more atoms or groups selected from group W such as a pyrrolidin-1-yl group, a 3,3,4,4-tetrafluoropyrrolidin-1-yl group, a tetrahydrofuran-2-yl group, piperidyl groups, morpholyl groups, and thiomorpholyl groups; and 5- or 6-membered aromatic heterocyclic groups optionally having one or more atoms or groups selected from group W such as a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 2-methylsulfanyl-1-pyrrolyl group, a 2-methylsulfinyl-1-pyrrolyl group, a 2-methylsulfonyl-1-pyrrolyl group, a 2-methylamino-1-pyrrolyl group, a 2-dimethylamino-1-pyrrolyl group, a 5-bromo-2-furyl group, a 5-nitro-2-furyl group, a 5-cyano-2-furyl group, a 5-methoxy-2-furyl group, a 5-acetyl-2-furyl group, a 5-methoxycarbonyl-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazol-1-yl group, a 1,2,4-triazol-1-yl group, a 3-chloro-1,2,4-triazol-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a pyrazinyl group, a 4-pyrimidinyl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group, a 5-trifluoromethylpyridin-2-yl group, and a 5-trifluoromethoxypyridin-2-yl group.

Examples of the "4-, 5- or 6-membered heterocyclic group optionally having one or more atoms or groups selected from group W" in this invention include 4-, 5- or 6-membered nonaromatic heterocyclic groups optionally having one or more atoms or groups selected from group W such as a thietan-3-yl group, a pyrrolidin-1-yl group, a 3,3,4,4-tetrafluoropyrrolidin-1-yl group, a tetrahydrofuran-2-yl group, piperidyl groups, morpholyl groups, and thiomorpholyl groups; and 5- or 6-membered aromatic heterocyclic groups optionally having one or more atoms or groups selected from group W such as a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 2-methylsulfanyl-1-pyrrolyl group, a 2-methylsulfinyl-1-pyrrolyl group, a 2-methylsulfonyl-1-pyrrolyl group, a 2-methylamino-1-pyrrolyl group, a 2-dimethylamino-1-pyrrolyl group, a 5-bromo-2-furyl group, a 5-nitro-2-furyl group, a 5-cyano-2-furyl group, a 5-methoxy-2-furyl group, a 5-acetyl-2-furyl group, a 5-methoxycarbonyl-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazol-1-yl group, a 1,2,4-triazol-1-yl group, a 3-chloro-1,2,4-triazol-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a pyrazinyl group, a 4-pyrimidinyl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group, a 5-trifluoromethylpyridin-2-yl group, and a 5-trifluoromethoxypyridin-2-yl group.

Examples of the "C1 to C6 alkoxy groups optionally having one or more halogen atoms" in this invention include a methoxy group, a trifluoromethoxy group, an ethoxy group, a 2,2,2-trifluoroethoxy group, a propyloxy group, an isopropyloxy group, a butyloxy group, an isobutyloxy group, a sec-butyloxy group, a tert-butyloxy group, a pentyloxy group, and a hexyloxy group.

Examples of the "C1 to C6 alkylsulfanyl groups optionally having one or more halogen atoms" in this invention include a methylsulfanyl group, an ethylsulfanyl group, a propylsulfanyl group, an isopropylsulfanyl group, a butylsulfanyl group, a pentylsulfanyl group, a hexylsulfanyl group, a trifluoromethylsulfanyl group, a 2,2,2-trifluoroethylsulfanyl group, and a pentafluoroethylsulfanyl group.

Examples of the "C1 to C6 alkylsulfanyl groups optionally having one or more halogen atoms" in this invention include a methylsulfinyl group, an ethylsulfinyl group, a propylsulfinyl group, an isopropylsulfinyl group, a butylsulfinyl group, a pentylsulfinyl group, a hexylsulfinyl group, a trifluoromethylsulfinyl group, a 2,2,2-trifluoroethylsulfinyl group, and a pentafluoroethylsulfinyl group.

Examples of the "C1 to C6 alkylsulfonyl groups optionally having one or more halogen atoms" in this invention include a methylsulfonyl group, an ethylsulfonyl group, a propylsulfonyl group, an isopropylsulfonyl group, a butylsulfonyl group, a pentylsulfonyl group, a hexylsulfonyl group, a trifluoromethylsulfonyl group, a 2,2,2-trifluoroethylsulfonyl group, and a pentafluoroethylsulfonyl group.

Examples of the "C2 to C6 alkylcarbonyl groups optionally having one or more halogen atoms" in this invention include an acetyl group, a propionyl group, a butyryl group, a pentanoyl group, a hexanoyl group, and a trifluoroacetyl group.

Examples of the "C2 to C6 alkoxycarbonyl groups optionally having one or more halogen atoms" in this invention include a methoxycarbonyl group, an ethoxycarbonyl group, a propyloxycarbonyl group, a butyloxycarbonyl group, a pentyloxycarbonyl group, a tert-butyloxycarbonyl group, and a 2,2,2-trifluoroethyloxycarbonyl group.

Examples of the "C1 to C6 alkylamino groups optionally having one or more halogen atoms" in this invention include a methylamino group, an ethylamino group, a 2,2,2-trifluoroethylamino group, a propylamino group, and an isopropylamino group.

Examples of the "C2 to C8 dialkylamino groups optionally having one or more halogen atoms" in this invention include a dimethylamino group, a diethylamino group, a bis(2,2,2-trifluoroethyl)amino group, and a dipropylamino group.

Examples of the "C2 to C6 alkenyloxy groups optionally having one or more halogen atoms" in this invention include a 2-propenyloxy group, a 2-methyl-2-propenyloxy group, a 2-butenyloxy group, a 3-butenyloxy group, a 2-pentenyloxy group, a 2-hexenyloxy group, a 3,3-difluoroallyloxy group, and a 3,3-dichloroallyloxy group.

Examples of the "C2 to C6 alkynyloxy groups optionally having one or more halogen atoms" in this invention include a propargyloxy group, a 2-butynyloxy group, a 3-butynyloxy group, a 2-pentynyloxy group, a 2-hexynyloxy group, and a 4,4,4-trifluoro-2-butynyloxy group.

Examples of the "C1 to C6 alkylaminosulfonyl groups optionally having one or more halogen atoms" in this invention include a methylaminosulfonyl group, an ethylaminosulfonyl group, a 2,2,2-trifluoroethylaminosulfonyl group, a propylaminosulfonyl group, and an isopropylaminosulfonyl group.

Examples of the "C2 to C8 dialkylaminosulfonyl groups optionally having one or more halogen atoms" in this invention include a dimethylaminosulfonyl group, a diethylaminosulfonyl group, a bis(2,2,2-trifluoroethyl)aminosulfonyl group, and a dipropylaminosulfonyl group.

Examples of the "C2 to C6 alkylcarbonylamino groups optionally having one or more halogen atoms" in this invention include an acetylamino group, a propionylamino group, a butyrylamino group, a pentanoylamino group, a hexanoylamino group, and a trifluoroacetylamino group.

Examples of the "C2 to C6 alkoxycarbonylamino groups optionally having one or more halogen atoms" in this invention include a methoxycarbonylamino group, an ethoxycarbonylamino group, a propyloxycarbonylamino group, a butyloxycarbonylamino group, a pentyloxycarbonylamino group, a tert-butyloxycarbonylamino group, and a 2,2,2-trifluoroethyloxycarbonylamino group.

Examples of the "C2 to C6 alkylaminocarbonyl groups optionally having one or more halogen atoms" in this invention include a methylaminocarbonyl group, an ethylaminocarbonyl group, a 2,2,2-trifluoroethylaminocarbonyl group, a propylaminocarbonyl group, and an isopropylaminocarbonyl group.

Examples of the "C3 to C10 dialkylaminocarbonyl groups optionally having one or more halogen atoms" in this invention include a dimethylaminocarbonyl group, a diethylaminocarbonyl group, a bis(2,2,2-trifluoroethyl)aminocarbonyl group, and a dipropylaminocarbonyl group.

Specific examples of the compound in which "R3 and R4, together with the carbon atoms to which they are attached, form a benzene ring optionally having one or more atoms or groups selected from group W, a 5- or 6-membered heterocyclic ring optionally having one or more atoms or groups selected from group W, or a 5-, 6-, 7- or 8-membered nonaromatic ring optionally having one or more atoms or groups selected from group V" include the following formulae (1K-1) to (1K-15):

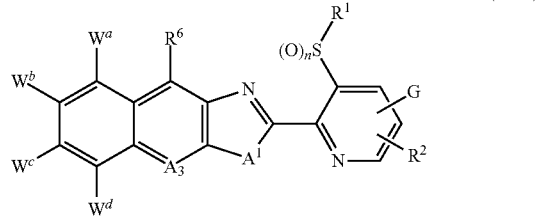

(1K-1)

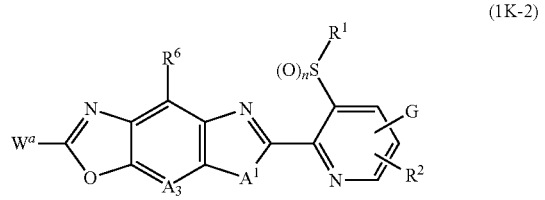

(1K-2)

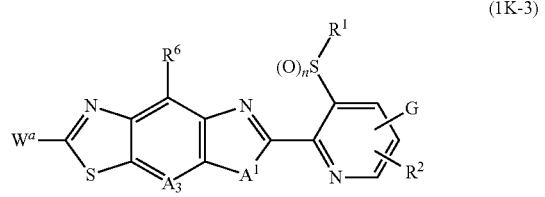

(1K-3)

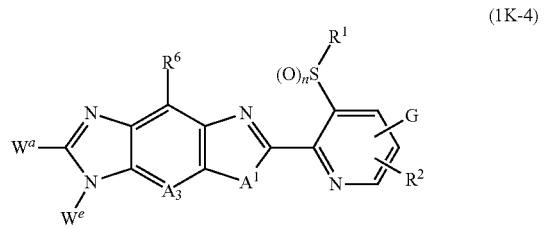

(1K-4)

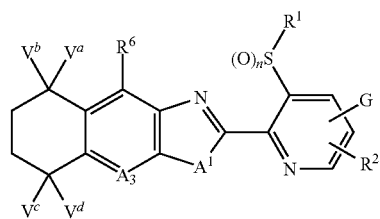

(1K-5)

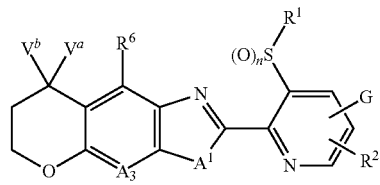

(1K-6)

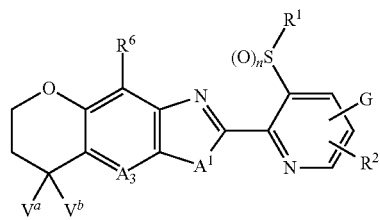

(1K-7)

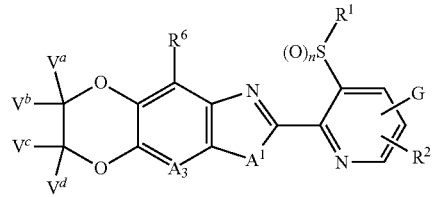

(1K-8)

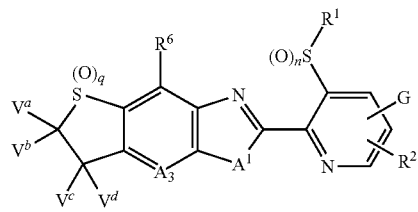

(1K-9)

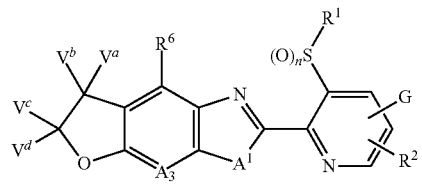

(1K-10)

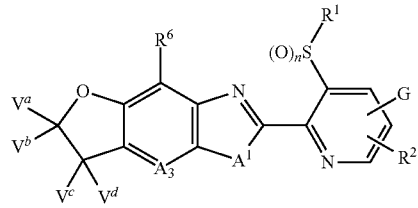

(1K-11)

-continued (1K-12)
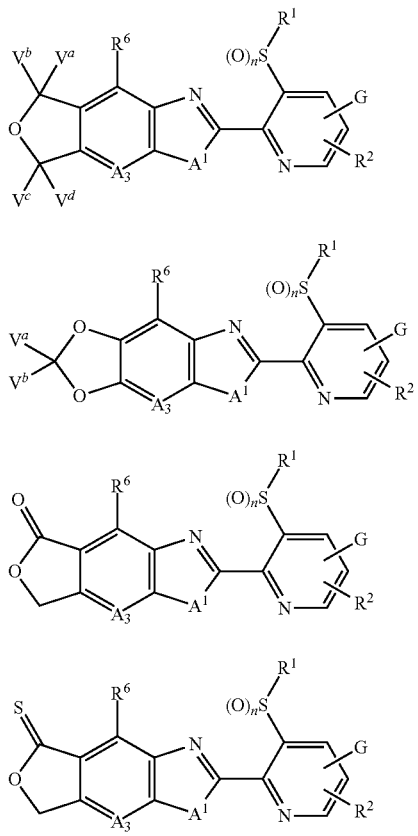

(1K-13)

(1K-14)

(1K-15)

wherein $W^a$, $W^b$, $W^c$ and $W^d$ are the same or different, and each represent a C1 to C6 chain hydrocarbon group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonyl group optionally having one or more halogen atoms, a C2 to C6 alkoxycarbonyl group optionally having one or more halogen atoms, a halogen atom, a cyano group, a nitro group, or a hydrogen atom, $W^e$ represents a C1 to C6 alkyl group optionally having one or more halogen atoms or a hydrogen atom, and $V^a$, $V^b$, $V^c$ and $V^d$ are the same or different, and each represent a C1 to C6 chain hydrocarbon group optionally having one or more halogen atoms, a C1 to C6 alkoxy group optionally having one or more halogen atoms, a C2 to C6 alkenyloxy group optionally having one or more halogen atoms, a C2 to C6 alkynyloxy group optionally having one or more halogen atoms, a halogen atom, or a hydrogen atom.

Specific examples of the groups G1 to G6 include groups (J1) to (J27) of the following formulae:

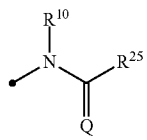
(J1)

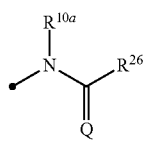
(J2)

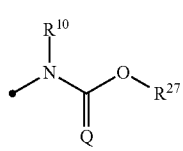
(J3)

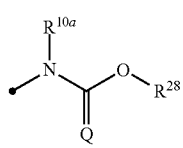
(J4)

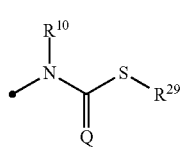
(J5)

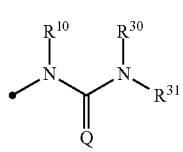
(J6)

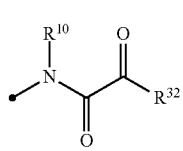
(J7)

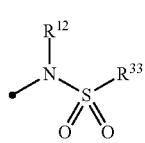
(J8)

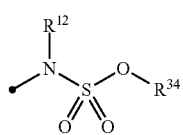
(J9)

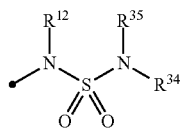
(J10)

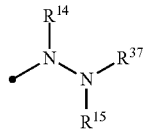
(J11)

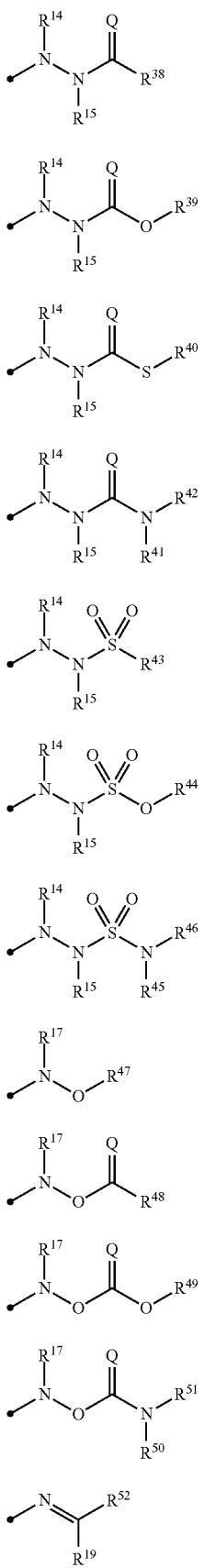

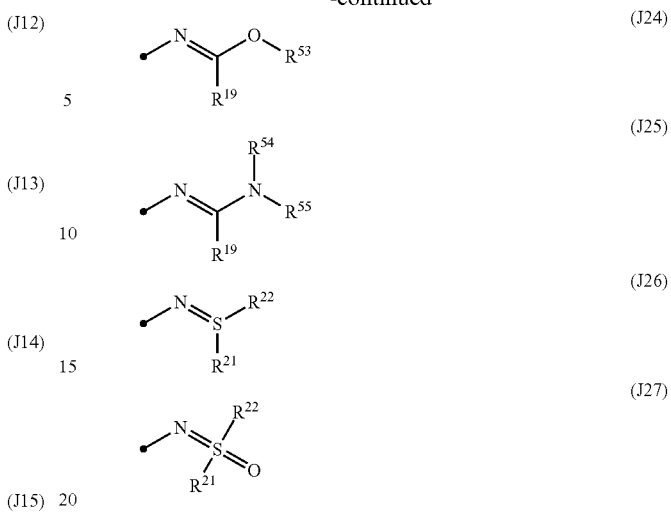

wherein
$R^{10a}$ represents a C1 to C6 chain hydrocarbon group optionally having one or more atoms or groups selected from group Z, a C3 to C9 alicyclic hydrocarbon group optionally having one or more atoms or groups selected from group V, a 4-, 5- or 6-membered heterocyclic group optionally having one or more atoms or groups selected from group W, $CO_2R^8$, $C(O)R^8$, or $C(O)NR^8R^9$; and other symbols represent the same meaning as in the formula (1).

The N-oxide in this invention is a compound in which the nitrogen atom constituting the ring on the heterocyclic group is oxidized. Examples of the heterocyclic group that may form an N-oxide include a pyridine ring. In the compound of the present invention, the N-oxide includes the compounds represented by the formulae (1N1) to (1N3) set forth below.

Examples of the compound of the present invention include the following compounds.
In the formula (1), compounds wherein $A^1$ is $NR^5$;
In the formula (1), compounds wherein $A^1$ is $NR^5$, and $R^7$ is a methyl group;
In the formula (1), compounds wherein $A^2$ is a sulfur atom;
In the formula (1), compounds wherein $A^2$ is an oxygen atom;
In the formula (1), compounds wherein $A^2$ is a nitrogen atom;
In the formula (1), compounds wherein $A^2$ is $CR^6$;
In the formula (1), compounds wherein $A^2$ is CH;
In the formula (1), compounds wherein $A^3$ is a nitrogen atom;
In the formula (1), compounds wherein $A^3$ is $CR^7$;
In the formula (1), compounds wherein $A^3$ is CH;
In the formula (1), compounds wherein $A^1$ is $NR^5$, $A^2$ is $CR^6$, and $A^3$ is a nitrogen atom;
In the formula (1), compounds wherein $A^1$ is $NR^5$, $A^2$ is $CR^6$, and $A^3$ is $CR^7$;
In the formula (1), compounds wherein $A^1$ is $NR^5$, $A^2$ is CH, and $A^3$ is a nitrogen atom;
In the formula (1), compounds wherein $A^1$ is $NR^5$, $A^2$ is CH, and $A^3$ is $CR^7$;
In the formula (1), compounds wherein $A^1$ is $NR^5$, $A^2$ is CH, and $A^3$ is CH;
In the formula (1), compounds wherein $A^1$ is $NR^5$, $R^5$ is a methyl group, $A^2$ is $CR^6$, and $A^3$ is a nitrogen atom;
In the formula (1), compounds wherein $A^1$ is $NR^5$, $R^5$ is a methyl group, $A^2$ is $CR^6$, and $A^3$ is $CR^7$;

In the formula (1), compounds wherein $A^1$ is $NR^5$, $R^5$ is a methyl group, $A^2$ is CH, and $A^3$ is a nitrogen atom;
In the formula (1), compounds wherein $A^1$ is $NR^5$, $R^5$ is a methyl group, $A^2$ is CH, and $A^3$ is $CR^7$;
In the formula (1), compounds wherein $A^1$ is $NR^5$, $R^5$ is a methyl group, $A^2$ is CH, and $A^3$ is CH;
In the formula (1), compounds wherein $A^1$ is a sulfur atom, $A^2$ is $CR^6$, and $A^3$ is a nitrogen atom;
In the formula (1), compounds wherein $A^1$ is a sulfur atom, A is $CR^6$, and $A^3$ is $CR^7$;
In the formula (1), compounds wherein $A^1$ is a sulfur atom, $A^2$ is CH, and $A^3$ is a nitrogen atom;
In the formula (1), compounds wherein $A^1$ is a sulfur atom, $A^2$ is CH, and $A^3$ is $CR^7$;
In the formula (1), compounds wherein $A^1$ is a sulfur atom, $A^2$ is CH, and $A^3$ is CH;
In the formula (1), compounds wherein $A^1$ is an oxygen atom, $A^2$ is $CR^6$, and $A^3$ is a nitrogen atom;
In the formula (1), compounds wherein $A^1$ is an oxygen atom, $A^2$ is CRC, and $A^3$ is $CR^7$;
In the formula (1), compounds wherein $A^1$ is an oxygen atom, $A^2$ is CH, and $A^3$ is a nitrogen atom;
In the formula (1), compounds wherein $A^1$ is an oxygen atom, $A^2$ is CH, and $A^3$ is $CR^7$;
In the formula (1), compounds wherein $A^1$ is an oxygen atom, A is CH, and $A^3$ is CH;
In the formula (1), compounds wherein $R^1$ is a C1 to C6 chain hydrocarbon group optionally having one or more atoms or groups selected from group U;
In the formula (1), compounds wherein $R^1$ is a C3 to C9 alicyclic hydrocarbon group optionally having one or more atoms or groups selected from group V;
In the formula (1), compounds wherein $R^1$ is a C1 to C6 alkyl group optionally having one or more atoms or groups selected from the group consisting of halogen atoms and cyclopropyl groups, wherein the cyclopropyl group optionally has one or more halogen atoms or one or more C1 to C3 alkyl groups;
In the formula (1), compounds wherein $R^1$ is a C1 to C6 chain hydrocarbon group optionally having one or more halogen atoms;
In the formula (1), compounds wherein $R^1$ is a C1 to C6 alkyl group optionally having one or more halogen atoms;
In the formula (1), compounds wherein $R^1$ is a C3 to C6 cycloalkyl group optionally having one or more atoms or groups selected from the group consisting of halogen atoms and C1 to C6 alkyl groups optionally having one or more halogen atoms;
In the formula (1), compounds wherein $R^1$ is a C1 to C6 alkyl group optionally having one or more atoms or groups selected from the group consisting of halogen atoms and cyclopropyl groups, wherein the cyclopropyl group optionally has one or more halogen atoms or one or more C1 to C3 alkyl groups, a C2 to C6 alkenyl group optionally having one or more halogen atoms, a C2 to C6 alkynyl group optionally having one or more halogen atoms, or a C3 to C6 cycloalkyl group optionally having one or more atoms or groups selected from the group consisting of halogen atoms and C1 to C6 alkyl groups optionally having one or more halogen atoms;
In the formula (1), compounds wherein $R^1$ is a methyl group, an ethyl group, a propyl group, a trifluoromethyl group, a 2,2,2-trifluoroethyl group, a cyclopropylmethyl group, or a cyclopropyl group;
In the formula (1), compounds wherein $R^1$ is a methyl group;
In the formula (1), compounds wherein $R^1$ is an ethyl group;
In the formula (1), compounds wherein $R^1$ is a propyl group;
In the formula (1), compounds wherein $R^1$ is a cyclopropylmethyl group;
In the formula (1), compounds wherein $R^1$ is a cyclopropyl group;
In the formula (1), compounds wherein $R^2$ is a C1 to C6 chain hydrocarbon group optionally having one or more atoms or groups selected from group U;
In the formula (1), compounds wherein $R^2$ is a phenyl group optionally having one or more atoms or groups selected from group W;
In the formula (1), compounds wherein $R^2$ is a 5- or 6-membered heterocyclic group optionally having one or more atoms or groups selected from group W;
In the formula (1), compounds wherein $R^2$ is $OR^8$;
In the formula (1), compounds wherein $R^2$ is $S(O)_m R^8$ or $S(O)_2 NR^8 R^9$;
In the formula (1), compounds wherein $R^2$ is $NR^8 R^9$, $NR^8 CO_2 R^9$ or $NR^8 C(O)R^9$;
In the formula (1), compounds wherein $R^2$ is a $CO_2 R^8$, $C(O)R^8$, or $C(O)NR^8 R^9$;
In the formula (1), compounds wherein $R^2$ is a halogen atom;
In the formula (1), compounds wherein $R^2$ is a hydrogen atom;
In the formula (1), compounds wherein $R^2$ is a halogen atom or a hydrogen atom;
In the formula (1), compounds wherein $R^3$ and $R^4$ are the same or different and are a C1 to C6 chain hydrocarbon group optionally having one or more atoms or groups selected from group U or a hydrogen atom;
In the formula (1), compounds wherein $R^3$ and $R^4$ are the same or different and are a phenyl group optionally having one or more atoms or groups selected from group W or a hydrogen atom;
In the formula (1), compounds wherein $R^3$ and $R^4$ are the same or different and are a 5- or 6-membered heterocyclic group optionally having one or more atoms or groups selected from group W or a hydrogen atom;
In the formula (1), compounds wherein $R^3$ and $R^4$ are the same or different and are $OR^8$ or a hydrogen atom;
In the formula (1), compounds wherein $R^3$ and $R^4$ are the same or different and are $S(O)_m R^8$ or a hydrogen atom;
In the formula (1), compounds wherein $R^3$ and $R^4$ are the same or different and are $SO_2 NR^8 R^9$ or a hydrogen atom;
In the formula (1), compounds wherein $R^3$ and $R^4$ are the same or different and are $NR^8 R^9$ or a hydrogen atom;
In the formula (1), compounds wherein $R^3$ and $R^4$ are the same or different and are $NR^8 CO_2 R^9$ or a hydrogen atom;
In the formula (1), compounds wherein $R^3$ and $R^4$ are the same or different and are $NR^8 C(O)R^9$ or a hydrogen atom;
In the formula (1), compounds wherein $R^3$ and $R^4$ are the same or different and are $CO_2 R^8$ or a hydrogen atom;
In the formula (1), compounds wherein $R^3$ and $R^4$ are the same or different and are $C(O)R^8$ or a hydrogen atom;
In the formula (1), compounds wherein $R^3$ and $R^4$ are the same or different and are $C(O)NR^8 R^9$ or a hydrogen atom;
In the formula (1), compounds wherein $R^3$ and $R^4$ are the same or different and are a halogen atom or a hydrogen atom;
In the formula (1), compounds wherein $R^3$ and $R^4$ are the same or different, and $R^3$ and $R^4$, together with the carbon atoms to which they are bound, form a benzene ring optionally having one or more atoms or groups selected from group W;

In the formula (1), compounds wherein $R^3$ and $R^4$ are the same or different, and form a 5- or 6-membered heterocyclic group optionally having one or more atoms or groups selected from group W;

In the formula (1), compounds wherein $R^3$ and $R^4$ are the same or different, and form a 5-, 6-, 7-, or 8-membered nonaromatic ring optionally having one or more atoms or groups selected from group V;

In the formula (1), compounds wherein $R^3$ and $R^4$ are the same or different and are a C1 to C6 chain hydrocarbon group optionally having one or more atoms or groups selected from group U, $OR^8$, $S(O)_m R^8$, a halogen atom, or a hydrogen atom;

In the formula (1), compounds wherein $R^3$ and $R^4$ are the same or different and are a C1 to C6 chain hydrocarbon group having one or more halogen atoms, $OR^8$, wherein RE represents a C1 to C6 chain hydrocarbon group having one or more halogen atoms, or $S(O)_m R^8$, wherein $R^8$ represents a C1 to C6 chain hydrocarbon group having one or more halogen atoms, a halogen atom, or a hydrogen atom;

In the formula (1), compounds wherein $R^3$ and $R^4$ are the same or different and are a C1 to C6 perfluoroalkyl group having one or more halogen atoms, $OR^8$, wherein $R^8$ represents a C1 to C6 perfluoroalkyl group, or $S(O)_m R^8$, wherein $R^8$ represents a C1 to C6 perfluoroalkyl group, a halogen atom, or a hydrogen atom;

In the formula (1), compounds wherein $R^3$ is a C1 to C6 chain hydrocarbon group optionally having one or more atoms or groups selected from group U, and $R^4$ is a hydrogen atom;

In the formula (1), compounds wherein $R^3$ is a phenyl group optionally having one or more atoms or groups selected from group W, and $R^4$ is a hydrogen atom;

In the formula (1), compounds wherein $R^3$ is a 5- or 6-membered heterocyclic group optionally having one or more atoms or groups selected from group W, and $R^4$ is a hydrogen atom;

In the formula (1), compounds wherein $R^3$ is $OR^8$, and $R^4$ is a hydrogen atom;

In the formula (1), compounds wherein $R^3$ is $S(O)_m R^8$, and $R^4$ is a hydrogen atom;

In the formula (1), compounds wherein $R^3$ is $SO_2 NR^8 R^9$, and $R^4$ is a hydrogen atom;

In the formula (1), compounds wherein $R^3$ is $NR^8 R^9$, and $R^4$ is a hydrogen atom;

In the formula (1), compounds wherein $R^3$ is $NR^8 CO_2 R^9$, and $R^4$ is a hydrogen atom;

In the formula (1), compounds wherein $R^3$ is $NR^8 C(O)R^9$, and $R^4$ is a hydrogen atom;

In the formula (1), compounds wherein $R^3$ is $CO_2 R^8$, and $R^4$ is a hydrogen atom;

In the formula (1), compounds wherein $R^3$ is $C(O)R^8$, and $R^4$ is a hydrogen atom;

In the formula (1), compounds wherein $R^3$ is $C(O)NR^8 R^9$, and $R^4$ is a hydrogen atom;

In the formula (1), compounds wherein $R^3$ is a halogen atom, and
$R^4$ is a hydrogen atom;

In the formula (1), compounds wherein $R^3$ is a C1 to C6 chain hydrocarbon group optionally having one or more halogen atoms, and $R^4$ is a hydrogen atom;

In the formula (1), compounds wherein $R^3$ is a C1 to C6 chain hydrocarbon group having one or more halogen atoms, and $R^4$ is a hydrogen atom;

In the formula (1), compounds wherein $R^3$ is a C1 to C6 alkyl group having one or more halogen atoms, and $R^4$ is a hydrogen atom;

In the formula (1), compounds wherein $R^3$ is a C1 to C6 perfluoroalkyl group, and $R^4$ is a hydrogen atom;

In the formula (1), compounds wherein $R^3$ is $OR^8$, wherein $R^8$ represents a C1 to C6 chain hydrocarbon group having one or more halogen atoms, and $R^4$ is a hydrogen atom;

In the formula (1), compounds wherein $R^3$ is $OR^8$, wherein $R^8$ represents a C1 to C6 perfluoroalkyl group, and $R^4$ is a hydrogen atom;

In the formula (1), compounds wherein $R^3$ is $S(O)_m R^8$, wherein $R^8$ represents a C1 to C6 perfluoroalkyl group, and $R^4$ is a hydrogen atom;

In the formula (1), compounds wherein $R^3$ is $OR^8$, wherein $R^8$ represents a C1 to C6 perfluoroalkyl group, and $R^4$ is a hydrogen atom;

In the formula (1), compounds wherein $R^3$ is a trifluoromethyl group, a pentafluoroethyl group, a heptafluoroisopropyl group, a trifluoromethoxy group, a trifluoromethylsulfanyl group, a trifluoromethylsulfinyl group, or a trifluoromethylsulfonyl group, and $R^4$ is a hydrogen atom;

In the formula (1), compounds wherein $R^3$ is a trifluoromethyl group, and $R^4$ is a hydrogen atom;

In the formula (1), compounds wherein $R^3$ is a pentafluoroethyl group, and $R^4$ is a hydrogen atom;

In the formula (1), compounds wherein $R^3$ is a trifluoromethylsulfanyl group, and $R^4$ is a hydrogen atom;

In the formula (1), compounds wherein $R^3$ is a trifluoromethylsulfinyl group, and $R^4$ is a hydrogen atom;

In the formula (1), compounds wherein $R^3$ is a trifluoromethylsulfonyl group, and $R^4$ is a hydrogen atom;

In the formula (1), compounds wherein $R^5$ is a C1 to C6 chain hydrocarbon group optionally having one or more atoms or groups selected from group X, $CO_2 R^8$, $C(O)R^8$, a C3 to C9 alicyclic hydrocarbon group optionally having one or more atoms or groups selected from group V, or a hydrogen atom;

In the formula (1), compounds wherein $R^5$ is a C1 to C6 chain hydrocarbon group optionally having one or more atoms or groups selected from group X;

In the formula (1), compounds wherein $R^5$ is $CO_2 R^8$;

In the formula (1), compounds wherein $R^5$ is $C(O)R^8$;

In the formula (1), compounds wherein $R^5$ is a C3 to C9 alicyclic hydrocarbon group optionally having one or more atoms or groups selected from group V;

In the formula (1), compounds wherein $R^5$ is a C3 to C9 alicyclic hydrocarbon group optionally having one or more atoms or groups selected from group V;

In the formula (1), compounds wherein $R^5$ is a hydrogen atom;

In the formula (1), compounds wherein $R^6$ and $R^7$ are the same or different and are a C1 to C6 chain hydrocarbon group optionally having one or more halogen atoms, or a hydrogen atom;

In the formula (1), compounds wherein $R^6$ and $R^7$ are the same or different and are a halogen atom or a hydrogen atom;

In the formula (1), compounds wherein $R^6$ and $R^7$ are the same or different and are $OR^8$, $S(O)_m R^3$, $NR^8 R^9$, a halogen atom, or a hydrogen atom;

In the formula (1), compounds wherein $R^6$ and $R^7$ are a hydrogen atom;

In the formula (1), compounds wherein $R^1$ is a C1 to C6 alkyl group optionally having one or more atoms or groups selected from the group consisting of halogen atoms and cyclopropyl groups, wherein the cyclopropyl group optionally has one or more halogen atoms or one or more C1 to C3 alkyl groups, a C2 to C6 alkenyl group optionally having one or more halogen atoms, a C2 to C6 alkynyl group optionally having one or more halogen atoms, or a C3 to C6 cycloalkyl group optionally having one or more atoms or groups selected from the group consisting of halogen atoms and C1 to C6 alkyl groups optionally having one or more halogen atoms,
$R^2$ is a halogen atom or a hydrogen atom,
$R^3$ and $R^4$ are the same or different and are a C1 to C6 chain hydrocarbon group optionally having one or more atoms or groups selected from group U, $OR^8$, $S(O)_mR^8$, a halogen atom, or a hydrogen atom, and
$R^5$ is a C1 to C6 chain hydrocarbon group optionally having one or more atoms or groups selected from group X, $CO_2R^8$, $C(O)R^8$, a C3 to C9 alicyclic hydrocarbon group optionally having one or more atoms or groups selected from group V, or a hydrogen atom;
In (1), compounds wherein
$A^1$ is $NR^5$,
$A^2$ is $CR^6$,
$A^3$ is a nitrogen atom,
$R^1$ is a C1 to C6 chain hydrocarbon group optionally having one or more atoms or groups selected from group U, and $R^2$ is a hydrogen atom,
G is group G1, group G2, or group G5, and Q is an oxygen atom,
$R^{10}$ is a hydrogen atom,
$R^{11}$ represents a C3 to C9 alicyclic hydrocarbon group optionally having one or more atoms or groups selected from group V, $OR^{25}$, wherein $R^{25}$ represents a C1 to C6 chain hydrocarbon group having one or more atoms or groups selected from group Z, $NR^{30}R^{31}$, wherein $R^{30}$ and $R^{31}$ are the same or different, and represent a C1 to C6 chain hydrocarbon group optionally having one or more atoms or groups selected from group Y, or $C(O)R^{32}$, wherein $R^{32}$ represents $OR^8$, and $R^9$ represents a C1 to C6 chain hydrocarbon group optionally having one or more atoms or groups selected from group Y,
$R^{12}$ is a hydrogen atom, or $SO_2R^{33}$, wherein $R^{33}$ represents a C1 to C6 chain hydrocarbon group optionally having one or more atoms or groups selected from group Y,
$R^{13}$ is a C1 to C6 chain hydrocarbon group optionally having one or more atoms or groups selected from group Y,
$R^{19}$ is a hydrogen atom,
$R^{20}$ is $NR^{54}R^{55}$, wherein $R^{54}$ and $R^{55}$ are the same or different, and are a C1 to C6 chain hydrocarbon group optionally having one or more atoms or groups selected from group Y,
$R^3$ is a C1 to C6 chain hydrocarbon group optionally having one or more atoms or groups selected from group U,
$R^4$ is a hydrogen atom,
$R^5$ is a C1 to C6 chain hydrocarbon group optionally having one or more atoms or groups selected from group X, and
$R^6$ is a hydrogen atom;
In (1), compounds wherein
$A^1$ is $NR^5$,
$A^2$ is $CR^6$,
$A^3$ is a nitrogen atom,
$R^1$ is a C1 to C6 alkyl group optionally having one or more halogen atoms,
$R^2$ is a hydrogen atom,
G is group G1, group G2, or group G5, and Q is an oxygen atom,
$R^{10}$ is a hydrogen atom,
$R^{11}$ is a C3 to C9 cycloalkyl groups optionally having one or more halogen atoms, $OR^{25}$, wherein $R^{25}$ represents a C1 to C6 alkyl group having one phenyl group optionally having one or more halogen atoms, $NR^{30}R^{31}$, wherein $R^{30}$ and $R^{31}$ are the same or different and represent a C1 to C6 alkyl group optionally having one or more halogen atoms, or $C(O)R^{32}$, wherein $R^{32}$ represents $OR^8$, and $R^8$ represents a C1 to C6 alkyl group optionally having one or more halogen atoms,
$R^{12}$ is a hydrogen atom, or $SO_2R^{33}$, wherein $R^{33}$ represents a C1 to C6 alkyl group optionally having one or more halogen atoms, $R^{13}$ is a C1 to C6 alkyl group optionally having one or more halogen atoms,
$R^{19}$ is a hydrogen atom,
$R^{20}$ is $NR^{54}R^{55}$, wherein $R^{54}$ and $R^{55}$ are the same or different and represent a C1 to C6 alkyl group optionally having one or more halogen atoms,
$R^3$ is a C1 to C6 alkyl group optionally having one or more halogen atoms,
$R^4$ is a hydrogen atom,
$R^5$ is a C1 to C6 alkyl group optionally having one or more halogen atoms, and
$R^6$ is a hydrogen atom;
In the formula (1), compounds wherein
$R^1$ is a methyl group, an ethyl group, a propyl group, a trifluoromethyl group, a 2,2,2-trifluoroethyl group, a cyclopropylmethyl group, or a cyclopropyl group,
$R^2$ is a hydrogen atom,
$R^3$ and $R^4$ are the same or different and are a C1 to C6 chain hydrocarbon group having one or more halogen atoms, $OR^8$, wherein $R^8$ represents a C1 to C6 chain hydrocarbon group having one or more halogen atoms, or $S(O)_mR^8$, wherein $R^8$ represents a C1 to C6 chain hydrocarbon group having one or more halogen atoms, a halogen atom, or a hydrogen atom,
$R^5$ is a C1 to C6 alkyl group optionally having one or more halogen atoms or a hydrogen atom, and
$R^6$ and $R^7$ are a hydrogen atom;
Compounds represented by formula (1A),

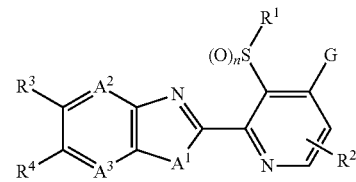

(1A)

wherein symbols represent the same meaning as in the formula (1);
In the formula (1A), compounds wherein $A^1$ is $NR^5$, $A^2$ is $CR^6$, and $A^3$ is a nitrogen atom;
In the formula (1A), compounds wherein $A^1$ is $NR^5$, $A^2$ is $CR^6$, and $A^3$ is $CR^7$;
In the formula (1A), compounds wherein $A^1$ is $NR^5$, $A^2$ is CH, and $A^3$ is a nitrogen atom;
In the formula (1A), compounds wherein $A^1$ is $NR^5$, $A^2$ is CH, and $A^3$ is $CR^7$;
In the formula (1A), compounds wherein $A^1$ is $NR^5$, $A^2$ is CH, and $A^3$ is CH;
In the formula (1A), compounds wherein $A^1$ is $NR^5$, $R^5$ is a methyl group, $A^2$ is $CR^6$, and $A^3$ is a nitrogen atom;
In the formula (1A), compounds wherein $A^1$ is $NR^5$, $R^5$ is a methyl group, $A^2$ is $CR^6$, and $A^3$ is $CR^7$;
In the formula (1A), compounds wherein $A^1$ is $NR^5$, $R^5$ is a methyl group, $A^2$ is CH, and $A^3$ is a nitrogen atom;
In the formula (1A), compounds wherein $A^1$ is $NR^5$, $R^5$ is a methyl group, $A^2$ is CH, and $A^3$ is $CR^7$;
In the formula (1A), compounds wherein $A^1$ is $NR^5$, $R^5$ is a methyl group, $A^2$ is CH, and $A^3$ is CH;

In the formula (1A), compounds wherein A¹ is a sulfur atom, A² is CR⁶, and A³ is a nitrogen atom;
In the formula (1A), compounds wherein A¹ is a sulfur atom, A² is CR⁶, and A³ is CR⁷;
In the formula (1A), compounds wherein A¹ is a sulfur atom, A² is CH, and A³ is a nitrogen atom;
In the formula (1A), compounds wherein A¹ is a sulfur atom, A² is CH, and A³ is CR⁷;
In the formula (1A), compounds wherein A¹ is a sulfur atom, A is CH, and A³ is CH;
In the formula (1A), compounds wherein A¹ is an oxygen atom, A² is CR⁶, and A³ is a nitrogen atom;
In the formula (1A), compounds wherein A¹ is an oxygen atom, A² is CR⁶, and A³ is CR⁷;
In the formula (1A), compounds wherein A¹ is an oxygen atom, A² is CH, and A³ is a nitrogen atom;
In the formula (1A), compounds wherein A¹ is an oxygen atom, A² is CH, and A³ is CR⁷;
In the formula (1A), compounds wherein A¹ is an oxygen atom, A² is CH, and A³ is CH;
Compounds represented by formula (1B),

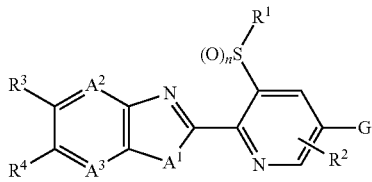

(1B)

wherein symbols represent the same meaning as in the formula (1);
In the formula (1B), compounds wherein A¹ is NR⁵, A² is CR⁶, and A³ is a nitrogen atom;
In the formula (1B), compounds wherein A¹ is NR⁵, A² is CR⁶, and A³ is CR⁷;
In the formula (1B), compounds wherein A¹ is NR⁵, A² is CH, and A³ is a nitrogen atom;
In the formula (1B), compounds wherein A¹ is NR⁵, A² is CH, and A³ is CR⁷;
In the formula (1B), compounds wherein A¹ is NR⁵, A² is CH, and A³ is CH;
In the formula (1B), compounds wherein A¹ is NR³, R⁵ is a methyl group, A² is CR⁶, and A³ is a nitrogen atom;
In the formula (1B), compounds wherein A¹ is NR⁵, R⁵ is a methyl group, A² is CR⁶, and A³ is CR⁷;
In the formula (1B), compounds wherein A¹ is NR⁵, R⁵ is a methyl group, A² is CH, and A³ is a nitrogen atom;
In the formula (1B), compounds wherein A¹ is NR³, R⁵ is a methyl group, A² is CH, and A³ is CR⁷;
In the formula (1B), compounds wherein A¹ is NR⁵, R⁵ is a methyl group, A² is CH, and A³ is CH;
In the formula (1B), compounds wherein A¹ is a sulfur atom, A² is CR⁶, and A³ is a nitrogen atom;
In the formula (1B), compounds wherein A¹ is a sulfur atom, A² is CR⁶, and A³ is CR⁷;
In the formula (1B), compounds wherein A¹ is a sulfur atom, A² is CH, and A³ is a nitrogen atom;
In the formula (1B), compounds wherein A¹ is a sulfur atom, A² is CH, and A³ is CR⁷;
In the formula (1B), compounds wherein A¹ is a sulfur atom, A² is CH, and A³ is CH;
In the formula (1B), compounds wherein A¹ is an oxygen atom, A² is CR⁶, and A³ is a nitrogen atom;
In the formula (1B), compounds wherein A¹ is an oxygen atom, A² is CR⁶, and A³ is CR⁷;
In the formula (1B), compounds wherein A¹ is an oxygen atom, A² is CH, and A³ is a nitrogen atom;
In the formula (1B), compounds wherein A¹ is an oxygen atom, A² is CH, and A³ is CR⁷;
In the formula (1B), compounds wherein A¹ is an oxygen atom, A² is CH, and A³ is CH;
In the formula (1B), compounds wherein A¹ is NR⁵ or an oxygen atom, A² is CR⁶, and A³ is CR⁷ or a nitrogen atom;
In the formula (1B), compounds wherein
A¹ is NR⁵ or an oxygen atom,
A² is CR⁶,
A³ is CR⁷ or a nitrogen atom,
R¹ is a C1 to C6 chain hydrocarbon group optionally having one or more atoms or groups selected from group U,
R² is a hydrogen atom,
R³ is a C1 to C6 chain hydrocarbon group optionally having one or more atoms or groups selected from group U, or S(O)ₘR⁸, and
R⁴ is a hydrogen atom;
In the formula (1B), compounds wherein
A¹ is NR⁵ or an oxygen atom, R⁵ is a methyl group,
A² is CH,
A³ is CH or a nitrogen atom,
R¹ is a C1 to C6 alkyl group,
R² is a hydrogen atom,
R³ is a C1 to C6 alkyl group having one or more halogen atoms, a C1 to C6 alkylsulfanyl group having one or more halogen atoms, a C1 to C6 alkylsulfinyl group having one or more halogen atoms, or a C1 to C6 alkylsulfonyl group having one or more halogen atoms, and
R⁴ is a hydrogen atom;
In the formula (1B), compounds wherein
A¹ is NR⁵ or an oxygen atom, R⁵ is a methyl group,
A² is CH,
A³ is CH or a nitrogen atom,
R¹ is an ethyl group,
R² is a hydrogen atom,
R³ is a C1 to C3 perfluoroalkyl group, a C1 to C3 perfluoroalkylsulfanyl group, a C1 to C3 perfluoroalkylsulfinyl group, or a C1 to C3 perfluoroalkylsulfonyl group, and
R⁴ is a hydrogen atom;
Compounds represented by formula (1C),

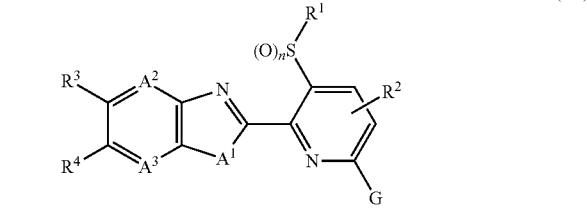

(1C)

wherein symbols represent the same meaning as in the formula (1);
In the formula (1C), compounds wherein A¹ is NR⁵, A² is CR⁶, and A³ is a nitrogen atom;
In the formula (1C), compounds wherein A¹ is NR⁵, A² is CR⁶, and A³ is CR⁷;
In the formula (1C), compounds wherein A¹ is NR⁵, A² is CH, and A³ is a nitrogen atom;
In the formula (1C), compounds wherein A¹ is NR⁵, A² is CH, and A³ is CR⁷;

In the formula (1C), compounds wherein $A^1$ is $NR^5$, $A^2$ is CH, and $A^3$ is CH;
In the formula (1C), compounds wherein $A^1$ is $NR^5$, $R^5$ is a methyl group, $A^2$ is $CR^6$, and $A^3$ is a nitrogen atom;
In the formula (1C), compounds wherein $A^1$ is $NR^5$, $R^5$ is a methyl group, $A^2$ is $CR^6$, and $A^3$ is $CR^7$;
In the formula (1C), compounds wherein $A^1$ is $NR^5$, $R^5$ is a methyl group, $A^2$ is CH, and $A^3$ is a nitrogen atom;
In the formula (1C), compounds wherein $A^1$ is $NR^5$, $R^5$ is a methyl group, $A^2$ is CH, and $A^3$ is $CR^7$;
In the formula (1C), compounds wherein $A^1$ is $NR^5$, $R^5$ is a methyl group, $A^2$ is CH, and $A^3$ is CH;
In the formula (1C), compounds wherein $A^1$ is a sulfur atom, $A^2$ is $CR^6$, and $A^3$ is a nitrogen atom;
In the formula (1C), compounds wherein $A^1$ is a sulfur atom, $A^2$ is $CR^6$, and $A^3$ is $CR^7$;
In the formula (1C), compounds wherein $A^1$ is a sulfur atom, $A^2$ is CH, and $A^4$ is a nitrogen atom;
In the formula (1C), compounds wherein $A^1$ is a sulfur atom, A is CH, and $A^3$ is $CR^7$;
In the formula (1C), compounds wherein $A^1$ is a sulfur atom, $A^2$ is CH, and $A^3$ is CH;
In the formula (1C), compounds wherein $A^1$ is an oxygen atom, $A^2$ is $CR^6$, and $A^3$ is a nitrogen atom;
In the formula (1C), compounds wherein $A^1$ is an oxygen atom, $A^2$ is $CR^6$, and $A^3$ is CRT;
In the formula (1C), compounds wherein $A^1$ is an oxygen atom, $A^2$ is C, and $A^3$ is a nitrogen atom;
In the formula (1C), compounds wherein $A^1$ is an oxygen atom, $A^2$ is CH, and $A^3$ is $CR^7$;
In the formula (1C), compounds wherein $A^1$ is an oxygen atom, $A^2$ is CH, and $A^3$ is CH;
In the formula (1), compounds wherein $A^1$ is $NR^5$ or an oxygen atom, $A^2$ is $CR^6$, and $A^3$ is $CR^7$ or a nitrogen atom;
In the formula (1C), compounds wherein
$A^1$ is $NR^5$ or an oxygen atom,
$A^2$ is $CR^6$,
$A^3$ is $CR^7$ or a nitrogen atom,
$R^1$ is a C1 to C6 chain hydrocarbon group optionally having one or more atoms or groups selected from group U,
$R^2$ is a hydrogen atom,
$R^3$ is a C1 to C6 chain hydrocarbon group optionally having one or more atoms or groups selected from group U, or $S(O)_mR^3$, and
$R^4$ is a hydrogen atom;
In the formula (1C), compounds wherein
$A^1$ is $NR^5$ or an oxygen atom, $R^5$ is a methyl group,
$A^2$ is CH,
$A^3$ is CH or a nitrogen atom,
$R^1$ is a C1 to C6 alkyl group,
$R^2$ is a hydrogen atom,
$R^3$ is a C1 to C6 alkyl group having one or more halogen atoms, a C1 to C6 alkylsulfanyl group having one or more halogen atoms, a C1 to C6 alkylsulfinyl group having one or more halogen atoms, or a C1 to C6 alkylsulfonyl group having one or more halogen atoms, and
$R^4$ is a hydrogen atom;
In the formula (1C), compounds wherein
$A^1$ is $NR^5$ or an oxygen atom, $R^5$ is a methyl group,
$A^2$ is CH,
$A^3$ is CH or a nitrogen atom,
$R^1$ is an ethyl group,
$R^2$ is a hydrogen atom,
$R^3$ is a C1 to C3 perfluoroalkyl group, a C1 to C3 perfluoroalkylsulfanyl group, a C1 to C3 perfluoroalkylsulfinyl group, or a C1 to C3 perfluoroalkylsulfonyl group, and
$R^4$ is a hydrogen atom;

Compounds represented by formula (1N1)

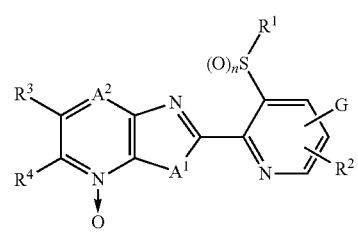

(1N1)

wherein symbols represent the same meaning as in the formula (1);
Compounds represented by formula (1N2)

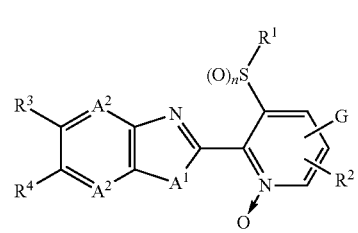

(1N2)

wherein symbols represent the same meaning as in the formula (1);
Compounds represented by formula (1N3)

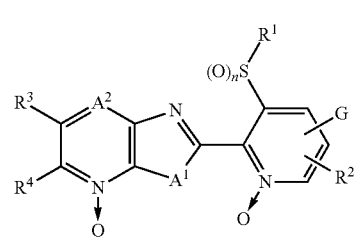

(1N3)

wherein symbols represent the same meaning as in the formula (1);
In the formula (1), compounds wherein G is group G1;
In the formula (1), compounds wherein G is group G2;
In the formula (1), compounds wherein G is group G3;
In the formula (1), compounds wherein G is group G4;
In the formula (1), compounds wherein G is group G5;
In the formula (1), compounds wherein G is group G6;
In the formula (1), compounds wherein G is group G7;
In the formula (1), compounds wherein G is group G2, group G3, group G4, group G5, or group G6;
In the formula (1), compounds wherein G is group G1, and $R^{11}$ is $R^{25}$, $OR^{27}$, $SR^{29}$, $NR^{30}R^{31}$, or $C(O)R^{32}$;
In the formula (1), compounds wherein G is group G1, and $R^{11}$ is $R^{25}$ or $OR^{27}$;
In the formula (1), compounds wherein G is group G1, and $R^{11}$ is $R^{26}$ or $OR^{28}$;
In the formula (1), compounds wherein G is group G1, and $R^{11}$ is $R^{25}$, $OR^{27}$, $SR^{29}$, $NR^{30}R^{31}$, or $C(O)R^{32}$;
In the formula (1), compounds wherein G is group G1, and $R^{11}$ is $SR^{29}$, $NR^{30}R^{31}$, or $C(O)R^{32}$; and
In the formula (1A), compounds wherein $A^1$, $A^2$, $A^3$ and G are as in the combinations of [Table 1] to [Table 10] (embodiment 1 to embodiment 243).

Here, for example, embodiment 1 represents "in the formula (1A), compounds wherein $A^1$ is $NR^5$, $A^2$ is $CR^6$, $A^3$ is $CR^7$, and G is $G^1$".

TABLE 1

| Embodiment | $A^1$ | $A^2$ | $A^3$ | G |
|---|---|---|---|---|
| 1 | $NR^5$ | $CR^6$ | $CR^7$ | G1 |
| 2 | $NR^5$ | $CR^6$ | $CR^7$ | G2 |
| 3 | $NR^5$ | $CR^6$ | $CR^7$ | G3 |
| 4 | $NR^5$ | $CR^6$ | $CR^7$ | G4 |
| 5 | $NR^5$ | $CR^6$ | $CR^7$ | G5 |
| 6 | $NR^5$ | $CR^6$ | $CR^7$ | G6 |
| 7 | $NR^5$ | $CR^6$ | $CR^7$ | G7 |
| 8 | $NR^5$ | $CR^6$ | $CR^7$ | G1, G7 |
| 9 | $NR^5$ | $CR^6$ | $CR^7$ | G2, G3, G4, G5, G6 |
| 10 | $NR^5$ | $CR^6$ | $CR^7$ | J1, J2, J3, J4, G7 |
| 11 | $NR^5$ | $CR^6$ | $CR^7$ | J1 |
| 12 | $NR^5$ | $CR^6$ | $CR^7$ | J2 |
| 13 | $NR^5$ | $CR^6$ | $CR^7$ | J3 |
| 14 | $NR^5$ | $CR^6$ | $CR^7$ | J4 |
| 15 | $NR^5$ | $CR^6$ | $CR^7$ | J5 |
| 16 | $NR^5$ | $CR^6$ | $CR^7$ | J6 |
| 17 | $NR^5$ | $CR^6$ | $CR^7$ | J7 |
| 18 | $NR^5$ | $CR^6$ | $CR^7$ | J8 |
| 19 | $NR^5$ | $CR^6$ | $CR^7$ | J9 |
| 20 | $NR^5$ | $CR^6$ | $CR^7$ | J10 |
| 21 | $NR^5$ | $CR^6$ | $CR^7$ | J11 |
| 22 | $NR^5$ | $CR^6$ | $CR^7$ | J12 |
| 23 | $NR^5$ | $CR^6$ | $CR^7$ | J13 |
| 24 | $NR^5$ | $CR^6$ | $CR^7$ | J14 |
| 25 | $NR^5$ | $CR^6$ | $CR^7$ | J15 |

TABLE 2

| Embodiment | $A^1$ | $A^2$ | $A^3$ | G |
|---|---|---|---|---|
| 26 | $NR^5$ | $CR^6$ | $CR^7$ | J16 |
| 27 | $NR^5$ | $CR^6$ | $CR^7$ | J17 |
| 28 | $NR^5$ | $CR^6$ | $CR^7$ | J18 |
| 29 | $NR^5$ | $CR^6$ | $CR^7$ | J10 |
| 30 | $NR^5$ | $CR^6$ | $CR^7$ | J20 |
| 31 | $NR^5$ | $CR^6$ | $CR^7$ | J21 |
| 32 | $NR^5$ | $CR^6$ | $CR^7$ | J22 |
| 33 | $NR^5$ | $CR^6$ | $CR^7$ | J23 |
| 34 | $NR^5$ | $CR^6$ | $CR^7$ | J24 |
| 35 | $NR^5$ | $CR^6$ | $CR^7$ | J25 |
| 36 | $NR^5$ | $CR^6$ | $CR^7$ | J26 |
| 37 | $NR^5$ | $CR^6$ | $CR^7$ | J27 |
| 38 | $NR^5$ | $CR^6$ | N | G1 |
| 39 | $NR^5$ | $CR^6$ | N | G2 |
| 40 | $NR^5$ | $CR^6$ | N | G3 |
| 41 | $NR^5$ | $CR^6$ | N | G4 |
| 42 | $NR^5$ | $CR^6$ | N | G5 |
| 43 | $NR^5$ | $CR^6$ | N | G6 |
| 44 | $NR^5$ | $CR^6$ | N | G7 |
| 45 | $NR^5$ | $CR^6$ | N | G1, G7 |
| 46 | $NR^5$ | $CR^6$ | N | G2, G3, G4, G5, G6 |
| 47 | $NR^5$ | $CR^6$ | N | J1, J2, J3, J4, G7 |
| 48 | $NR^5$ | $CR^6$ | N | J1 |
| 49 | $NR^5$ | $CR^6$ | N | J2 |
| 50 | $NR^5$ | $CR^6$ | N | J3 |

TABLE 3

| Embodiment | $A^1$ | $A^2$ | $A^3$ | G |
|---|---|---|---|---|
| 51 | $NR^5$ | $CR^6$ | N | J4 |
| 52 | $NR^5$ | $CR^6$ | N | J5 |
| 53 | $NR^5$ | $CR^6$ | N | J6 |
| 54 | $NR^5$ | $CR^6$ | N | J7 |
| 55 | $NR^5$ | $CR^6$ | N | J8 |
| 56 | $NR^5$ | $CR^6$ | N | J9 |
| 57 | $NR^5$ | $CR^6$ | N | J10 |
| 58 | $NR^5$ | $CR^6$ | N | J11 |
| 59 | $NR^5$ | $CR^6$ | N | J12 |
| 60 | $NR^5$ | $CR^6$ | N | J13 |
| 61 | $NR^5$ | $CR^6$ | N | J14 |
| 62 | $NR^5$ | $CR^6$ | N | J15 |
| 63 | $NR^5$ | $CR^6$ | N | J16 |
| 64 | $NR^5$ | $CR^6$ | N | J17 |
| 65 | $NR^5$ | $CR^6$ | N | J18 |
| 66 | $NR^5$ | $CR^6$ | N | J10 |
| 67 | $NR^5$ | $CR^6$ | N | J20 |
| 68 | $NR^5$ | $CR^6$ | N | J21 |
| 69 | $NR^5$ | $CR^6$ | N | J22 |
| 70 | $NR^5$ | $CR^6$ | N | J23 |
| 71 | $NR^5$ | $CR^6$ | N | J24 |
| 72 | $NR^5$ | $CR^6$ | N | J25 |
| 73 | $NR^5$ | $CR^6$ | N | J26 |
| 74 | $NR^5$ | $CR^6$ | N | J27 |
| 75 | O | $CR^6$ | $CR^7$ | G1 |

TABLE 4

| Embodiment | $A^1$ | $A^2$ | $A^3$ | G |
|---|---|---|---|---|
| 76 | O | $CR^6$ | $CR^7$ | G2 |
| 77 | O | $CR^6$ | $CR^7$ | G3 |
| 78 | O | $CR^6$ | $CR^7$ | G4 |
| 79 | O | $CR^6$ | $CR^7$ | G5 |
| 80 | O | $CR^6$ | $CR^7$ | G6 |
| 81 | O | $CR^6$ | $CR^7$ | G7 |
| 82 | O | $CR^6$ | $CR^7$ | G1, G7 |
| 83 | O | $CR^6$ | $CR^7$ | G2, G3, G4, G5, G6 |
| 84 | O | $CR^6$ | $CR^7$ | J1, J2, J3, J4, G7 |
| 85 | O | $CR^6$ | $CR^7$ | J1 |
| 86 | O | $CR^6$ | $CR^7$ | J2 |
| 87 | O | $CR^6$ | $CR^7$ | J3 |
| 88 | O | $CR^6$ | $CR^7$ | J4 |
| 89 | O | $CR^6$ | $CR^7$ | J5 |
| 90 | O | $CR^6$ | $CR^7$ | J6 |
| 91 | O | $CR^6$ | $CR^7$ | J7 |
| 92 | O | $CR^6$ | $CR^7$ | J8 |
| 93 | O | $CR^6$ | $CR^7$ | J9 |
| 94 | O | $CR^6$ | $CR^7$ | J10 |
| 95 | O | $CR^6$ | $CR^7$ | J11 |
| 96 | O | $CR^6$ | $CR^7$ | J12 |
| 97 | O | $CR^6$ | $CR^7$ | J13 |
| 98 | O | $CR^6$ | $CR^7$ | J14 |
| 99 | O | $CR^6$ | $CR^7$ | J15 |
| 100 | O | $CR^6$ | $CR^7$ | J16 |

TABLE 5

| Embodiment | $A^1$ | $A^2$ | $A^3$ | G |
|---|---|---|---|---|
| 101 | O | $CR^6$ | $CR^7$ | J17 |
| 102 | O | $CR^6$ | $CR^7$ | J18 |
| 103 | O | $CR^6$ | $CR^7$ | J10 |
| 104 | O | $CR^6$ | $CR^7$ | J20 |
| 105 | O | $CR^6$ | $CR^7$ | J21 |
| 106 | O | $CR^6$ | $CR^7$ | J22 |
| 107 | O | $CR^6$ | $CR^7$ | J23 |
| 108 | O | $CR^6$ | $CR^7$ | J24 |
| 109 | O | $CR^6$ | $CR^7$ | J25 |
| 110 | O | $CR^6$ | $CR^7$ | J26 |
| 111 | O | $CR^6$ | $CR^7$ | J27 |
| 112 | O | $CR^6$ | N | G1 |
| 113 | O | $CR^6$ | N | G2 |
| 114 | O | $CR^6$ | N | G3 |
| 115 | O | $CR^6$ | N | G4 |
| 116 | O | $CR^6$ | N | G5 |
| 117 | O | $CR^6$ | N | G6 |
| 118 | O | $CR^6$ | N | G7 |
| 119 | O | $CR^6$ | N | G1, G7 |
| 120 | O | $CR^6$ | N | G2, G3, G4, G5, G6 |
| 121 | O | $CR^6$ | N | J1, J2, J3, J4, G7 |

TABLE 5-continued

| Embodiment | $A^1$ | $A^2$ | $A^3$ | G |
|---|---|---|---|---|
| 122 | O | $CR^6$ | N | J1 |
| 123 | O | $CR^6$ | N | J2 |
| 124 | O | $CR^6$ | N | J3 |
| 125 | O | $CR^6$ | N | J4 |

TABLE 6

| Embodiment | $A^1$ | $A^2$ | $A^3$ | G |
|---|---|---|---|---|
| 126 | O | $CR^6$ | N | J5 |
| 127 | O | $CR^6$ | N | J6 |
| 128 | O | $CR^6$ | N | J7 |
| 129 | O | $CR^6$ | N | J8 |
| 130 | O | $CR^6$ | N | J9 |
| 131 | O | $CR^6$ | N | J10 |
| 132 | O | $CR^6$ | N | J11 |
| 133 | O | $CR^6$ | N | J12 |
| 134 | O | $CR^6$ | N | J13 |
| 135 | O | $CR^6$ | N | J14 |
| 136 | O | $CR^6$ | N | J15 |
| 137 | O | $CR^6$ | N | J16 |
| 138 | O | $CR^6$ | N | J17 |
| 139 | O | $CR^6$ | N | J18 |
| 140 | O | $CR^6$ | N | J10 |
| 141 | O | $CR^6$ | N | J20 |
| 142 | O | $CR^6$ | N | J21 |
| 143 | O | $CR^6$ | N | J22 |
| 144 | O | $CR^6$ | N | J23 |
| 145 | O | $CR^6$ | N | J24 |
| 146 | O | $CR^6$ | N | J25 |
| 147 | O | $CR^6$ | N | J26 |
| 148 | O | $CR^6$ | N | J27 |
| 149 | S | $CR^6$ | $CR^7$ | G1 |
| 150 | S | $CR^6$ | $CR^7$ | G2 |

TABLE 7

| Embodiment | $A^1$ | $A^2$ | $A^3$ | G |
|---|---|---|---|---|
| 151 | S | $CR^6$ | $CR^7$ | G3 |
| 152 | S | $CR^6$ | $CR^7$ | G4 |
| 153 | S | $CR^6$ | $CR^7$ | G5 |
| 154 | S | $CR^6$ | $CR^7$ | G6 |
| 155 | S | $CR^6$ | $CR^7$ | G7 |
| 156 | S | $CR^6$ | $CR^7$ | G1, G7 |
| 157 | S | $CR^6$ | $CR^7$ | G2, G3, G4, G5, G6 |
| 158 | S | $CR^6$ | $CR^7$ | J1, J2, J3, J4, G7 |
| 159 | S | $CR^6$ | $CR^7$ | J1 |
| 160 | S | $CR^6$ | $CR^7$ | J2 |
| 161 | S | $CR^6$ | $CR^7$ | J3 |
| 162 | S | $CR^6$ | $CR^7$ | J4 |
| 163 | S | $CR^6$ | $CR^7$ | J5 |
| 164 | S | $CR^6$ | $CR^7$ | J6 |
| 165 | S | $CR^6$ | $CR^7$ | J7 |
| 166 | S | $CR^6$ | $CR^7$ | J8 |
| 167 | S | $CR^6$ | $CR^7$ | J9 |
| 168 | S | $CR^6$ | $CR^7$ | J10 |
| 169 | S | $CR^6$ | $CR^7$ | J11 |
| 170 | S | $CR^6$ | $CR^7$ | J12 |
| 171 | S | $CR^6$ | $CR^7$ | J13 |
| 172 | S | $CR^6$ | $CR^7$ | J14 |
| 173 | S | $CR^6$ | $CR^7$ | J15 |
| 174 | S | $CR^6$ | $CR^7$ | J16 |
| 175 | S | $CR^6$ | $CR^7$ | J17 |

TABLE 8

| Embodiment | $A^1$ | $A^2$ | $A^3$ | G |
|---|---|---|---|---|
| 176 | S | $CR^6$ | $CR^7$ | J18 |
| 177 | S | $CR^6$ | $CR^7$ | J10 |
| 178 | S | $CR^6$ | $CR^7$ | J20 |
| 179 | S | $CR^6$ | $CR^7$ | J21 |
| 180 | S | $CR^6$ | $CR^7$ | J22 |
| 181 | S | $CR^6$ | $CR^7$ | J23 |
| 182 | S | $CR^6$ | $CR^7$ | J24 |
| 183 | S | $CR^6$ | $CR^7$ | J25 |
| 184 | S | $CR^6$ | $CR^7$ | J26 |
| 185 | S | $CR^6$ | $CR^7$ | J27 |
| 186 | S | $CR^6$ | N | G1 |
| 187 | S | $CR^6$ | N | G2 |
| 188 | S | $CR^6$ | N | G3 |
| 189 | S | $CR^6$ | N | G4 |
| 190 | S | $CR^6$ | N | G5 |
| 191 | S | $CR^6$ | N | G6 |
| 192 | S | $CR^6$ | N | G7 |
| 193 | S | $CR^6$ | N | G1, G7 |
| 194 | S | $CR^6$ | N | G2, G3, G4, G5, G6 |
| 195 | S | $CR^6$ | N | J1, J2, J3, J4, G7 |
| 196 | S | $CR^6$ | N | J1 |
| 197 | S | $CR^6$ | N | J2 |
| 198 | S | $CR^6$ | N | J3 |
| 199 | S | $CR^6$ | N | J4 |
| 200 | S | $CR^6$ | N | J5 |

TABLE 9

| Embodiment | $A^1$ | $A^2$ | $A^3$ | G |
|---|---|---|---|---|
| 201 | S | $CR^6$ | N | J6 |
| 202 | S | $CR^6$ | N | J7 |
| 203 | S | $CR^6$ | N | J8 |
| 204 | S | $CR^6$ | N | J9 |
| 205 | S | $CR^6$ | N | J10 |
| 206 | S | $CR^6$ | N | J11 |
| 207 | S | $CR^6$ | N | J12 |
| 208 | S | $CR^6$ | N | J13 |
| 209 | S | $CR^6$ | N | J14 |
| 210 | S | $CR^6$ | N | J15 |
| 211 | S | $CR^6$ | N | J16 |
| 212 | S | $CR^6$ | N | J17 |
| 213 | S | $CR^6$ | N | J18 |
| 214 | S | $CR^6$ | N | J10 |
| 215 | S | $CR^6$ | N | J20 |
| 216 | S | $CR^6$ | N | J21 |
| 217 | S | $CR^6$ | N | J22 |
| 218 | S | $CR^6$ | N | J23 |
| 219 | S | $CR^6$ | N | J24 |
| 220 | S | $CR^6$ | N | J25 |
| 221 | S | $CR^6$ | N | J26 |
| 222 | S | $CR^6$ | N | J27 |
| 223 | $NR^5$ | N | $CR^7$ | G1 |
| 224 | $NR^5$ | N | $CR^7$ | G2 |
| 225 | $NR^5$ | N | $CR^7$ | G3 |

TABLE 10

| Embodiment | $A^1$ | $A^2$ | $A^3$ | G |
|---|---|---|---|---|
| 226 | $NR^5$ | N | $CR^7$ | G4 |
| 227 | $NR^5$ | N | $CR^7$ | G5 |
| 228 | $NR^5$ | N | $CR^7$ | G6 |
| 229 | $NR^5$ | N | $CR^7$ | G7 |
| 230 | O | N | $CR^7$ | G1 |
| 231 | O | N | $CR^7$ | G2 |
| 232 | O | N | $CR^7$ | G3 |
| 233 | O | N | $CR^7$ | G4 |
| 234 | O | N | $CR^7$ | G5 |
| 235 | O | N | $CR^7$ | G6 |
| 236 | O | N | $CR^7$ | G7 |
| 237 | S | N | $CR^7$ | G1 |
| 238 | S | N | $CR^7$ | G2 |
| 239 | S | N | $CR^7$ | G3 |
| 240 | S | N | $CR^7$ | G4 |

TABLE 10-continued

| Embodiment | $A^1$ | $A^2$ | $A^3$ | G |
|---|---|---|---|---|
| 241 | S | N | $CR^7$ | G5 |
| 242 | S | N | $CR^7$ | G6 |
| 243 | S | N | $CR^7$ | G7 |

In the formula (1A), compounds wherein $R^5$ is a methyl group, $R^6$ and $R^7$ are a hydrogen atom, and $A^1$, $A^2$, $A^3$ and G are as in the combinations of [Table 1] to [Table 10];
In the formula (1A), compounds wherein
$R^1$ is a C1 to C6 alkyl group optionally having one or more atoms or groups selected from the group consisting of halogen atoms and cyclopropyl groups, wherein the cyclopropyl group optionally has one or more halogen atoms or one or more C1 to C3 alkyl groups, a C2 to C6 alkenyl group optionally having one or more halogen atoms, a C2 to C6 alkynyl group optionally having one or more halogen atoms, or a C3 to C6 cycloalkyl group optionally having one or more atoms or groups selected from the group consisting of halogen atoms and C1 to C6 alkyl groups optionally having one or more halogen atoms,
$R^2$ is a halogen atom or a hydrogen atom,
$R^3$ and $R^4$ are the same or different and are a C1 to C6 chain hydrocarbon group optionally having one or more atoms or groups selected from group U, $OR^8$, $S(O)_m R^8$, a halogen atom, or a hydrogen atom,
$R^5$ is a C1 to C6 chain hydrocarbon group optionally having one or more atoms or groups selected from group X, $CO_2 R^8$, $C(O)R^3$, a C3 to C9 alicyclic hydrocarbon group optionally having one or more atoms or groups selected from group V, or a hydrogen atom, and
$A^1$, $A^2$, $A^3$ and G are as in the combinations of [Table 1] to [Table 10];
In the formula (1A), compounds wherein
$R^1$ is a methyl group, an ethyl group, a propyl group, a trifluoromethyl group, a 2,2,2-trifluoroethyl group, a cyclopropylmethyl group, or a cyclopropyl group,
$R^2$ is a hydrogen atom,
$R^3$ and $R^4$ are the same or different and are a C1 to C6 chain hydrocarbon group having one or more halogen atoms, $OR^3$, wherein
$R^8$ represents a C1 to C6 chain hydrocarbon group having one or more halogen atoms, or $S(O)_m R^8$, wherein $R^8$ represents a C1 to C6 chain hydrocarbon group having one or more halogen atoms, a halogen atom, or a hydrogen atom,
$R^5$ is a C1 to C6 alkyl group optionally having one or more halogen atoms or a hydrogen atom,
$R^6$ and $R^7$ are a hydrogen atom, and
$A^1$, $A^2$, $A^3$ and G are as in the combinations of [Table 1] to [Table 10];
In the formula (1A), compounds wherein
$R^1$ is an ethyl group,
$R^2$ is a hydrogen atom,
$R^3$ is a C1 to C3 perfluoroalkyl group, a C1 to C3 perfluoroalkylsulfanyl group, a C1 to C3 perfluoroalkylsulfinyl group, or a C1 to C3 perfluoroalkylsulfonyl group,
$R^4$ is a hydrogen atom, and
$A^1$, $A^2$, $A^3$ and G are as in the combinations of [Table 1] to [Table 10];
In the formula (1B), compounds wherein $A^1$, $A^2$, $A^3$ and G are as in the combinations of [Table 1] to [Table 10]
In the formula (1B), compounds wherein $R^5$ is a methyl group, $R^6$ and $R^7$ are a hydrogen atom, and $A^1$, $A^2$, $A^3$ and G are as in the combinations of [Table 1] to [Table 10];
In the formula (1B), compounds wherein $R^5$ is a methyl group, $R^6$ and $R^7$ are a hydrogen atom, and $A^1$, $A^2$, $A^3$ and G are as in the combinations of [Table 1] to [Table 10];
In the formula (1B), compounds wherein
$R^1$ is a C1 to C6 alkyl group optionally having one or more atoms or groups selected from the group consisting of halogen atoms and cyclopropyl groups, wherein the cyclopropyl group optionally has one or more halogen atoms or one or more C1 to C3 alkyl groups, a C2 to C6 alkenyl group optionally having one or more halogen atoms, a C2 to C6 alkynyl group optionally having one or more halogen atoms, or a C3 to C6 cycloalkyl group optionally having one or more atoms or groups selected from the group consisting of halogen atoms and C1 to C6 alkyl groups optionally having one or more halogen atoms,
$R^2$ is a halogen atom or a hydrogen atom,
$R^3$ and $R^4$ are the same or different and are a C1 to C6 chain hydrocarbon group optionally having one or more atoms or groups selected from group U, $OR^8$, $S(O)_m R^8$, a halogen atom, or a hydrogen atom,
$R^5$ is a C1 to C6 chain hydrocarbon group optionally having one or more atoms or groups selected from group X, $CO_2 R^8$, $C(O)R^8$, a C3 to C9 alicyclic hydrocarbon group optionally having one or more atoms or groups selected from group V, or a hydrogen atom, and
$A^1$, $A^2$, $A^3$ and G are as in the combinations of [Table 1] to [Table 10];
In the formula (1B), compounds wherein
$R^1$ is a methyl group, an ethyl group, a propyl group, a trifluoromethyl group, a 2,2,2-trifluoroethyl group, a cyclopropylmethyl group, or a cyclopropyl group,
$R^2$ is a hydrogen atom,
$R^3$ and $R^4$ are the same or different and are a C1 to C6 chain hydrocarbon group having one or more halogen atoms, $OR^8$, wherein $R^8$ represents a C1 to C6 chain hydrocarbon group having one or more halogen atoms, or $S(O)_m R^8$, wherein $R^8$ represents a C1 to C6 chain hydrocarbon group having one or more halogen atoms, a halogen atom, or a hydrogen atom,
$R^5$ is a C1 to C6 alkyl group optionally having one or more halogen atoms or a hydrogen atom,
$R^6$ and $R^7$ are a hydrogen atom, and
$A^1$, $A^2$, $A^3$ and G are as in the combinations of [Table 1] to [Table 10];
In the formula (1B), compounds wherein
$R^1$ is an ethyl group,
$R^2$ is a hydrogen atom,
$R^3$ is a C1 to C3 perfluoroalkyl group, a C1 to C3 perfluoroalkylsulfanyl group, a C1 to C3 perfluoroalkylsulfinyl group, or a C1 to C3 perfluoroalkylsulfonyl group,
$R^4$ is a hydrogen atom, and
$A^1$, $A^2$, $A^3$ and G are as in the combinations of [Table 1] to [Table 10];
In the formula (1C), compounds wherein $A^1$, $A^2$, $A^3$ and G are as in the combinations of [Table 1] to [Table 10];
In the formula (1C), compounds wherein $R^5$ is a methyl group, $R^6$ and $R^7$ are a hydrogen atom, and $A^1$, $A^2$, $A^3$ and G are as in the combinations of [Table 1] to [Table 10];
In the formula (1C), compounds wherein
$R^1$ is a C1 to C6 alkyl group optionally having one or more atoms or groups selected from the group consisting of halogen atoms and cyclopropyl groups, wherein the cyclopropyl group optionally has one or more halogen atoms or one or more C1 to C3 alkyl groups, a C2 to C6 alkenyl group optionally having one or more halogen atoms, a C2 to C6 alkynyl group optionally having one or more halogen atoms, or a C3 to C6 cycloalkyl group optionally having one or more atoms or groups selected from the group consisting of halogen atoms and C1 to C6 alkyl groups optionally having one or more halogen atoms, $R^2$ is a halogen atom or a hydrogen atom, $R^3$ and $R^4$ are the same or different and are a C1 to C6 chain hydrocarbon group optionally having one or more atoms or groups selected from group U, $OR^E$, $S(O)_mR^8$, a halogen atom, or a hydrogen atom, $R^5$ is a C1 to C6 chain hydrocarbon group optionally having one or more atoms or groups selected from group X, —$CO_2R^8$, —$C(O)R^8$, a C3 to C9 alicyclic hydrocarbon group optionally having one or more atoms or groups selected from group V, or a hydrogen atom, and $A^1$, $A^2$, $A^3$ and G are as in the combinations of [Table 1] to [Table 10];

In the formula (1C), compounds wherein $R^1$ is a methyl group, an ethyl group, a propyl group, a trifluoromethyl group, a 2,2,2-trifluoroethyl group, a cyclopropylmethyl group, or a cyclopropyl group, $R^2$ is a hydrogen atom, $R^3$ and $R^4$ are the same or different and are a C1 to C6 chain hydrocarbon group having one or more halogen atoms, $OR^8$, wherein $R^8$ represents a C1 to C6 chain hydrocarbon group having one or more halogen atoms, or $S(O)_mR^8$, wherein $R^8$ represents a C1 to C6 chain hydrocarbon group having one or more halogen atoms, a halogen atom, or a hydrogen atom, $R^5$ is a C1 to C6 alkyl group optionally having one or more halogen atoms or a hydrogen atom, $R^6$ and $R^7$ are a hydrogen atom, and $A^1$, $A^2$, $A^3$ and G are as in the combinations of [Table 1] to [Table 10];

In the formula (1C), compounds wherein $R^1$ is an ethyl group, $R^2$ is a hydrogen atom, $R^3$ is a C1 to C3 perfluoroalkyl group, a C1 to C3 perfluoroalkylsulfanyl group, a C1 to C3 perfluoroalkylsulfinyl group, or a C1 to C3 perfluoroalkylsulfonyl group, $R^4$ is a hydrogen atom, and $A^1$, $A^2$, $A^3$ and G are as in the combinations of [Table 1] to [Table 10].

Next, the method for producing the compound of the present invention will be described.

The compound of the present invention and the intermediate compound can be produced, for example, according to the following (Production Method 1) to (Production Method 7).

(Production Method 1)

The compound of the present invention (1-G1) in which G is G1 in the formula (1) can be produced by reacting intermediate compound (M1) with compound (M2), compound (M3) or compound (M4).

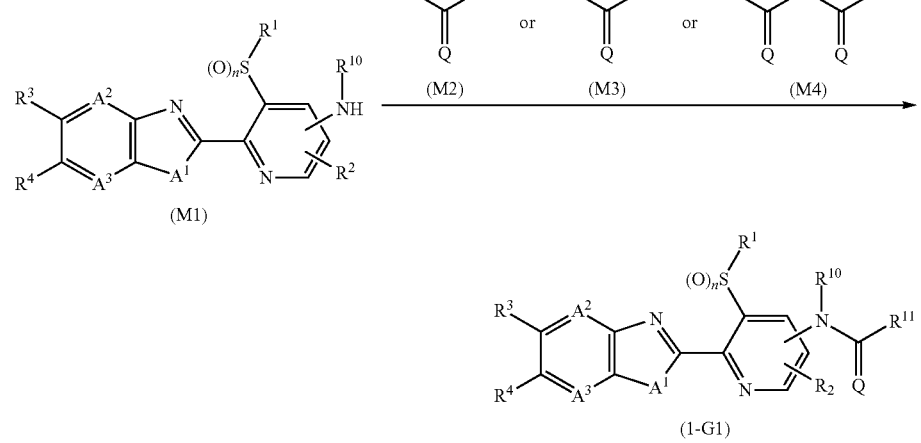

In the formula, symbols represent the same meaning as in the formula (1).

The compound of the present invention (1-G1) can be produced by reacting the intermediate compound (M1) with the compound (M2).

The reaction is usually carried out in the presence of a solvent. Examples of the solvent used in the reaction include ethers such as 1,4-dioxane, diethyl ether, tetrahydrofuran (hereinafter, referred to as THF) and tert-butyl methyl ether, halogenated hydrocarbons such as dichloromethane, chloroform, carbon tetrachloride, 1,2-dichloroethane and chlorobenzene, aromatic hydrocarbons such as toluene, benzene and xylene, esters such as ethyl acetate and butyl acetate, nitriles such as acetonitrile, aprotic polar solvents such as N,N-dimethylformamide (hereinafter, referred to as DMF), N-methyl pyrrolidone (hereinafter, referred to as NMP), 1,3-dimethyl-2-imidazolidinone and dimethyl sulfoxide (hereinafter, referred to as DMSO), nitrogen-containing aromatic compounds such as pyridine and quinolone, and mixtures thereof.

Examples of the condensing agent used in the reaction include carbodiimides such as 1-ethyl-3-(3-dimethylaminopropyl)carbodiimide hydrochloride (hereinafter, referred to as EDCI hydrochloride) and 1,3-dicyclohexylcarbodiimide.

The reaction can be also carried out by adding a catalyst, as necessary.

Examples of the catalyst used in the reaction include 1-hydroxybenzotriazole (hereinafter, referred to as HOBt).

In the reaction, the compound (M2) is usually used in a ratio of 1 to 2 mol, the condensing agent is usually used in a ratio of 1 to 5 mol, and the catalyst is usually used in a ratio of 0.01 to 1 mol, based on 1 mol of the intermediate compound (M1).

The reaction temperature in the reaction is usually in the range of 0 to 120° C. The reaction time in the reaction is usually within the range of 0.1 to 24 hours.

After completion of the reaction, the compound of the present invention (1-G1) can be isolated by adding the reaction mixture to water, then extracting the mixture with an organic solvent, and concentrating the organic layer; collecting by filtration a solid generated by adding the reaction mixture to water; or collecting by filtration a solid generated in the reaction mixture. The isolated compound of the present invention (1-G1) also can be further purified by recrystallization, chromatography, or the like.

The compound of the present invention (1-G1) can be produced by reacting the intermediate compound (M1) with the compound (M3) or the compound (M4).

The reaction is usually carried out in the presence of a solvent.

Examples of the solvent used in the reaction include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP and DMSO, and mixtures thereof.

The reaction can be also carried out by adding a base, as necessary.

The base used in the reaction includes alkali metal carbonates such as sodium carbonate and potassium carbonate, tertiary amines such as triethylamine and N,N-diisopropyl-ethylamine, nitrogen-containing aromatic compounds such as pyridine, 4-dimethylaminopyridine, and the like.

In the reaction, the compound (M3) or the compound (M4) is usually used in a ratio of 1 to 2 mol, and the base is usually used in a ratio of 1 to 5 mol, based on 1 mol of the intermediate compound (M1).

The reaction temperature in the reaction is usually in the range of −20 to 100° C. The reaction time in the reaction is usually in the range of 0.1 to 24 hours.

After completion of the reaction, the reaction mixture is subjected to the reaction mixture is subjected to post-treatment operations such as adding water to the reaction mixture, extracting the reaction mixture with an organic solvent, and drying and concenting the organic layer, whereby the compound of the present invention (1-G1) can be isolated. The isolated Compound of Present Invention (1-G1) also can be further purified by chromatography, recrystallization, or the like.

(Production Method 2)

The compound of the present invention (1-G2) in which G is G2 in the formula (1) can be produced by reacting intermediate compound (M5) with compound (M6) or compound (M7).

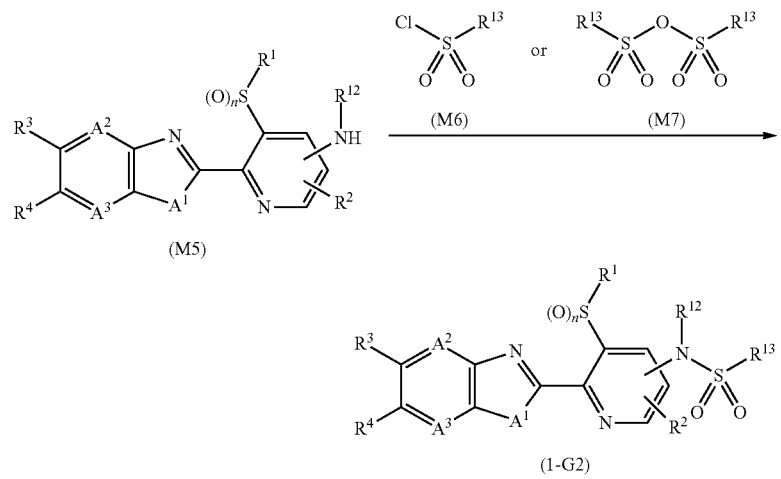

In the formula, symbols represent the same meaning as in the formula (1).

The reaction is usually carried out in the presence of a solvent.

Examples of the solvent used in the reaction include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP and DMSO, and mixtures thereof.

The reaction can be also carried out by adding a base, as necessary.

The base used in the reaction includes alkali metal carbonates such as sodium carbonate and potassium carbonate, tertiary amines such as triethylamine and N,N-diisopropyl-ethylamine, nitrogen-containing aromatic compounds such as pyridine, 4-dimethylaminopyridine, and the like.

In the reaction, the compound (M6) or the compound (M7) is usually used in a ratio of 1 to 2 mol, and the base is usually used in a ratio of 1 to 5 mol, based on 1 mol of the intermediate compound (M5).

The reaction temperature in the reaction is usually in the range of −20 to 100° C. The reaction time in the reaction is usually in the range of 0.1 to 24 hours.

After completion of the reaction, the reaction mixture is subjected to post-treatment operations such as adding water to the reaction mixture, extracting the reaction mixture with an organic solvent, and drying and concenting the organic layer, whereby the compound of the present invention (1-G2) can be isolated. The isolated Compound of Present Invention (1-G2) also can be further purified by chromatography, recrystallization, or the like.

(Production Method 3)

The compound of the present invention (1-G3) in which G is G3 in the formula (1) can be produced by reacting intermediate compound (M8) with compound (M9).

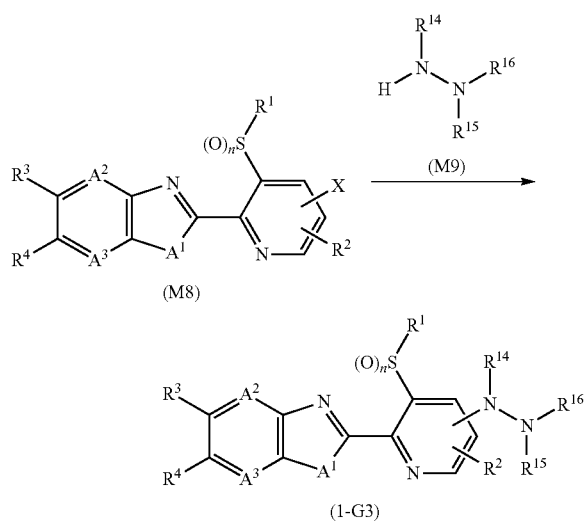

(M8)

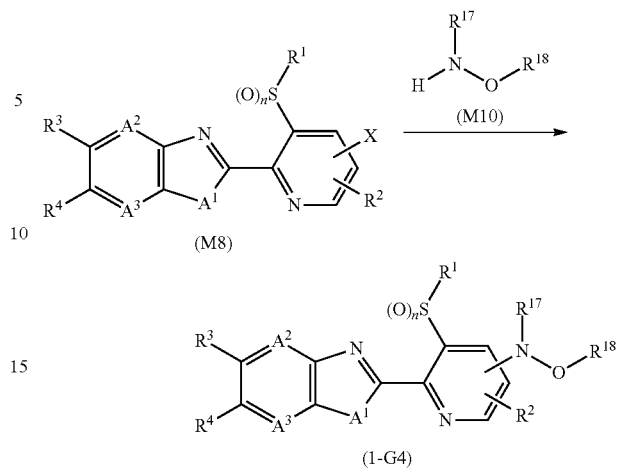

(M8)

(1-G3)

In the formula, X represents a fluorine atom, a chlorine atom, a bromine atom or an iodine atom, and other symbols represent the same meaning as in the formula (1).

The reaction is usually carried out in the presence of a solvent.

Examples of the solvent used in the reaction include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP and DMSO, and mixtures thereof.

The reaction can be also carried out by adding a base, as necessary.

The base used in the reaction includes inorganic bases such as tripotassium phosphate, potassium carbonate and sodium hydride, tertiary amines such as triethylamine and N,N-diisopropylethylamine, nitrogen-containing aromatic compounds such as pyridine, 4-dimethylaminopyridine, and the like.

In the reaction, the compound (M9) is usually used in a ratio of 1 to 5 mol, and the base is usually used in a ratio of 1 to 5 mol, based on 1 mol of the intermediate compound (M8).

The reaction temperature in the reaction is usually in the range of 0 to 150° C. The reaction time in the reaction is usually in the range of 0.1 to 24 hours.

After completion of the reaction, the reaction mixture is subjected to post-treatment operations such as adding water to the reaction mixture, extracting the reaction mixture with an organic solvent, and drying and concenting the organic layer, whereby the compound of the present invention (1-G3) can be isolated. The isolated Compound of Present Invention (1-G3) also can be further purified by chromatography, recrystallization, or the like.

(Production Method 4)

The compound of the present invention (1-G4) in which G is G4 in the formula (1) can be produced by reacting intermediate compound (M8) with compound (M10).

(1-G4)

In the formula, symbols represent the same meaning as described above.

The compound of the present invention (1-G4) can be produced, using the compound (M10), in place of the compound (M9), in accordance with the method described in Production Method 3.

(Production Method 5)

The compound of the present invention (1-G5) in which G is G5 in the formula (1) can be produced by reacting intermediate compound (M11) with compound (M12).

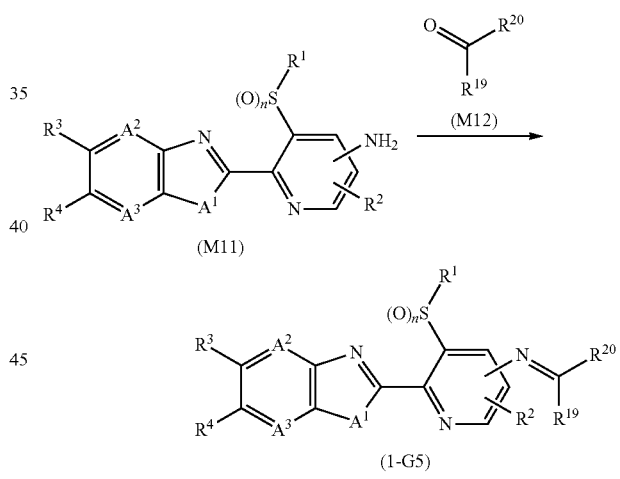

(M11)

(1-G5)

In the formula, symbols represent the same meaning as in the formula (1).

The reaction is carried out in the presence of a solvent, or the compound (M12) is used as as a solvent.

Examples of the solvent used in the reaction include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP and DMSO, and mixtures thereof.

The reaction can be also carried out by adding a dehydrating agent, as necessary.

The dehydrating agent used in the reaction includes mineral acids such as hydrochloric acid, and sulfonic acids such as p-toluenesulfonic acid.

In the reaction, the compound (M12) is usually used in a ratio of 1 to 5 mol, and the dehydrating agent is usually used in a ratio of 0.1 to 2 mol, based on 1 mol of the intermediate compound (M11).

The reaction temperature in the reaction is usually in the range of 0 to 150° C. The reaction time in the reaction is usually in the range of 0.1 to 24 hours.

After completion of the reaction, the reaction mixture is subjected to post-treatment operations such as adding water to the reaction mixture, extracting the reaction mixture with an organic solvent, and drying and concenting the organic layer, whereby the compound of the present invention (1-G5) can be isolated. The isolated Compound of Present Invention (1-G5) also can be further purified by chromatography, recrystallization, or the like.

(Production Method 6)

The compound of the present invention (1-J26) in which G is G6 and p is 0 in the formula (1) can be produced by reacting intermediate compound (M11) with compound (M13), in the presence of an oxidizing agent. The compound of the present invention (1-J27) in which G is G6 and p is 1 in the formula (1) can be produced by oxidizing the compound of the present invention (1-J26)

Examples of the oxidizing agent used in the reaction include halogenating agents such as N-chlorosuccinimide and hypervalent iodine compounds such as iodobenzene diacetate.

In the reaction, the compound (M13) is usually used in a ratio of 1 to 5 mol, and the oxidizing agent is usually used in a ratio of 1 to 5 mol, based on 1 mol of the intermediate compound (M11).

The reaction temperature in the reaction is usually in the range of 0 to 150° C. The reaction time in the reaction is usually in the range of 0.1 to 24 hours.

After completion of the reaction, the reaction mixture is subjected to post-treatment operations such as adding water to the reaction mixture, extracting the reaction mixture with an organic solvent, and drying and concenting the organic layer, whereby the compound of the present invention (1-J26) can be isolated. The isolated compound of the present invention (1-J26) also can be further purified by chromatography, recrystallization, or the like.

The compound of the present invention (1-J27) in which G is G6 and p is 1 in the formula (1) can be produced by oxidizing the compound of the present invention (1-J26).

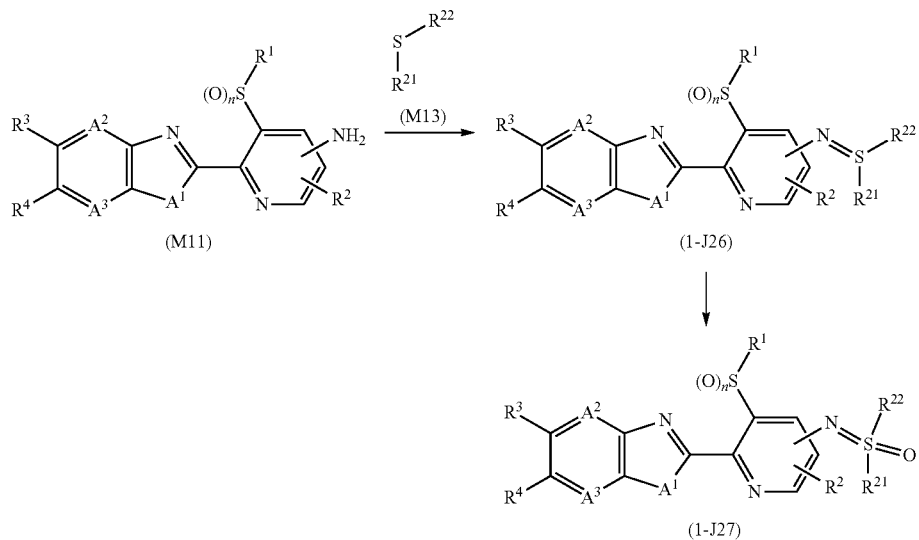

In the formula, symbols represent the same meaning as in the formula (1).

The compound of the present invention (1-J26) can be produced by reacting the intermediate compound (M11) with the compound (M13), in the presence of an oxidizing agent.

The reaction is usually carried out in the presence of a solvent.

Examples of the solvent used in the reaction include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP and DMSO, alcohols such as methanol and ethanol, water, and mixtures thereof.

The reaction is usually carried out in the presence of a solvent.

Examples of the solvent used in the reaction include aliphatic halogenated hydrocarbons such as dichloromethane and chloroform, alcohols such as methanol and ethanol, acetic acid, water, and mixtures thereof.

Examples of the oxidizing agent used in the reaction include sodium periodate and m-chloroperbenzoic acid.

In the reaction, the oxidizing agent is usually used in a ratio of 1 to 3 mol, based on 1 mol of the compound of the present invention (1-J26).

The reaction temperature in the reaction is usually in the range of −50 to 50° C. The reaction time in the reaction is usually in the range of 0.1 to 12 hours.

After completion of the reaction, the reaction mixture is subjected to post-treatment operations such as extracting the reaction mixture with an organic solvent, washing the organic layer with an aqueous solution of a reducing agent (for example, sodium sulfite, sodium thiosulfate) and an aqueous solution of a base (for example, sodium bicarbonate) as necessary, and drying and concenting the organic layer, whereby the compound of the present invention (1-J27) can be isolated. The isolated compound of the present invention (1-J27) also can be further purified by chromatography, recrystallization, or the like.

(Production Method 7)

The compound of the present invention (1-G7) in which G is G7 in the formula (1) can be produced by reacting intermediate compound (M8) with compound (M14).

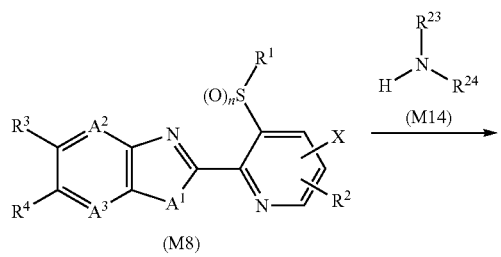

In the formula, symbols represent the same meaning as described above.

The compound of the present invention (1-G7) can be produced, using the compound (M14), in place of the compound (M9), in accordance with the method described in Production Method 3.

(Production Method 8)

The intermediate compound (M8) can be synthesized, for example, by the method described in Patent Document 1 (WO2013/018928).

The intermediate compound (M1) can be produced by reacting the intermediate compound (M8) with the compound (M15).

The intermediate compound (M5) can be produced by reacting the intermediate compound (M8) with the compound (M16).

The intermediate compound (M11) can be produced by reacting the intermediate compound (M8) with sodium azide to produce intermediate compound (M17), then reducing the intermediate compound (M17).

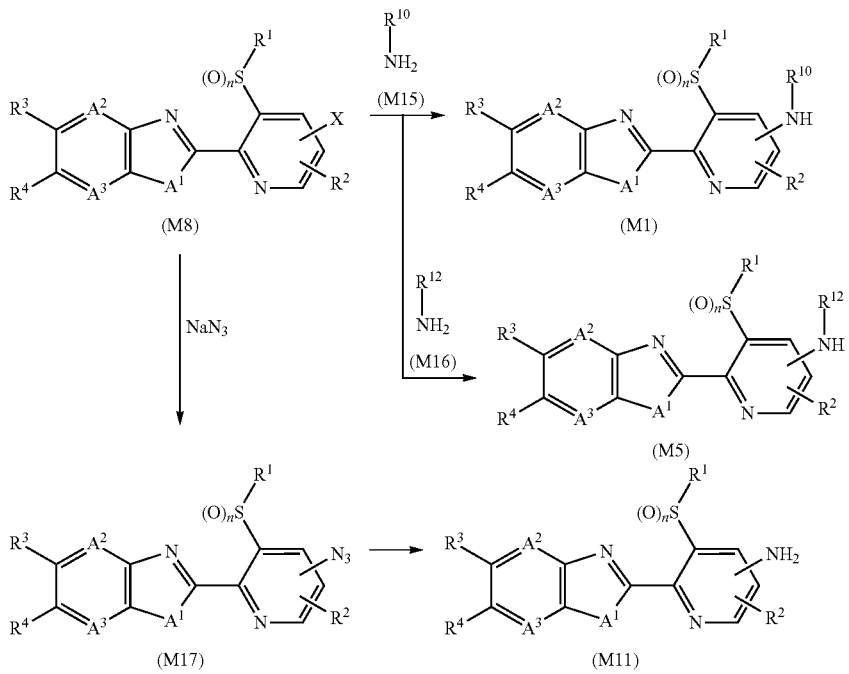

-continued

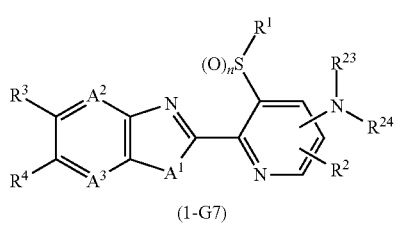

In the formula, symbols represent the same meaning as in the formula (1).

The intermediate compound (M1) can be produced, using the compound (M15), in place of the compound (M9), in accordance with the method of Production Method 3.

The intermediate compound (M5) can be produced, using the compound (M16), in place of the compound (M9), in accordance with the method of Production Method 3.

The intermediate compound (M17) can be produced by reacting the intermediate compound (M8) with sodium azide. The reaction is usually carried out in the presence of a solvent.

Examples of the solvent used in the reaction include ethers such as THF, ethylene glycol dimethyl ether, tert-butyl methyl ether and 1,4-dioxane, aprotic polar solvents such as DMF, NMP and DMSO, alcohols such as methanol and ethanol, water, and mixtures thereof.

In the reaction, sodium azide is usually used in a ratio of 1 to 5 mol, based on 1 mol of the intermediate compound (M8).

The reaction temperature in the reaction is usually in the range of 0 to 150° C. The reaction time in the reaction is usually in the range of 0.1 to 24 hours.

After completion of the reaction, the reaction mixture is subjected to post-treatment operations such as adding water to the reaction mixture, extracting the mixture with an organic solvent, and drying and concenting the organic layer, whereby the intermediate compound (M17) can be isolated. The intermediate compound (M11) can be produced by reducing the intermediate compound (M17).
The reaction is usually carried out in the presence of a solvent.

Examples of the solvent used in the reaction include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP and DMSO, alcohols such as methanol and ethanol, water, and mixtures thereof.

Examples of the reducing agent used in the reaction include phosphine compounds such as triphenylphosphine and tributylphosphine, tin(II) chloride, zinc, and the like. The reaction can be also carried out by adding an acid, as necessary.
Examples of the acid used in the reaction include mineral acids such as hydrochloric acid, carboxylic acids such as acetic acid.

In the reaction, the reducing agent is usually used in a ratio of 1 to 5 mol, and the acid is usually used in a ratio of 0.01 to 1 mol, based on 1 mol of the intermediate compound (M17).

The reaction temperature in the reaction is usually in the range of 0 to 150° C. The reaction time in the reaction is usually in the range of 0.1 to 24 hours.

After completion of the reaction, the reaction mixture is subjected to post-treatment operations such as adding water to the reaction mixture, extracting the mixture with an organic solvent, and drying and concenting the organic layer, whereby the intermediate compound (M11) can be isolated. The isolated intermediate compound (M11) also can be further purified by chromatography, recrystallization, or the like.

Next, specific examples of the compound of the present invention are shown below.
Compounds of the present invention, in the formula (1A),

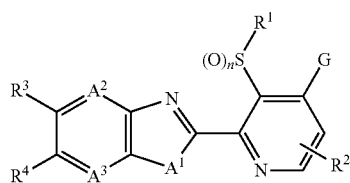

(1A)

wherein $R^1$ is an ethyl group, $R^2$ and $R^4$ are a hydrogen atom, $R^3$ is a trifluoromethyl group, n is 0, and $A^1$, $A^2$, $A^3$ and G are the combinations shown in [Table 11] to [Table 21];

TABLE 11

| Exemplification | $A^1$ | $A^2$ | $A^3$ | G |
|---|---|---|---|---|
| 1 | NCH$_3$ | CH | CH | NHC(O)CH$_2$Ph |
| 2 | NCH$_3$ | CH | CH | NHC(O)CycPr |
| 3 | NCH$_3$ | CH | CH | NHC(O)Ph |
| 4 | NCH$_3$ | CH | CH | NHC(O)(2-furyl) |
| 5 | NCH$_3$ | CH | CH | N(CycPr)C(O)CH$_3$ |
| 6 | NCH$_3$ | CH | CH | N{C(O)CH$_3$}$_2$ |
| 7 | NCH$_3$ | CH | CH | NHCO$_2$CH$_2$CycPr |
| 8 | NCH$_3$ | CH | CH | N(CycPr)CO$_2$CH$_3$ |
| 9 | NCH$_3$ | CH | CH | NHC(O)N(CH$_3$)$_2$ |
| 10 | NCH$_3$ | CH | CH | NHC(O)N(CH$_2$CH$_3$)$_2$ |
| 11 | NCH$_3$ | CH | CH | NCH$_3$C(O)N(CH$_3$)$_2$ |
| 12 | NCH$_3$ | CH | CH | NHC(O)C(O)OCH$_3$ |
| 13 | NCH$_3$ | CH | CH | NHC(O)CO$_2$CH$_2$CH$_3$ |
| 14 | NCH$_3$ | CH | CH | NHSO$_2$CH$_3$ |
| 15 | NCH$_3$ | CH | CH | NHSO$_3$CH$_3$ |
| 16 | NCH$_3$ | CH | CH | NHNHC(O)CH$_3$ |
| 17 | NCH$_3$ | CH | CH | NHNHCO$_2$CH$_3$ |
| 18 | NCH$_3$ | CH | CH | NHNHCO$_2$CH$_2$CH$_3$ |
| 19 | NCH$_3$ | CH | CH | N(CH$_3$)N(CH$_3$)CO$_2$CH$_3$ |
| 20 | NCH$_3$ | CH | CH | NHNHC(O)N(CH$_3$)$_2$ |
| 21 | NCH$_3$ | CH | CH | NHNHSO$_2$CH$_3$ |
| 22 | NCH$_3$ | CH | CH | N(CH$_3$)OCH$_3$ |
| 23 | NCH$_3$ | CH | CH | N(H)OCH$_3$ |
| 24 | NCH$_3$ | CH | CH | NHOC(O)CH$_3$ |
| 25 | NCH$_3$ | CH | CH | NHOCO$_2$CH$_3$ |

TABLE 12

| Exemplification | $A^1$ | $A^2$ | $A^3$ | G |
|---|---|---|---|---|
| 26 | NCH$_3$ | CH | CH | N=C(CH$_3$)$_2$ |
| 27 | NCH$_3$ | CH | CH | N=C(H)OCH$_3$ |
| 28 | NCH$_3$ | CH | CH | N=C(H)N(CH$_3$)$_2$ |
| 29 | NCH$_3$ | CH | CH | N=S(CH$_3$)$_2$ |
| 30 | NCH$_3$ | CH | CH | N=S(O)(CH$_3$)$_2$ |
| 31 | NCH$_3$ | CH | CH | NHBn |
| 32 | NCH$_3$ | CH | CH | NHCH$_2$(2-furyl) |
| 33 | NCH$_3$ | CH | CH | NHCycPr |
| 34 | NCH$_3$ | CH | CH | N(CH$_3$)CycPr |
| 35 | NCH$_3$ | CH | N | NHC(O)CH$_2$Ph |
| 36 | NCH$_3$ | CH | N | NHC(O)CycPr |
| 37 | NCH$_3$ | CH | N | NHC(O)Ph |
| 38 | NCH$_3$ | CH | N | NHC(O)(2-furyl) |
| 39 | NCH$_3$ | CH | N | N(CycPr)C(O)CH$_3$ |
| 40 | NCH$_3$ | CH | N | N{C(O)CH$_3$}$_2$ |
| 41 | NCH$_3$ | CH | N | NHCO$_2$CH$_2$CycPr |
| 42 | NCH$_3$ | CH | N | N(CycPr)CO$_2$CH$_3$ |
| 43 | NCH$_3$ | CH | N | NHC(O)N(CH$_3$)$_2$ |
| 44 | NCH$_3$ | CH | N | NHC(O)N(CH$_2$CH$_3$)$_2$ |
| 45 | NCH$_3$ | CH | N | NCH$_3$C(O)N(CH$_3$)$_2$ |
| 46 | NCH$_3$ | CH | N | NHC(O)C(O)OCH$_3$ |
| 47 | NCH$_3$ | CH | N | NHC(O)CO$_2$CH$_2$CH$_3$ |
| 48 | NCH$_3$ | CH | N | NHSO$_2$CH$_3$ |
| 49 | NCH$_3$ | CH | N | NHSO$_3$CH$_3$ |
| 50 | NCH$_3$ | CH | N | NHNHC(O)CH$_3$ |

TABLE 13

| Exemplification | $A^1$ | $A^2$ | $A^3$ | G |
|---|---|---|---|---|
| 51 | NCH$_3$ | CH | N | NHNHCO$_2$CH$_3$ |
| 52 | NCH$_3$ | CH | N | NHNHCO$_2$CH$_2$CH$_3$ |
| 53 | NCH$_3$ | CH | N | N(CH$_3$)N(CH$_3$)CO$_2$CH$_3$ |
| 54 | NCH$_3$ | CH | N | NHNHC(O)N(CH$_3$)$_2$ |
| 55 | NCH$_3$ | CH | N | NHNHSO$_2$CH$_3$ |
| 56 | NCH$_3$ | CH | N | N(CH$_3$)OCH$_3$ |
| 57 | NCH$_3$ | CH | N | N(H)OCH$_3$ |
| 58 | NCH$_3$ | CH | N | NHOC(O)CH$_3$ |
| 59 | NCH$_3$ | CH | N | NHOCO$_2$CH$_3$ |
| 60 | NCH$_3$ | CH | N | N=C(CH$_3$)$_2$ |
| 61 | NCH$_3$ | CH | N | N=C(H)OCH$_3$ |
| 62 | NCH$_3$ | CH | N | N=C(H)N(CH$_3$)$_2$ |
| 63 | NCH$_3$ | CH | N | N=S(CH$_3$)$_2$ |

TABLE 13-continued

| Exemplification | A¹ | A² | A³ | G |
|---|---|---|---|---|
| 64 | NCH₃ | CH | N | N=S(O)(CH₃)₂ |
| 65 | NCH₃ | CH | N | NHBn |
| 66 | NCH₃ | CH | N | NHCH₂(2-furyl) |
| 67 | NCH₃ | CH | N | NHCycPr |
| 68 | NCH₃ | CH | N | N(CH₃)CycPr |
| 69 | O | CH | CH | NHC(O)CH₂Ph |
| 70 | O | CH | CH | NHC(O)CycPr |
| 71 | O | CH | CH | NHC(O)Ph |
| 72 | O | CH | CH | NHC(O)(2-furyl) |
| 73 | O | CH | CH | N(CycPr)C(O)CH₃ |
| 74 | O | CH | CH | N{C(O)CH₃}₂ |
| 75 | O | CH | CH | NHCO₂CH₂CycPr |

TABLE 14

| Exemplification | A¹ | A² | A³ | G |
|---|---|---|---|---|
| 76 | O | CH | CH | N(CycPr)CO₂CH₃ |
| 77 | O | CH | CH | NHC(O)N(CH₃)₂ |
| 78 | O | CH | CH | NHC(O)N(CH₂CH₃)₂ |
| 79 | O | CH | CH | NCH₃C(O)N(CH₃)₂ |
| 80 | O | CH | CH | NHC(O)C(O)OCH₃ |
| 81 | O | CH | CH | NHC(O)CO₂CH₂CH₃ |
| 82 | O | CH | CH | NHSO₂CH₃ |
| 83 | O | CH | CH | NHSO₃CH₃ |
| 84 | O | CH | CH | NHNHC(O)CH₃ |
| 85 | O | CH | CH | NHNHCO₂CH₃ |
| 86 | O | CH | CH | NHNHCO₂CH₂CH₃ |
| 81 | O | CH | CH | N(CH₃)N(CH₃)CO₂CH₃ |
| 88 | O | CH | CH | NHNHC(O)N(CH₃)₂ |
| 89 | O | CH | CH | NHNHSO₂CH₃ |
| 90 | O | CH | CH | N(CH₃)OCH₃ |
| 91 | O | CH | CH | N(H)OCH₃ |
| 92 | O | CH | CH | NHOC(O)CH₃ |
| 93 | O | CH | CH | NHOCO₂CH₃ |
| 94 | O | CH | CH | N=C(CH₃)₂ |
| 95 | O | CH | CH | N=CO(H)OCH₃ |
| 96 | O | CH | CH | N=C(H)N(CH₃)₂ |
| 97 | O | CH | CH | N=S(CH₃)₂ |
| 98 | O | CH | CH | N=S(O)(CH₃)₂ |
| 99 | O | CH | CH | NHBn |
| 100 | O | CH | CH | NHCH₂(2-furyl) |

TABLE 15

| Exemplification | A¹ | A² | A³ | G |
|---|---|---|---|---|
| 101 | O | CH | CH | NHCycPr |
| 102 | O | CH | CH | N(CH₃)CycPr |
| 103 | O | CH | N | NHC(O)CH₂Ph |
| 104 | O | CH | N | NHC(O)CycPr |
| 105 | O | CH | N | NHC(O)Ph |
| 106 | O | CH | N | NHC(O)(2-furyl) |
| 107 | O | CH | N | N(CycPr)C(O)CH₃ |
| 108 | O | CH | N | N{C(O)CH₃}₂ |
| 109 | O | CH | N | NHCO₂CH₂CycPr |
| 110 | O | CH | N | N(CycPr)CO₂CH₃ |
| 111 | O | CH | N | NHC(O)N(CH₃)₂ |
| 112 | O | CH | N | NHC(O)N(CH₂CH₃)₂ |
| 113 | O | CH | N | NCH₃C(O)N(CH₃)₂ |
| 114 | O | CH | N | NHC(O)C(O)OCH₃ |
| 115 | O | CH | N | NHC(O)CO₂CH₂CH₃ |
| 116 | O | CH | N | NHSO₂CH₃ |
| 117 | O | CH | N | NHSO₃CH₃ |
| 118 | O | CH | N | NHNHC(O)CH₃ |
| 119 | O | CH | N | NHNHCO₂CH₃ |
| 120 | O | CH | N | NHNHCO₂CH₂CH₃ |
| 121 | O | CH | N | N(CH₃)N(CH₃)CO₂CH₃ |
| 122 | O | CH | N | NHNHC(O)N(CH₃)₂ |
| 123 | O | CH | N | NHNHSO₂CH₃ |
| 124 | O | CH | N | N(CH₃)OCH₃ |
| 125 | O | CH | N | N(H)OCH₃ |

TABLE 16

| Exemplification | A¹ | A² | A³ | G |
|---|---|---|---|---|
| 126 | O | CH | N | NHOC(O)CH₃ |
| 127 | O | CH | N | NHOCO₂CH₃ |
| 128 | O | CH | N | N=C(CH₃)₂ |
| 129 | O | CH | N | N=C(H)OCH₃ |
| 130 | O | CH | N | N=C(H)N(CH₃)₂ |
| 131 | O | CH | N | N=S(CH₃)₂ |
| 132 | O | CH | N | N=S(O)(CH₃)₂ |
| 133 | O | CH | N | NHBn |
| 134 | O | CH | N | NHCH₂(2-furyl) |
| 135 | O | CH | N | NHCycPr |
| 136 | O | CH | N | N(CH₃)CycPr |
| 137 | S | CH | CH | NHC(O)CH₂Ph |
| 138 | S | CH | CH | NHC(O)CycPr |
| 139 | S | CH | CH | NHC(O)Ph |
| 140 | S | CH | CH | NHC(O)(2-furyl) |
| 141 | S | CH | CH | N(CycPr)C(O)CH₃ |
| 142 | S | CH | CH | N{C(O)CH₃}₂ |
| 143 | S | CH | CH | NHCO₂CH₂CycPr |
| 144 | S | CH | CH | N(CycPr)CO₂CH₃ |
| 145 | S | CH | CH | NHC(O)N(CH₃)₂ |
| 146 | S | CH | CH | NHC(O)N(CH₂CH₃)₂ |
| 147 | S | CH | CH | NCH₃C(O)N(CH₃)₂ |
| 148 | S | CH | CH | NHC(O)C(O)OCH₃ |
| 149 | S | CH | CH | NHC(O)CO₂CH₂CH₃ |
| 150 | S | CH | CH | NHSO₂CH₃ |

TABLE 17

| Exemplification | A¹ | A² | A³ | G |
|---|---|---|---|---|
| 151 | S | CH | CH | NHSO₃CH₃ |
| 152 | S | CH | CH | NHNHC(O)CH₃ |
| 153 | S | CH | CH | NHNHCO₂CH₃ |
| 154 | S | CH | CH | NHNHCO₂CH₂CH₃ |
| 155 | S | CH | CH | N(CH₃)N(CH₃)CO₂CH₃ |
| 156 | S | CH | CH | NHNHC(O)N(CH₃)₂ |
| 157 | S | CH | CH | NHNHSO₂CH₃ |
| 158 | S | CH | CH | N(CH₃)OCH₃ |
| 159 | S | CH | CH | N(H)OCH₃ |
| 160 | S | CH | CH | NHOC(O)CH₃ |
| 161 | S | CH | CH | NHOCO₂CH₃ |
| 162 | S | CH | CH | N=C(CH₃)₂ |
| 163 | S | CH | CH | N=C(H)OCH₃ |
| 164 | S | CH | CH | N=C(H)N(CH₃)₂ |
| 165 | S | CH | CH | N=S(CH₃)₂ |
| 166 | S | CH | CH | N=S(O)(CH₃)₂ |
| 167 | S | CH | CH | NHBn |
| 168 | S | CH | CH | NHCH₂(2-furyl) |
| 169 | S | CH | CH | NHCycPr |
| 170 | S | CH | CH | N(CH₃)CycPr |
| 171 | S | CH | N | NHC(O)CH₂Ph |
| 172 | S | CH | N | NHC(O)CycPr |
| 173 | S | CH | N | NHC(O)Ph |
| 174 | S | CH | N | NHC(O)(2-furyl) |
| 175 | S | CH | N | N(CycPr)C(O)CH₃ |

TABLE 18

| Exemplification | A¹ | A² | A³ | G |
|---|---|---|---|---|
| 176 | S | CH | N | N{C(O)CH₃}₂ |
| 177 | S | CH | N | NHCO₂CH₂CycPr |
| 178 | S | CH | N | N(CycPr)CO₂CH₃ |
| 179 | S | CH | N | NHC(O)N(CH₃)₂ |
| 180 | S | CH | N | NHC(O)N(CH₂CH₃)₂ |
| 181 | S | CH | N | NCH₃C(O)N(CH₃)₂ |
| 182 | S | CH | N | NHC(O)C(O)OCH₃ |
| 183 | S | CH | N | NHC(O)CO₂CH₂CH₃ |
| 184 | S | CH | N | NHSO₂CH₃ |
| 185 | S | CH | N | NHSO₃CH₃ |
| 186 | S | CH | N | NHNHC(O)CH₃ |
| 187 | S | CH | N | NHNHCO₂CH₃ |
| 188 | S | CH | N | NHNHCO₂CH₂CH₃ |

TABLE 18-continued

| Exemplification | A¹ | A² | A³ | G |
|---|---|---|---|---|
| 189 | S | CH | N | N(CH₃)N(CH₃)CO₂CH₃ |
| 190 | S | CH | N | NHNHC(O)N(CH₃)₂ |
| 191 | S | CH | N | NHNHSO₂CH₃ |
| 192 | S | CH | N | N(CH₃)OCH₃ |
| 193 | S | CH | N | N(H)OCH₃ |
| 194 | S | CH | N | NHOC(O)CH₃ |
| 195 | S | CH | N | NHOCO₂CH₃ |
| 196 | S | CH | N | N=C(CH₃)₂ |
| 197 | S | CH | N | N=C(H)OCH₃ |
| 198 | S | CH | N | N=C(H)N(CH₃)₂ |
| 199 | S | CH | N | N=S(CH₃)₂ |
| 200 | S | CH | N | N=S(O)(CH₃)₂ |

TABLE 19

| Exemplification | A¹ | A² | A³ | G |
|---|---|---|---|---|
| 201 | S | CH | N | NHBn |
| 202 | S | CH | N | NHCH₂(2-furyl) |
| 203 | S | CH | N | NHCycPr |
| 204 | S | CH | N | N(CH₃)CycPr |
| 205 | NCH₃ | CH | CH | NHCH₂(2-chloro-thiazol-5-yl) |
| 206 | NCH₃ | CH | CH | NHCH₂(6-chloro-pyridin-3-yl) |
| 207 | NCH₃ | CH | CH | NHCH₂(tetrahydrofuran-2-yl) |
| 208 | NCH₃ | CH | CH | NHCH₂(tetrahydrofuran-2-yl) |
| 209 | NCH₃ | CH | CH | N(CH₃)CH₂(2-chloro-thiazol-5-yl) |
| 210 | NCH₃ | CH | CH | N(CH₃)CH₂(6-chloro-pyridin-3-yl) |
| 211 | NCH₃ | CH | CH | N(CH₃)CH₂(tetrahydrofuran-2-yl) |
| 212 | NCH₃ | CH | CH | N(CH₃)CH₂(tetrahydrofuran-2-yl) |
| 213 | NCH₃ | CH | N | NHCH₂(2-chloro-thiazol-5-yl) |
| 214 | NCH₃ | CH | N | NHCH₂(6-chloro-pyridin-3-yl) |
| 215 | NCH₃ | CH | N | NHCH₂(tetrahydrofuran-2-yl) |
| 216 | NCH₃ | CH | N | NHCH₂(tetrahydrofuran-2-yl) |
| 217 | NCH₃ | CH | N | N(CH₃)CH₂(2-chloro-thiazol-5-yl) |
| 218 | NCH₃ | CH | N | N(CH₃)CH₂(6-chloro-pyridin-3-yl) |
| 219 | NCH₃ | CH | N | N(CH₃)CH₂(tetrahydrofuran-2-yl) |
| 220 | NCH₃ | CH | N | N(CH₃)CH₂(tetrahydrofuran-2-yl) |
| 221 | O | CH | CH | NHCH₂(2-chloro-thiazol-5-yl) |
| 222 | O | CH | CH | NHCH₂(6-chloro-pyridin-3-yl) |
| 223 | O | CH | CH | NHCH₂(tetrahydrofuran-2-yl) |
| 224 | O | CH | CH | NHCH₂(tetrahydrofuran-2-yl) |
| 225 | O | CH | CH | N(CH₃)CH₂(2-chloro-thiazol-5-yl) |

TABLE 20

| Exemplification | A¹ | A² | A³ | G |
|---|---|---|---|---|
| 226 | O | CH | CH | N(CH₃)CH₂(6-chloro-pyridin-3-yl) |
| 227 | O | CH | CH | N(CH₃)CH₂(tetrahydrofuran-2-yl) |
| 228 | O | CH | CH | N(CH₃)CH₂(tetrahydrofuran-2-yl) |
| 229 | O | CH | N | NHCH₂(2-chloro-thiazol-5-yl) |
| 230 | O | CH | N | NHCH₂(6-chloro-pyridin-3-yl) |
| 231 | O | CH | N | NHCH₂(tetrahydrofuran-2-yl) |
| 232 | O | CH | N | NHCH₂(tetrahydrofuran-2-yl) |
| 233 | O | CH | N | N(CH₃)CH₂(2-chloro-thiazol-5-yl) |
| 234 | O | CH | N | N(CH₃)CH₂(6-chloro-pyridin-3-yl) |
| 235 | O | CH | N | N(CH₃)CH₂(tetrahydrofuran-2-yl) |
| 236 | O | CH | N | N(CH₃)CH₂(tetrahydrofuran-2-yl) |
| 237 | S | CH | CH | NHCH₂(2-chloro-thiazol-5-yl) |
| 238 | S | CH | CH | NHCH₂(6-chloro-pyridin-3-yl) |
| 239 | S | CH | CH | NHCH₂(tetrahydrofuran-2-yl) |
| 240 | S | CH | CH | NHCH₂(tetrahydrofuran-2-yl) |
| 241 | S | CH | CH | N(CH₃)CH₂(2-chloro-thiazol-5-yl) |
| 242 | S | CH | CH | N(CH₃)CH₂(6-chloro-pyridin-3-yl) |
| 243 | S | CH | CH | N(CH₃)CH₂(tetrahydrofuran-2-yl) |
| 244 | S | CH | CH | N(CH₃)CH₂(tetrahydrofuran-2-yl) |
| 245 | S | CH | N | NHCH₂(2-chloro-thiazol-53-yl) |
| 246 | S | CH | N | NHCH₂(6-chloro-pyridin-3-yl) |
| 247 | S | CH | N | NHCH₂(tetrahydrofuran-2-yl) |
| 248 | S | CH | N | NHCH₂(tetrahydrofuran-2-yl) |
| 249 | S | CH | N | N(CH₃)CH₂(2-chloro-thiazol-5-yl) |
| 250 | S | CH | N | N(CH₃)CH₂(6-chloro-pyridin-3-yl) |

TABLE 21

| Exemplification | A¹ | A² | A³ | G |
|---|---|---|---|---|
| 251 | S | CH | N | N(CH₃)CH₂(tetrahydrofuran-2-yl) |
| 252 | S | CH | N | N(CH₃)CH₂(tetrahydrofuran-2-yl) |

(In [Table 11] to [Table 21] above, CycPr represents a cyclopropyl group, Ph represents a phenyl group, 2-furyl represents a furyl-2-yl group, and Bn represents a benzyl group.)

Compounds of the present invention, in the formula (1A), wherein $R^1$ is an ethyl group, $R^2$ and $R^4$ are a hydrogen atom, $R^3$ is a trifluoromethyl group, n is 1, and $A^1$, $A^2$, $A^3$ and G are the combinations shown in [Table 11] to [Table 21];

Compounds of the present invention, in the formula (1A), wherein $R^1$ is an ethyl group, $R^2$ and $R^4$ are a hydrogen atom, $R^3$ is a trifluoromethyl group, n is 2, and $A^1$, $A^2$, $A^3$ and G are the combinations shown in [Table 11] to [Table 21];

Compounds of the present invention, in the formula (1A), wherein $R^1$ is an ethyl group, $R^2$ and $R^4$ are a hydrogen atom, $R^3$ is a pentafluoroethyl group, n is 0, and $A^1$, $A^2$, $A^3$ and G are the combinations shown in [Table 11] to [Table 21];

Compounds of the present invention, in the formula (1A), wherein $R^1$ is an ethyl group, $R^2$ and $R^4$ are a hydrogen atom, $R^3$ is a pentafluoroethyl group, n is 1, and $A^1$, $A^2$, $A^3$ and G are the combinations shown in [Table 11] to [Table 21];

Compounds of the present invention, in the formula (1A), wherein $R^1$ is an ethyl group, $R^2$ and $R^4$ are a hydrogen atom, $R^3$ is a pentafluoroethyl group, n is 2, and $A^1$, $A^2$, $A^3$ and G are the combinations shown in [Table 11] to [Table 21];

Compounds of the present invention, in the formula (1A), wherein $R^1$ is an ethyl group, $R^2$ and $R^4$ are a hydrogen atom, $R^3$ is a trifluoromethylsulfanyl group, n is 0, and $A^1$, $A^2$, $A^3$ and G are the combinations shown in [Table 11] to [Table 21];

Compounds of the present invention, in the formula (1A), wherein $R^1$ is an ethyl group, $R^2$ and $R^4$ are a hydrogen atom, $R^3$ is a trifluoromethylsulfanyl group, n is 1, and $A^1$, $A^2$, $A^3$ and G are the combinations shown in [Table 11] to [Table 21];

Compounds of the present invention, in the formula (1A), wherein $R^1$ is an ethyl group, $R^2$ and $R^4$ are a hydrogen atom, $R^3$ is a trifluoromethylsulfanyl group, n is 2, and $A^1$, $A^2$, $A^3$ and G are the combinations shown in [Table 11] to [Table 21];

Compounds of the present invention, in the formula (1A), wherein $R^1$ is an ethyl group, $R^2$ and $R^4$ are a hydrogen atom, $R^3$ is a trifluoromethylsulfinyl group, n is 0, and $A^1$, $A^2$, $A^3$ and G are the combinations shown in [Table 11] to [Table 21];

Compounds of the present invention, in the formula (1A), wherein $R^1$ is an ethyl group, $R^2$ and $R^4$ are a hydrogen atom, $R^3$ is a trifluoromethylsulfinyl group, n is 1, and $A^1$, $A^2$, $A^3$ and G are the combinations shown in [Table 11] to [Table 21];

Compounds of the present invention, in the formula (1A), wherein $R^1$ is an ethyl group, $R^2$ and $R^4$ are a hydrogen atom, $R^3$ is a trifluoromethylsulfinyl group, n is 2, and $A^1$, $A^2$, $A^3$ and G are the combinations shown in [Table 11] to [Table 21];

Compounds of the present invention, in the formula (1A), wherein $R^1$ is an ethyl group, $R^2$ and $R^4$ are a hydrogen atom, $R^3$ is a trifluoromethylsulfonyl group, n is 0, and $A^1$, $A^2$, $A^3$ and G are the combinations shown in [Table 11] to [Table 21];

Compounds of the present invention, in the formula (1A), wherein $R^1$ is an ethyl group, $R^2$ and $R^4$ are a hydrogen atom, $R^3$ is a trifluoromethylsulfonyl group, n is 1, and $A^1$, $A^2$, $A^3$ and G are the combinations shown in [Table 11] to [Table 21];

Compounds of the present invention, in the formula (1A), wherein $R^1$ is an ethyl group, $R^2$ and $R^4$ are a hydrogen atom, $R^3$ is a trifluoromethylsulfonyl group, n is 2, and $A^1$, $A^2$, $A^3$ and G are the combinations shown in [Table 11] to [Table 21];

Compounds of the present invention, in the formula (1B), wherein $R^1$ is an ethyl group, $R^2$ and $R^4$ are a hydrogen atom, $R^3$ is a trifluoromethyl group, n is 0, and $A^1$, $A^2$, $A^3$ and G are the combinations shown in [Table 11] to [Table 21];

Compounds of the present invention, in the formula (1B), wherein $R^1$ is an ethyl group, $R^2$ and $R^4$ are a hydrogen atom, $R^3$ is a trifluoromethyl group, n is 1, and $A^1$, $A^2$, $A^3$ and G are the combinations shown in [Table 11] to [Table 21];

Compounds of the present invention, in the formula (1B), wherein $R^1$ is an ethyl group, $R^2$ and $R^4$ are a hydrogen atom, $R^3$ is a trifluoromethyl group, n is 2, and $A^1$, $A^2$, $A^3$ and G are the combinations shown in [Table 11] to [Table 21];

Compounds of the present invention, in the formula (1B), wherein $R^1$ is an ethyl group, $R^2$ and $R^4$ are a hydrogen atom, $R^3$ is a pentafluoroethyl group, n is 0, and $A^1$, $A^2$, $A^3$ and G are the combinations shown in [Table 11] to [Table 21];

Compounds of the present invention, in the formula (1B), wherein $R^1$ is an ethyl group, $R^2$ and $R^4$ are a hydrogen atom, $R^3$ is a pentafluoroethyl group, n is 1, and $A^1$, $A^2$, $A^3$ and G are the combinations shown in [Table 11] to [Table 21];

Compounds of the present invention, in the formula (1B), wherein $R^1$ is an ethyl group, $R^2$ and $R^4$ are a hydrogen atom, $R^3$ is a pentafluoroethyl group, n is 2, and $A^1$, $A^2$, $A^3$ and G are the combinations shown in [Table 11] to [Table 21];

Compounds of the present invention, in the formula (1B), wherein $R^1$ is an ethyl group, $R^2$ and $R^4$ are a hydrogen atom, $R^3$ is a trifluoromethylsulfanyl group, n is 0, and $A^1$, $A^2$, $A^3$ and G are the combinations shown in [Table 11] to [Table 21];

Compounds of the present invention, in the formula (1B), wherein $R^1$ is an ethyl group, $R^2$ and $R^4$ are a hydrogen atom, $R^3$ is a trifluoromethylsulfanyl group, n is 1, and $A^1$, $A^2$, $A^3$ and G are the combinations shown in [Table 11] to [Table 21];

Compounds of the present invention, in the formula (1B), wherein $R^1$ is an ethyl group, $R^2$ and $R^4$ are a hydrogen atom, $R^3$ is a trifluoromethylsulfanyl group, n is 2, and $A^1$, $A^2$, $A^3$ and G are the combinations shown in [Table 11] to [Table 21];

Compounds of the present invention, in the formula (1B), wherein $R^1$ is an ethyl group, $R^2$ and $R^4$ are a hydrogen atom, $R^3$ is a trifluoromethylsulfinyl group, n is 0, and $A^1$, $A^2$, $A^3$ and G are the combinations shown in [Table 11] to [Table 21];

Compounds of the present invention, in the formula (1B), wherein $R^1$ is an ethyl group, $R^2$ and $R^4$ are a hydrogen atom, $R^3$ is a trifluoromethylsulfinyl group, n is 1, and $A^1$, $A^2$, $A^3$ and G are the combinations shown in [Table 11] to [Table 21];

Compounds of the present invention, in the formula (1B), wherein $R^1$ is an ethyl group, $R^2$ and $R^4$ are a hydrogen atom, $R^3$ is a trifluoromethylsulfinyl group, n is 2, and $A^1$, $A^2$, $A^3$ and G are the combinations shown in [Table 11] to [Table 21];

Compounds of the present invention, in the formula (1B), wherein $R^1$ is an ethyl group, $R^2$ and $R^4$ are a hydrogen atom, $R^3$ is a trifluoromethylsulfonyl group, n is 0, and $A^1$, $A^2$, $A^3$ and G are the combinations shown in [Table 11] to [Table 21];

Compounds of the present invention, in the formula (1B), wherein $R^1$ is an ethyl group, $R^2$ and $R^4$ are a hydrogen atom, $R^3$ is a trifluoromethylsulfonyl group, n is 1, and $A^1$, $A^2$, $A^3$ and G are the combinations shown in [Table 11] to [Table 21];

Compounds of the present invention, in the formula (1B), wherein $R^1$ is an ethyl group, $R^2$ and $R^4$ are a hydrogen atom, $R^3$ is a trifluoromethylsulfonyl group, n is 2, and $A^1$, $A^2$, $A^3$ and G are the combinations shown in [Table 11] to [Table 21];

Compounds of the present invention, in the formula (1C), wherein $R^1$ is an ethyl group, $R^2$ and $R^4$ are a hydrogen atom, $R^3$ is a trifluoromethyl group, n is 0, and $A^1$, $A^2$, $A^3$ and G are the combinations shown in [Table 11] to [Table 21];

Compounds of the present invention, in the formula (1C), wherein $R^1$ is an ethyl group, $R^2$ and $R^4$ are a hydrogen atom, $R^3$ is a trifluoromethyl group, n is 1, and $A^1$, $A^2$, $A^3$ and G are the combinations shown in [Table 11] to [Table 21];

Compounds of the present invention, in the formula (1C), wherein $R^1$ is an ethyl group, $R^2$ and $R^4$ are a hydrogen atom, $R^3$ is a trifluoromethyl group, n is 2, and $A^1$, $A^2$, $A^3$ and G are the combinations shown in [Table 11] to [Table 21];

Compounds of the present invention, in the formula (1C), wherein $R^1$ is an ethyl group, $R^2$ and $R^4$ are a hydrogen atom, $R^3$ is a pentafluoroethyl group, n is 0, and $A^1$, $A^2$, $A^3$ and G are the combinations shown in [Table 11] to [Table 21];

Compounds of the present invention, in the formula (1C), wherein $R^1$ is an ethyl group, $R^2$ and $R^4$ are a hydrogen atom, $R^3$ is a pentafluoroethyl group, n is 1, and $A^1$, $A^2$, $A^3$ and G are the combinations shown in [Table 11] to [Table 21];

Compounds of the present invention, in the formula (1C), wherein $R^1$ is an ethyl group, $R^2$ and $R^4$ are a hydrogen atom, $R^3$ is a pentafluoroethyl group, n is 2, and $A^1$, $A^2$, $A^3$ and G are the combinations shown in [Table 11] to [Table 21];

Compounds of the present invention, in the formula (1C), wherein $R^1$ is an ethyl group, $R^2$ and $R^4$ are a hydrogen atom, $R^3$ is a trifluoromethylsulfanyl group, n is 0, and $A^1$, $A^2$, $A^3$ and G are the combinations shown in [Table 11] to [Table 21];

Compounds of the present invention, in the formula (1C), wherein $R^1$ is an ethyl group, $R^2$ and $R^4$ are a hydrogen atom, $R^3$ is a trifluoromethylsulfanyl group, n is 1, and $A^1$, $A^2$, $A^3$ and G are the combinations shown in [Table 11] to [Table 21];

Compounds of the present invention, in the formula (1C), wherein $R^1$ is an ethyl group, $R^2$ and $R^4$ are a hydrogen atom, $R^3$ is a trifluoromethylsulfanyl group, n is 2, and $A^1$, $A^2$, $A^3$ and G are the combinations shown in [Table 11] to [Table 21];

Compounds of the present invention, in the formula (1C), wherein $R^1$ is an ethyl group, $R^2$ and $R^4$ are a hydrogen atom, $R^3$ is a trifluoromethylsulfinyl group, n is 0, and $A^1$, $A^2$, $A^3$ and G are the combinations shown in [Table 11] to [Table 21];

Compounds of the present invention, in the formula (1C), wherein $R^1$ is an ethyl group, $R^2$ and $R^4$ are a hydrogen atom, $R^3$ is a trifluoromethylsulfinyl group, n is 1, and $A^1$, $A^2$, $A^3$ and G are the combinations shown in [Table 11] to [Table 21];

Compounds of the present invention, in the formula (1C), wherein $R^1$ is an ethyl group, $R^2$ and $R^4$ are a hydrogen atom, $R^3$ is a trifluoromethylsulfinyl group, n is 2, and $A^1$, $A^2$, $A^3$ and G are the combinations shown in [Table 11] to [Table 21];

Compounds of the present invention, in the formula (1C), wherein $R^1$ is an ethyl group, $R^2$ and $R^4$ are a hydrogen atom, $R^3$ is a trifluoromethylsulfonyl group, n is 0, and $A^1$, $A^2$, $A^3$ and G are the combinations shown in [Table 11] to [Table 21];

Compounds of the present invention, in the formula (1C), wherein $R^1$ is an ethyl group, $R^2$ and $R^4$ are a hydrogen atom, $R^3$ is a trifluoromethylsulfonyl group, n is 1, and $A^1$, $A^2$, $A^3$ and G are the combinations shown in [Table 11] to [Table 21];

Compounds of the present invention, in the formula (1C), wherein $R^1$ is an ethyl group, $R^2$ and $R^4$ are a hydrogen atom, $R^3$ is a trifluoromethylsulfonyl group, n is 2, and $A^1$, $A^2$, $A^3$ and G are the combinations shown in [Table 11] to [Table 21].

Examples of the pest on which the compound of the present invention has an effect include arthropod pests such as Insecta, Arachnida, Chilopoda, Diplopoda, Isopoda and Gastropoda, and Nematode pests such as Nematoda. Examples of the pest insects include Hemiptera pests, Lepidoptera pests, Thysanoptera pests, Diptera pests, Coleoptera pests, Orthoptera pests, Siphonaptera pests, Anoplura pests, Mallophaga pests, Hymenoptera pests, Blattodea pests, Isoptera pests, and the like. Examples of Arachnida include Araneae pests, Acarina pests, and the like. Specifically, examples of the pests include those shown below.

Hemiptera: Delphacidae such as *Laodelphax striatellus*, *Nilaparvata lugens*, and *Sogatella furcifera*, Deltocephalidae such as *Nephotettix cincticeps*, *Nephotettix virescens*, and *Empoasca onukii*, Aphididae such as *Aphis gossypii*, *Myzus persicae*, *Brevicoryne brassicae*, *Aphis spiraecola*, *Macrosiphum euphorbiae*, *Aulacorthum solani*, *Rhopalosiphum padi*, *Toxoptera citricidus*, and *Hyalopterus pruni*, Pentatomidae such as *Nezara antennata*, *Riptortus clavetus*, *Leptocorisa chinensis*, *Eysarcoris parvus*, and *Halyomorpha mista*, Aleyrodidae such as *Trialeurodes vaporariorum*, *Bemisia tabaci*, *Dialeurodes citri*, and *Aleurocanthus spiniferus*, Coccidae such as *Aonidiella aurantii*, *Comstockaspis perniciosa*, *Unaspis citri*, *Ceroplastes rubens*, *Icerya purchasi*, *Planococcus kraunhiae*, *Pseudococcus longispinis*, and *Pseudaulacaspis pentagona*, Tingidae, Cimicoidea such as *Cimex lectularius*, and Psyliidae.

Lepidoptera: Pyralidae such as *Chilo suppressalis*, *Tryporyza incertulas*, *Cnaphalocrocis medinalis*, *Notarcha derogata*, *Plodia interpunctella*, *Ostrinia furnacalis*, *Hellula undalis*, and *Pediasia teterrellus*, Noctuidae such as *Spodoptera litura*, *Spodoptera exigua*, *Pseudaletia separata*, *Mamestra brassicae*, *Agrotis ipsilon*, *Plusia nigrisigna*, *Thoricoplusia* spp., *Heliothis* spp., and *Helicoverpa* spp., Pieridae such as *Pieris rapae*, *Adoxophyes* spp., Tortricidae such as *Grapholita molesta*, *Leguminivora glycinivorella*, *Matsumuraeses azukivora*, *Adoxophyes orana fasciata*, *Adoxophyes honmai.*, *Homona magnanima*, *Archips fuscocupreanus*, and *Cydia pomonella*, Gracillariidae such as *Caloptilia theivora* and *Phyllonorycter ringoneella*, Carposinidae such as *Carposina niponensis*, Lyonetiidae such as *Lyonetia* spp., Lymantriidae such as *Lymantria* spp. and *Euproctis* spp., Yponomeutidae such as *Plutella xylostella*, Gelechiidae such as *Pectinophora gossypiella* and *Phthorimaea operculella*, Arctiidae such as *Hyphantria cunea*, and Tineidae such as *Tinea translucens* and *Tineola bisselliella*.

Thysanoptera: Thripidae such as *Frankliniella occidentalis*, *Thrips parmi*, *Scirtothrips dorsalis*, *Thrips tabaci*, and *Frankliniella intonsa*.

Diptera: Culex such as *Culex pipiens pallens*, *Culex tritaeniorhynchus*, and *Culex quinquefasciatus*, *Aedes* spp. such as *Aedes aegypti* and *Aedes albopictus*, *Anopheles* spp. such as *Anopheles sinensis*, Chironomidae, Muscidae such as *Musca domestica* and *Muscina stabulans*, Calliphoridae, Sarcophagidae, Fanniidae, Anthomyiidae such as *Delia platura* and *Delia antiqua*, Agromyzidae such as *Agromyza oryzae*, *Hydrellia griseola*, *Liriomyza sativae*, *Liriomyza trifolii*, and *Chromatomyia horticola*, Chloropidae such as *Chlorops oryzae*, Tephritidae such as *Dacus cucurbitae* and *Ceratitis capitata*, Drosophilidae, Phoridae such as *Megaselia spiracularis*, Psychodidae such as *Clogmia albipunctata*, Sciaridae, Simuliidae, Tabanidae such as *Tabanus trigonus*, Hippoboscidae, and *Stomoxys*.

Coleoptera: Diabrotica such as *Diabrotica virgifera virgifera* and *Diabrotica undecimpunctata howardi*, Scarabaeidae such as *Anomala cuprea Anomala rufocuprea*, and *Popillia japonica*, Curculionidae such as *Sitophilus zeamais*, *Lissorhoptrus oryzophilus*, and *Callosobruchuys chienensis*, *Echinocnemus squameus*, *Anthonomus grandis*, and *Sphenophorus venatus*, Tenebrionidae such as *Tenebrio molitor* and *Tribolium castaneum*, Chrysomelidae such as *Oulema oryzae*, *Aulacophora femoralis*, *Phyllotreta striolata*, and *Leptinotarsa decemlineata*, Dermestidae such as *Anthrenus verbasci* and *Dermestes maculates*, Anobiidae such as *Lasioderma serricorne*, *Epilachna* such as *Epilachna vigintioctopunctata*, *Lyctus brunneus*, Scolytidae such as *Tomicus piniperda*, Bostrychidae, Ptinidae, Cerambycidae such as *Anoplophora malasiaca*, Elateridae such as *Agriotes* spp. and *Limonius* spp., and *Paederus fuscipes*.

Orthoptera: *Locusta migratoria*, *Gryllotalpa africana*, *Oxya yezoensis*, *Oxya japonica*, and Grylloidea.

Aphaniptera: *Ctenocephalides felis*, *Ctenocephalides canis*, *Pulex irritans*, *Xenopsylla cheopis*, and the like.

Anoplura: *Pediculus humanus corporis*, *Pediculus humanus humanus*, *Phthirus pubis*, *Haematopinus eurysternus*, *Dalmalinia ovis*, *Haematopinus suis*, *Linognathus setosus*, and the like.

Mallophaga: *Dalmalinia ovis*, *Dalmalinia bovis*, *Menopon gallinae*, *Trichodectes canis*, *Felicola subrostrata*, and the like.

Hymenoptera: Formicidae such as *Monomorium pharaosis*, *Formica fusca japonica*, *Ochetellus glaber*, *Pristomyrmex pungens*, *Pheidole noda*, *Acromyrmex* spp., *Solenopsis* spp., and *Linepithema humile*, Vespidae, Bethylidae, and Tenthredinidae such as *Athalia rosae* and *Athalia japonica*.

Nematoda: *Aphelenchoides besseyi*, *Nothotylenchus acris*, *Meloidogyne incognita*, *Meloidogyne hapla*, *Meloidogyne javanica*, *Heterodera glycines*, *Globodera rostochiensis*, *Pratylenchus coffeae*, and *Pratylenchus neglectus*.

Blattodea: *Blattella germanica*, *Periplaneta fuliginosa*, *Periplaneta americana*, *Periplaneta brunnea*, and *Blatta orientalis*.

Isoptera: *Reticulitermes speratus*, *Coptotermes formosanus*, *Incisitermes minor*, *Cryptotermes domesticus*, *Odontotermes formosanus*, *Neotermes koshunensis*, *Glyptotermes satsumensis*, *Glyptotermes nakajimai*, *Glyptotermes fuscus*, *Glyptotermes kodamai*, *Glyptotermes kushimensis*, *Hodotermopsis japonica*, *Coptotermes guangzhoensis*, *Reticulitermes miyatakei*, *Reticulitermes flaviceps amamianus*, *Reticulitermes* sp., *Nasutitermes takasagoensis*, *Pericapritermes nitobei*, *Sinocapritermes mushae*, and the like.

Acarina: Tetranychidae such as *Tetranychus urticae*, *Tetranychus kanzawai*, *Panonychus citri*, *Panonychus ulmi*, and *Oligonychus* spp., Eriophyidae such as *Aculops pelekassi*, *Phyllocoptruta citri*, *Aculops lycopersici*, *Calacarus carinatus*, *Acaphylla theavagrans*, *Eriophyes chibaensis*, and *Aculus schlechtendali*, Tarsonemidae such as *Polyphagotarsonemus latus*, Tenuipalpidae such as *Brevipalpus phoenicis*, Tuckerellidae, Metastigmata such as *Haemaphysalis longicornis*, *Haemaphysalis flava*, *Dermacentor taiwanicus*, *Dermacentor variabilis*, *Ixodes ovatus*, *Ixodes persulcatus*, *Ixodes scapularis*, *Amblyomma americanum*, *Boophilus microplus*, and *Rhipicephalus sanguineus*, Acaridae such as *Tyrophagus putrescentiae* and *Tyrophagus similis*, Pyroglyphidae such as *Dermatophagoides farinae* and *Dermatophagoides ptrenyssnus*, Cheyletidae such as *Cheyletus eruditus*, *Cheyletus malaccensis*, *Cheyletus moorei*, and *Cheyletiella yasguri*, Sarcoptidae such as *Octodectes cynotis* and *Sacroptes scabiei*, Demodicidae such as *Demodex canis*, Listrophoridae, Cryptostigmata, Dermanyssidae such as *Ornithonyssus bacoti*, *Ornithonyssus sylvairum*, and *Dermanyssus gallinae*, Trombiculidae such as *Leptotrombidium akamushi*, and the like.

Acarina pests: *Chiracanthium japonicum*, *Latrodectus hasseltii*, and the like.

Chilopoda, Scutigeromorpha pests: *Thereuonema hilgendorfi*, *Scolopendra subspinipes*, and the like.

Diplopoda, Polydesmoidea pests: *Oxidus gracilis*, *Nedyopus tambanus*, and the like.

Malacostraca, Isopoda: *Armadillidium vulgare*, and the like.

Gastropoda, Stylommatophora pests: *Limax marginatus*, *Limax flavus*, and the like.

The pest control agent of the present invention contains the compound of the present invention and an inert carrier. The pest control agent of the present invention is usually obtained by mixing the compound of the present invention and an inert carrier such as a solid carrier, a liquid carrier or a gaseous carrier, and adding a surfactant or other auxiliaries for formulation as necessary, to be formulated into emulsifiable concentrates, oil formulations, dust formulations, granules, wettable powders, flowables, microcapsule formulations, aerosols, smoking agents, poisonous bait formulations, resin formulations, shampoo agents, paste formulations, foam agents, carbon dioxide preparations, tablets, and the like. These formulations may be processed into mosquito repellent coil, electric mosquito repellent mat, mosquito repellent liquid formulation, smoking agent, fumigant, sheet formulation, spot-on agent, or oral treatment agent, and used.

The pest control agent of the present invention usually contains the compound of the present invention in an amount of 0.01 to 95% by weight.

Examples of the solid carrier which is used in the formulation include fine powder and granules of clays (kaolin clay, diatomaceous earth, bentonite, Fubasami clay, acid clay, etc.), synthetic hydrated silicon oxide, talc, ceramics, other inorganic minerals (sericite, quartz, sulfur, activated carbon, calcium carbonate, hydrated silica, etc.), fine powder and granulated substances of chemical fertilizers (ammonium sulfate, ammonium phosphate, ammonium nitrate, urea, ammonium chloride, etc.) and the like, synthetic resins (polyester resins such as polypropylene, polyacrylonitrile, polymethylmethacrylate and polyethylene terephthalate, nylon resins such as nylon-6, nylon-11 and nylon-66, polyamide resin, polyvinyl chloride, polyvinylidene chloride, vinyl chloride-propylene copolymer, and the like).

Examples of the liquid carrier include water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, light oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc.), acid amides (N,N-dimethylformamide, N,N-dimethylacetamide, etc.), halogenated hydrocarbons (dichloromethane, trichloroethane, carbon tetrachloride, etc.), sulfoxides (dimethyl sulfoxide, etc.), and propylene carbonate and vegetable oils (soybean oil, cottonseed oil, etc.).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ether, polyoxyethylene alkylaryl ether and polyethylene glycol fatty acid ester, and anionic surfactants such as alkyl sulfonates, alkylbenzene sulfonates and alkylsulfates.

The other auxiliaries for formulation include such as fixing agents, dispersants, colorants and stabilizers, specifically, for example, casein, gelatin, polysaccharides (starch, arabic gum, cellulose derivatives, alginic acid, etc.), lignin derivatives, bentonite, synthetic water-soluble polymers (polyvinyl alcohol, polyvinyl pyrrolidone, polyacrylic acid, etc.), PAP (isopropyl acid phosphate), BHT (2,6-di-tert-butyl-4-methylphenol) and BHA (mixtures of 2-tert-butyl-4-methoxyphenol and 3-tert-butyl-4-methoxyphenol).

Examples of a base material of the resin formulation include vinyl chloride polymer, polyurethane and the like, and a plasticizer such as phthalate esters (dimethyl phthalate, dioctyl phthalate, etc.), adipate esters or stearic acid may be added to these base materials as necessary. The resin formulation is obtained by kneading a compound into the base material using an ordinary kneading apparatus, and then molding it by injection molding, extrusion molding, press molding or the like, and the resin formulation obtained can be further subjected to molding or cutting step as necessary to be processed into a plate, film, taped, reticular or string resin formulation. These resin formulations are processed into, for example, a collar for animal, an ear tag for animal, a sheet formulation, an induction cord, and a gardening pole.

Examples of a base material of the poisonous bait include grain powder, vegetable oil, sugar, crystalline cellulose and the like, and further, an antioxidant such as dibutylhydroxytoluene and nordihydroguaiaretic acid, a preservative such as dehydroacetic acid, a substance for preventing accidental ingestion by children and pets such as red pepper powder, a pest attractant flavor such as cheese flavor, onion flavor and peanut oil or the like are added as necessary.

The method for controlling pests of the present invention is carried out by applying an effective amount of the compound of the present invention to a pest directly and/or a pest-infested area (plants, soil, in-house, animal body, etc.). In the method for controlling pests of the present invention, the compound is usually used in the form of the pest control agent of the present invention.

When the pest control agent of the present invention is used in pest controlling in the agricultural field, the application amount is usually 1 to 10000 g in the amount of the compound of the present invention per 10000 m$^2$. When the pest control agent of the present invention is formulated into an emulsifiable concentrate, a wettable powder, a flowable or the like, the pest control agent is usually diluted with water for an application so as to have a concentration of the active ingredient of 0.01 to 10000 ppm, and dust formulations, granules and the like are usually applied as they are.

These formulations and formulation solutions diluted with water may be directly applied by being sprayed on a pest or a plant such as crops which should be protected from pests, and also may be applied to a soil in order to control a pest that infests in the soil of cultivated land.

Also, the resin formulation processed into a sheet or string can be also applied by a method such as winding it around crops, spreading it in the vicinity of crops, or spreading it to the soil around crop roots.

When the pest control agent of the present invention is used in controlling the pest that inhabits in the house, the application amount is usually 0.01 to 1000 mg in an amount of the compound of the present invention per 1 $m^2$ of an area to be treated, in the case of using it on a planar area, and is usually 0.01 to 500 mg in an amount of the compound of the present invention per 1 $m^3$ of a space to be treated, in the case of using it in a space. When the pest control agent of the present invention is formulated into an emulsifiable concentrate, a wettable powder, a flowable or the like, the pest control agent is usually diluted with water for an application so as to have a concentration of the active ingredient of 0.1 to 10000 ppm, and oil formulations, aerosols, smoking agents, poisonous bait formulations and the like are applied as they are.

When the arthropod pest control agent of the present invention is used in the control of external parasites on livestock such as cows, horses, pigs, sheep, goats and chickens, and small animals such as dogs, cats, rats and mice, veterinary known methods can be applied to the animals. As specific methods, the formulation is administered, for example, by way of a tablet, mixing in feed, a suppository and injection (intramuscular, subcutaneous, intravenous, intraperitoneal injections, etc.), when systemic control is intended, and the formulation is used, for example, by way of spraying an oil solution or aqueous solution, pour-on or spot-on treatment, washing an animal with a shampoo formulation, or putting a collar or ear tag made of a resin formulation on to an animal, when non-systemic control is intended. The amount of the compound of the present invention when administered to an animal body is usually in the range from 0.1 to 1000 mg per 1 kg of the weight of an animal.

The pest control agent of the present invention can be used in the farmlands where the following "crops" are grown.

Crops: corn, rice, wheat, barley, rye, oat, sorghum, cotton, soybean, peanut, sarrazin, sugar beet, rapeseed, sunflower, sugar cane, tobacco, etc.

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horse-radish, kohlrabi, Chinese cabbage, cabbage, brown mustard, broccoli, cauliflower, etc.), Compositae vegetables (burdock, garland *chrysanthemum*, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese mint, mint, basil, etc.), strawberry, sweat potato, yam, aroid, etc.

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruits, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut, oil palm, etc.

Trees other than fruit trees: tea, mulberry, flowering trees and shrubs (azalea, *camellia, hydrangea*, sasanqua, Illicium religiosum, cherry tree, tulip tree, crape myrtle, fragrant olive, etc.), street trees (ash tree, birch, dogwood, *eucalyptus*, ginkgo, lilac, maple tree, oak, poplar, *cercis*, Chinese sweet gum, plane tree, *zelkova*, Japanese arborvitae, fir tree, Japanese hemlock, needle juniper, pine, spruce, yew, elm, horse-chestnut, etc.), sweet *viburnum, Podocarpus macrophyllus*, Japanese cedar, Japanese cypress, croton, spindle tree, Japanese *photinia*, etc.

Grass: *zoysia* (Japanese lawn grass, mascarene grass, etc.), Bermuda grass (*Cynodon dactylon*, etc.), bent grass (creeping bent grass, *Agrostis stolonifera, Agrostis tenuis*, etc.), bluegrass (Kentucky bluegrass, rough bluegrass, etc.), fescue (tall fescue, chewing fescue, creeping fescue, etc.), ryegrass (darnel, perennial ryegrass, etc.), cocksfoot, timothy grass, etc.

Others: flowers (rose, carnation, *chrysanthemum, Eustoma grandiflorum* Shinners (prairie gentian), *gypsophila, gerbera*, pot marigold, *salvia, petunia, verbena*, tulip, aster, gentian, lily, pansy, cyclamen, orchid, lily of the valley, lavender, stock, ornamental kale, *primula*, poinsttia, *gladiolus*, cattleya, daisy, cymbidium, *begonia*, etc.), biofuel plants (Jatropha, curcas, safflower, Camelina *alyssum*, switchgrass, *miscanthus*, reed canary grass, *Arundo donax*, kenaf, cassava, willow, algae, etc.), foliage plants, etc.

The "crops" also contain genetically modified crops.

The pest control agent of the present invention can be used as a mixture with or in combination with other insecticide, miticide, nematicide, fungicide, plant growth regulator, herbicide or synergist. Examples of the active ingredient of said insecticide, miticide, nematicide, fungicide, herbicide and synergist are shown below.

Active Ingredients of Insecticide (1) Organic Phosphorus Compounds acephate, aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropyl ether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos.

(2) Carbamate Compounds alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and aldicarb.

(3) Pyrethroid Compounds acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS,3RS;1RS,3SR)-2,2-dimethyl-3-prop-1-enylcyclopropanecarboxylate, 2,3,5,6-tetrafluoro-4-methylbenzyl (EZ)-(1RS,3RS;1RS,3SR)-2,2-dimethyl-3-prop-1-enylcyclopropanecarboxylate, 2,3,5,6-tetrafluoro-4-(methoxymethyl)benzyl (1RS,3RS;1RS,3SR)-2,2-dimethyl-3-(2-methyl-1-propenyl)cyclopropanecarboxylate, and 2,3,5,6-tetrafluoro-4-(methoxymethyl)benzyl(EZ)-(1RS,3RS;1RS,3SR)-2,2-dimethyl-3-(2-cyano-1-propenyl)cyclopropanecarboxylate.

(4) Nereistoxin Compounds cartap, bensultap, thiocyclam, monosultap, and bisultap.

(5) Neonicotinoid Compounds imidacloprid, nitenpyram, acetamiprid, thiamethoxam, thiacloprid, dinotefuran, and clothianidin.

(6) Benzoyl Urea Compounds chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole Compounds acetoprole, ethiprole, fipronil, vaniliprole, pyriprole, and pyrafluprole.

(8) Bt Toxins

Living spores derived from *Bacillus thuringiensis* and produced crystalline toxins and mixtures thereof;

(9) Hydrazine Compounds chromafenozide, halofenozide, methoxyfenozide, and tebufenozide.

(10) Organic Chlorine Compounds aldrin, dieldrin, dienochlor, endosulfan, and methoxychlor.

(11) Other Active Ingredients of Insecticide machine oil, nicotine-sulfate; avermectin-B, bromopropylate, buprofezin, chlorphenapyr, cyantraniliprole, cyromazine, D-D(1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfoxaflor, sulfur, metaflumizone, spirotetramat, pyrifluquinazone, spinetoram, chlorantraniliprole, tralopyril, cyantraniliprole, compounds represented by the following formula (K)

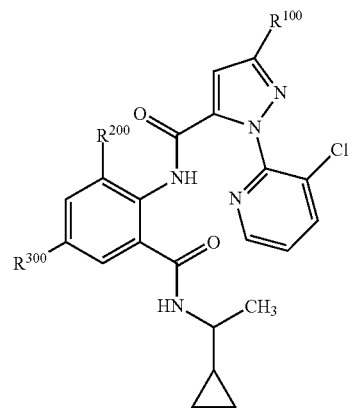

(K)

wherein
$R^{100}$ represents chlorine, bromine or a trifluoromethyl group,
$R^{200}$ represents chlorine, bromine or a methyl group, and
$R^{300}$ represents chlorine, bromine or a cyano group, and compounds represented by the following formula (L)

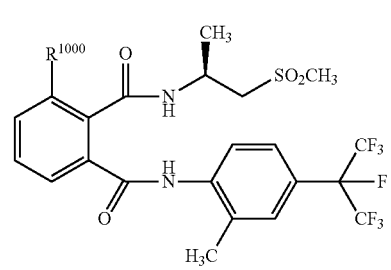

(L)

wherein
$R^{1000}$ represents chlorine, bromine or iodine.

Active Ingredients of Miticide acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite: BPPS, polynactins, pyridaben, pyrimidifen, tebufenpyrad, tetradifon, spirodiclofen, spiromesifen, spirotetramat, amidoflumet, and cyenopyrafen.

Active Ingredients of Nematicide

DCIP, fosthiazate, levamisol, methyisothiocyanate, morantel tartarate, and imicyafos.

Active ingredients of Fungicide azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;

cyclic amine fungicidal compounds such as fenpropimorph, tridemorph, and fenpropidin;

benzimidazole fungicidal compounds such as carbendezim, benomyl, thiabendazole, and thiophanate-methyl; procymidone; cyprodinil; pyrimethanil; diethofencarb; thiuram; fluazinam; mancozeb; iprodione; vinclozolin; chlorothalonil;

captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil and tiadinil.

Active Ingredients of Herbicide (1) Phenoxy fatty acid herbicidal compounds
2,4-PA, MCP, MCPB, phenothiol, mecoprop, fluroxypyr, triclopyr, clomeprop, and naproanilide.

(2) Benzoate herbicidal compounds
2,3,6-TBA, dicamba, clopyralid, picloram, aminopyralid, quinclorac, and quinmerac.

(3) Urea herbicidal compounds
diuron, linuron, chlortoluron, isoproturon, fluometuron, isouron, tebuthiuron, methabenzthiazuron, cumyluron, daimuron, and methyl-daimuron.

(4) Triazine herbicidal compounds
atrazine, ametoryn, cyanazine, simazine, propazine, simetryn, dimethametryn, prometryn, metribuzin, triaziflam, and indaziflam.

(5) Bipyridinium herbicidal compounds
paraquat, and diquat.

(6) Hydroxybenzonitrile herbicidal compounds
bromoxynil, and ioxynil.

(7) Dinitroaniline herbicidal compounds
pendimethalin, prodiamine, and trifluralin.

(8) Organophosphorus herbicidal compounds
amiprofos-methyl, butamifos, bensulide, piperophos, anilofos, glyphosate, glufosinate, glufosinate-P, and bialaphos.

(9) Carbamate herbicidal compounds
di-allate, tri-allate, EPTC, butylate, benthiocarb, esprocarb, molinate, dimepiperate, swep, chlorpropham, phenmedipham, phenisopham, pyributicarb, and asulam.

(10) Acid amide herbicidal compounds
propanil, propyzamide, bromobutide, and etobenzanid.

(11) Chloroacetanilide herbicidal compounds
acetochlor, alachlor, butachlor, dimethenamid, propachlor, metazachlor, metolachlor, pretilachlor, thenylchlor, and pethoxamid.

(12) Diphenyl ether herbicidal compounds
acifluorfen-sodium, bifenox, oxyfluorfen, lactofen, fomesafen, chlomethoxynil, and aclonifen.

(13) Cyclic imide herbicidal compounds
oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.

(14) Pyrazole herbicidal compounds
benzofenap, pyrazolate, pyrazoxyfen, topramezone, and pyrasulfotole.

(15) Triketone herbicidal compounds
isoxaflutole, benzobicyclon, sulcotrione, mesotrione, tembotrione, and tefuryltrione.

(16) Aryloxyphenoxypropionate herbicidal compounds
clodinafop-propargyl, cyhalofop-butyl, diclofop-methyl, fenoxaprop-ethyl, fluazifop-butyl, haloxyfop-methyl, and quizalofop-ethyl, metamifop.

(17) Trione oxime herbicidal compounds
alloxydim-sodium, sethoxydim, butroxydim, clethodim, cloproxydim, cycloxydim, tepraloxydim, tralkoxydim, and profoxydim.

(18) Sulfonyl urea herbicidal compounds
chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.

(19) Imidazolinone herbicidal compounds
imazamethabenz-methyl, imazamethapyr, imazamox, imazapyr, imazaquin, and imazethapyr.

(20) Sulfonamide herbicidal compounds
flumetsulam, metosulam, diclosulam, florasulam, cloransulam-methyl, penoxsulam, and pyroxsulam.

(21) Pyrimidinyloxybenzoate herbicidal compounds
pyrithiobac-sodium, bispyribac-sodium, pyriminobac-methyl, pyribenzoxim, pyriftalid, and pyrimisulfan.

(22) Other herbicidal compounds
bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Active Ingredients of Synergist
piperonyl butoxide, sesamex, sulfoxide, N-(2-ethylhexyl)-8,9,10-trinorborn-5-ene-2,3-dicarboximide (MGK 264), N-declyimidazole), WARF-antiresistant, Tribuphos (TBPT), triphenyl phosphite (TPP), iprobenfos (IBP), methyl iodide ($CH_3I$), t-phenylbutenone, diethylmaleate, bis(p-chlorophenyl)methyl carbinol (DMC), and bis(p-chlorophenyl)trifluoromethyl carbinol (FDMC).

EXAMPLES

Hereinbelow, the present invention will be further described in detail with reference to production examples, formulation examples, test examples, and the like. However, the present invention is not limited to these examples. First, the production examples for the production of the compounds of the present invention are shown below.

Production Example 1 (1)

To a mixture of 9.61 g of $N^2$-methyl-5-trifluoromethyl-pyridine-2,3-diamine (synthesized by a method described in WO2010-125985), 9.2 g of 3,5-dichloro-pyridine-2-carboxylic acid and 48 ml of pyridine were added 9.64 g of EDCI hydrochloride and 0.64 g of HOBt, under ice cooling, and the mixture was stirred at room temperature for 6 hours. Water was added to the reaction mixture, and the precipitated solid was filtered. Ethyl acetate and water were added to the resulting solid, and the mixture was extracted with ethyl acetate. The organic layer was dried over anhydrous sodium sulfate and concentrated under reduced pressure to produce 15.73 g of 3,5-dichloro-N-(2-methylamino-5-trifluoromethylpyridin-3-yl)-picolinamide.

3,5-Dichloro-N-(2-methylamino-5-trifluoromethyl-pyridin-3-yl)-picolinamide

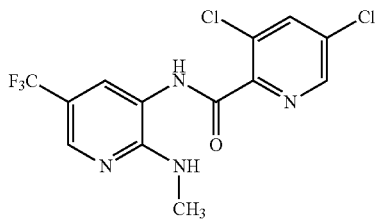 [SMILES: CNc1ncc(C(F)(F)F)cc1NC(=O)c1ncc(Cl)cc1Cl]

$^1$H-NMR (CDCl$_3$) δ: 9.33 (1H, brs), 8.51 (1H, d), 8.37 (1H, d), 7.95 (1H, d), 7.86 (1H, d), 5.02 (1H, brs), 3.08 (3H, d).

Production Example 1 (2)

A mixture of 15.73 g of 3,5-dichloro-N-(2-methylamino-5-trifluoromethylpyridin-3-yl)-picolinamide and 43 ml of acetic acid was heated and stirred at 130° C. for 4 hours. The cooled reaction mixture was added to water, and the precipitated solid was filtered. Ethyl acetate and saturated aqueous sodium bicarbonate solution were added to the resulting solid, and the mixture was extracted with ethyl acetate. The organic layer was dried over anhydrous sodium sulfate and concentrated under reduced pressure to produce 14.47 g of 2-(3,5-dichloropyridin-2-yl)-3-methyl-6-trifluoromethyl-3H-imidazo[4,5-b] pyridine.

2-(3,5-Dichloropyridin-2-yl)-3-methyl-6-trifluoromethyl-3H-imidazo[4,5-b] pyridine

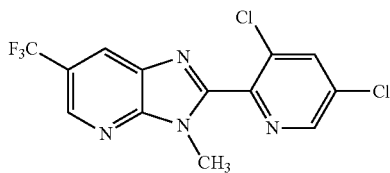 [SMILES: Cn1c(-c2ncc(Cl)cc2Cl)nc2cc(C(F)(F)F)cnc21]

$^1$H-NMR (CDCl$_3$) δ: 8.76 (1H, dd), 8.67 (1H, d), 8.40 (1H, dd), 8.01 (1H, d), 3.98 (3H, s)

Production Example 1 (3)

A mixture of 1.1 ml of ethyl mercaptan and 5 ml of THF was added to a mixture of 5.0 g of 2-(3,5-dichloropyridin-2-yl)-3-methyl-6-trifluoromethyl-3H-imidazo[4,5-b] pyridine, 0.63 g of 60% sodium hydride (oily) and 30 ml of THF, over 30 minutes, and the mixture was stirred at room temperature for 2 hours. The reaction mixture was added to ice water, and the precipitated solid was filtered. The resulting solid was washed with water and hexane and dried under reduced pressure to produce 5.19 g of 2-(5-chloro-3-ethyl-sulfanylpyridin-2-yl)-3-methyl-6-trifluoromethyl-3H-imidazo[4,5-b] pyridine.

2-(5-Chloro-3-ethylsulfanylpyridin-2-yl)-3-methyl-6-trifluoromethyl-3H-imidazo[4,5-b] pyridine

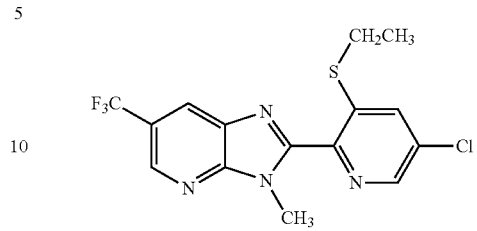

$^1$H-NMR (CDCl$_3$) δ: 8.74 (1H, dd), 8.45 (1H, d), 8.40 (1H, dd), 7.72 (1H, d), 4.07 (3H, s), 2.98 (2H, q), 1.39 (3H, t).

Production Example 1 (4)

To a mixture of 15.48 g of 2-(5-chloro-3-ethylsulfanylpyridin-2-yl)-3-methyl-6-trifluoromethyl-3H-imidazo[4,5-b] pyridine and 208 ml of chloroform was added 21.96 g of m-chloroperbenzoic acid (purity of 65% or more), under ice cooling, then the mixture was stirred at room temperature for 6.5 hours. A 10% aqueous sodium thiosulfate solution and a saturated sodium bicarbonate solution were added to the reaction mixture, and the mixture was extracted with chloroform. The organic layer was dried over anhydrous sodium sulfate, and then concentrated under reduced pressure. Ethyl acetate and hexane were added to the resulting crude product, and the precipitated solid was filtered and dried under reduced pressure to produce 12.94 g of 2-(5-chloro-3-ethylsulfonylpyridin-2-yl)-3-methyl-6-trifluoromethyl-3H-imidazo[4,5-b] pyridine.

2-(5-Chloro-3-ethylsulfonylpyridin-2-yl)-3-methyl-6-trifluoromethyl-3H-imidazo[4,5-b] pyridine

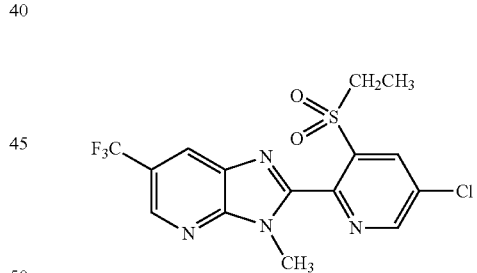

$^1$H-NMR (CDCl$_3$) δ: 8.95 (1H, dd), 8.77 (1H, dd), 8.53 (1H, dd), 8.32 (1H, dd), 3.94-3.86 (5H, m), 1.40 (3H, t).

Production Example 1 (5)

To a mixture of 7.25 g of 2-(5-chloro-3-ethylsulfonylpyridin-2-yl)-3-methyl-6-trifluoromethyl-3H-imidazo[4,5-b] pyridine and 40 ml of NMP was added 1.52 g of sodium azide, and the mixture was stirred at 90° C. for 4 hours. A saturated aqueous sodium bicarbonate solution was added to the cooled reaction mixture, and the mixture was extracted with ethyl acetate. The organic layer was washed with water, then dried over anhydrous sodium sulfate, and concentrated under reduced pressure to produce 2-(5-azide-3-ethylsulfonylpyridin-2-yl)-3-methyl-6-trifluoromethyl-3H-imidazo[4,5-b] pyridine.

A mixture of the whole amount of 2-(5-azide-3-ethylsulfonylpyridin-2-yl)-3-methyl-6-trifluoromethyl-3H-imidazo[4,5-b] pyridine produced above, 6.12 g of triphenylphosphine, 73 ml of THF and 7 ml of water was stirred at room temperature for 5.5 hours. To the reaction mixture was added 1 ml of concentrated hydrochloric acid, and the mixture was stirred at room temperature for 6 hours. Water was added to the reaction mixture, and the mixture was extracted with ethyl acetate. The organic layer was dried over anhydrous sodium sulfate, and then concentrated under reduced pressure.

The resulting residue was subjected to a silica gel column chromatography to produce 4.68 g of 2-(5-amino-3-ethylsulfonylpyridin-2-yl)-3-methyl-6-trifluoromethyl-3H-imidazo[4,5-b] pyridine.

2-(5-Amino-3-ethylsulfonylpyridin-2-yl)-3-methyl-6-trifluoromethyl-3H-imidazo[4,5-b] pyridine

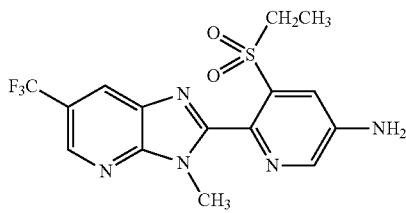 [SMILES: CCS(=O)(=O)c1cc(N)cnc1-c1nc2cc(C(F)(F)F)cnc2n1C]

$^1$H-NMR (CDCl$_3$) δ: 8.72 (1H, dd), 8.36 (1H, d), 8.27 (1H, dd), 7.70 (1H, d), 4.36 (2H, brs), 3.84 (3H, s), 3.81 (2H, q), 1.36 (3H, t).

Production Example 1 (6)

To a mixture of 0.15 g of 2-(5-amino-3-ethylsulfonylpyridin-2-yl)-3-methyl-6-trifluoromethyl-3H-imidazo[4,5-b] pyridine, 2 ml of chloroform, and 0.1 ml of diisopropylethylamine was added 0.03 ml of methanesulfonyl chloride, under ice cooling, and the mixture was stirred at room temperature for 4 hours. To the reaction mixture were added 0.07 ml of diisopropylethylamine and 0.03 ml of methanesulfonyl chloride, under ice cooling, and the mixture was stirred at room temperature for 4 hours. A saturated aqueous ammonium chloride solution was added to the reaction mixture, and the mixture was extracted with ethyl acetate. The organic layer was dried over anhydrous sodium sulfate, and then concentrated under reduced pressure. The resulting residue was subjected to silica gel column chromatography to produce 0.18 g of N-[5-ethylsulfonyl-6-(3-methyl-6-trifluoromethyl-3H-imidazo [4,5-b] pyridin-2-yl)-pyridin-3-yl]-methylsulfonimide (hereinafter, referred to as Compound of Present Invention 2)

Compound of Present Invention 2

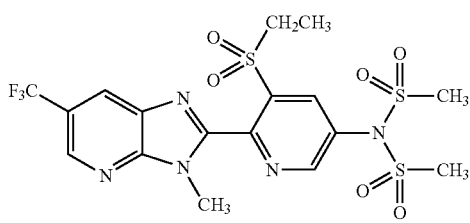 [SMILES: CCS(=O)(=O)c1cc(N(S(C)(=O)=O)S(C)(=O)=O)cnc1-c1nc2cc(C(F)(F)F)cnc2n1C]

$^1$H-NMR (CDCl$_3$) δ: 8.95 (1H, d), 8.79 (1H, d), 8.52 (1H, d), 8.33 (1H, d), 3.96 (3H, s), 3.93 (2H, q), 3.51 (6H, s), 1.40 (3H, t).

Production Example 2

To a mixture of 0.15 g of 2-(5-amino-3-ethylsulfonylpyridin-2-yl)-3-methyl-6-trifluoromethyl-3H-imidazo[4,5-b] pyridine, 2 ml of DMF, and 0.2 ml of diisopropylethylamine was added 0.1 ml of propargyl chloroformate, under ice cooling, and the mixture was stirred at room temperature for 4 days. A saturated aqueous ammonium chloride solution was added to the reaction mixture, and the mixture was extracted with ethyl acetate. The organic layer was dried over anhydrous sodium sulfate, and then concentrated under reduced pressure. The resulting residue was subjected to silica gel column chromatography to produce 0.08 g of N'-[5-ethylsulfonyl-6-(3-methyl-6-trifluoromethyl-3H-imidazo[4,5-b]pyridin-2-yl)-pyridin-3-yl]-N,N-dimethylformamidine (hereinafter, referred to as Compound of Present Invention 3)

Compound of Present Invention 3

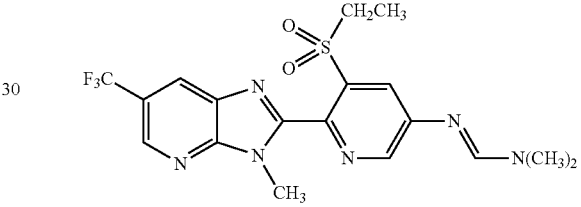

$^1$H-NMR (CDCl$_3$) δ: 8.73 (1H, d), 8.60 (1H, d), 8.28 (1H, d), 7.98 (1H, d), 7.76 (1H, s), 3.85 (3H, s), 3.81 (2H, q), 3.17 (3H, s), 3.14 (3H, s), 1.36 (3H, t).

Production Example 3

To a mixture of 0.15 g of 2-(5-amino-3-ethylsulfonylpyridin-2-yl)-3-methyl-6-trifluoromethyl-3H-imidazo[4,5-b] pyridine and 2 ml of chloroform was added 0.07 ml of methanesulfonic anhydride, under ice cooling, and the mixture was stirred at room temperature for 6 hours. To the reaction mixture were added 0.01 ml of pyridine and 0.04 ml of methanesulfonyl chloride, under ice cooling, and the mixture was stirred at room temperature for 4 hours. Water was added to the reaction mixture, and the mixture was extracted with ethyl acetate. The organic layer was dried over anhydrous sodium sulfate, and then concentrated under reduced pressure. To the resulting residue were added 2 ml of chloroform, 0.01 ml of pyridine and 0.01 ml of methanesulfonyl chloride, and the mixture was stirred at room temperature for 9 hours. Water was added to the reaction mixture, and the mixture was extracted with ethyl acetate. The organic layer was dried over anhydrous sodium sulfate, and then concentrated under reduced pressure. The resulting residue was subjected to silica gel column chromatography to produce 0.08 g of N-[5-ethylsulfonyl-6-(3-methyl-6-trifluoromethyl-3H-imidazo [4,5-b] pyridin-2-yl)-pyridin-3-yl]-methylsulfonamide (hereinafter, referred to as Compound of Present Invention 4)

Compound of Present Invention 4

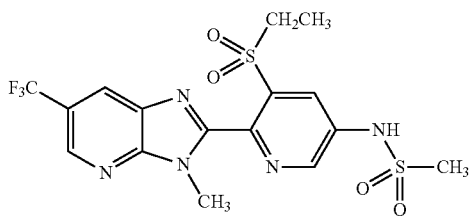 [SMILES: CCS(=O)(=O)c1cc(NS(C)(=O)=O)cnc1-c1nc2cc(C(F)(F)F)cnc2n1C]

$^1$H-NMR (CDCl$_3$) δ: 8.86 (1H, d), 8.76 (1H, d), 8.32-8.30 (2H, m), 3.95-3.87 (5H, m), 3.25 (3H, s), 1.39 (3H, t).

Production Example 4

To a mixture of 0.15 g of 2-(5-amino-3-ethylsulfonylpyridin-2-yl)-3-methyl-6-trifluoromethyl-3H-imidazo[4,5-b]pyridine and 2 ml of pyridine was added 0.07 ml of dimethylcarbamoyl chloride, under ice cooling, and the mixture was stirred under heating reflux for 4 hours. Water was added to the cooled reaction mixture, and the mixture was extracted with ethyl acetate. The organic layer was dried over anhydrous sodium sulfate and concentrated under reduced pressure. The resulting residue was subjected to silica gel column chromatography to produce 0.03 g of 3-[5-ethylsulfonyl-6-(3-methyl-6-trifluoromethyl-3H-imidazo [4,5-b] pyridin-2-yl)-pyridin-3-yl]-1,1-dimethylurea (hereinafter, referred to as Compound of Present Invention 5)

Compound of Present Invention 5

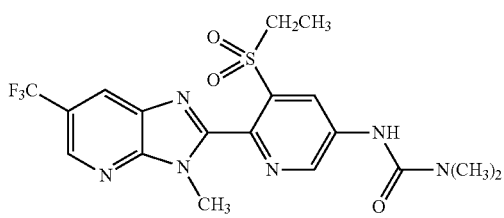 [SMILES: CCS(=O)(=O)c1cc(NC(=O)N(C)C)cnc1-c1nc2cc(C(F)(F)F)cnc2n1C]

$^1$H-NMR (CDCl$_3$) δ: 9.22 (1H, dd), 8.74 (1H, dd), 8.50 (1H, dd), 8.29 (1H, dd), 6.85 (1H, brs), 3.92-3.82 (5H, m), 3.12 (6H, s), 1.38 (3H, t).

Production Example 5 (1)

To a mixture of 5.0 g of 3,6-dichloropicolinic acid, 0.1 ml of DMF and 52 mL of toluene was added 3.8 ml of thionyl chloride, and the mixture was stirred under heating reflux for 3 hours. The reaction mixture cooled to room temperature was concentrated under reduced pressure to produce 3,6-dichloropicolinoyl chloride.
A mixture of 3, 6-dichloropicolinoyl chloride produced above and 5 ml of THF was added to a mixture of 5.7 g of 2-amino-4-trifluoromethylsulfanylphenol and 52 ml of THF, under ice cooling, and the mixture was stirred at room temperature for 6 hours. Water and a saturated aqueous sodium bicarbonate solution were added to the reaction mixture, and the mixture was extracted with ethyl acetate. The organic layer was dried over anhydrous sodium sulfate and concentrated under reduced pressure. The resulting residue was subjected to a silica gel column chromatography to produce 8.94 g of 3,6-dichloro-N-[2-hydroxy-5-(trifluoromethylsulfanyl)phenyl]picolinamide.

3,6-Dichloro-N-[2-hydroxy-5-(trifluoromethylsulfanyl)phenyl]picolinamide

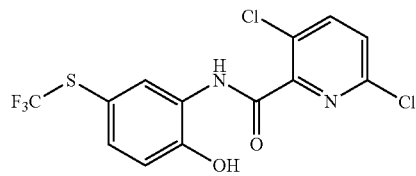 [SMILES: O=C(Nc1cc(SC(F)(F)F)ccc1O)c1nc(Cl)ccc1Cl]

$^1$H-NMR (CDCl$_3$) δ: 9.92 (1H, s), 8.95-8.88 (1H, m), 7.92-7.85 (1H, m), 7.69-7.65 (1H, m), 7.53-7.48 (1H, m), 7.48-7.40 (1H, m), 7.12-7.05 (1H, m).

Production Example 5 (2)

To a mixture of 8.94 g of 3,6-dichloro-N-[2-hydroxy-5-(trifluoromethylsulfanyl)phenyl]picolinamide, 47 ml of THF and 7.34 g of triphenylphosphine was added 7.10 g of di-2-methoxyethylazodicarboxylate (hereinafter referred to as DMEAD), under ice cooling, and the mixture was stirred at room temperature overnight. Water and a saturated aqueous ammonium chloride solution were added to the reaction mixture, and the mixture was extracted with ethyl acetate. The organic layer was dried over anhydrous sodium sulfate and concentrated under reduced pressure. The resulting residue was subjected to a silica gel column chromatography to produce 6.39 g of 2-(3,6-dichloropyridin-2-yl)-5-(trifluoromethylsulfanyl)benzoxazole.

2-(3,6-Dichloropyridin-2-yl)-5-(trifluoromethylsulfanyl)benzoxazole

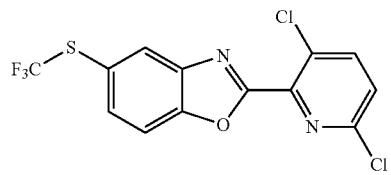 [SMILES: FC(F)(F)Sc1ccc2oc(-c3nc(Cl)ccc3Cl)nc2c1]

$^1$H-NMR (CDCl$_3$) δ: 8.25 (1H, s), 7.91 (1H, d), 7.79-7.72 (2H, m), 7.48 (1H, d).

Production Example 5 (3)

To a mixture of 6.39 g of 2-(3,6-dichloropyridin-2-yl)-5-(trifluoromethylsulfanyl)benzoxazole and 45 ml of THF was added 0.84 g of 60% sodium hydride (oily), then a mixture of 1.29 ml of ethyl mercaptan and 4 ml of THF was added thereto over 30 minutes, under ice cooling, and the mixture was stirred at room temperature for 3 hours. The reaction mixture was added to ice water, and the precipitated solid was filtered. The resulting solid was washed with water and hexane and dried under reduced pressure to produce 6.06 g of 2-(6-chloro-3-ethylsulfanylpyridin-2-yl)-5-(trifluoromethylsulfanyl)benzoxazole.

2-(6-Chloro-3-ethylsulfanylpyridin-2-yl)-5-(trifluoromethylsulfanyl)benzoxazole

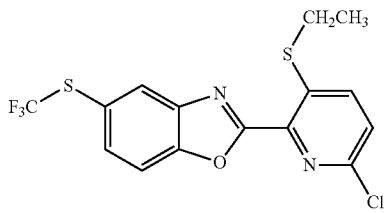 [SMILES: CCSc1ccc(Cl)nc1-c1nc2cc(SC(F)(F)F)ccc2o1]

$^1$H-NMR (CDCl$_3$) δ: 8.26 (1H, s), 7.77-7.69 (3H, m), 7.44 (1H, d), 3.06 (2H, q), 1.47 (3H, t).

Production Example 5 (4)

To a mixture of 6.06 g of 2-(6-chloro-3-ethylsulfanylpyridin-2-yl)-5-(trifluoromethylsulfanyl)benzoxazole and 45 ml of chloroform was added 7.13 g of m-chloroperbenzoic acid (purity of 65% or more) under ice cooling, and the mixture was stirred for 4 hours under ice cooling. A 10% aqueous sodium thiosulfate solution and a saturated sodium bicarbonate solution were added to the reaction mixture, and the mixture was extracted with chloroform. The organic layer was dried over anhydrous sodium sulfate and concentrated under reduced pressure. The resulting residue was subjected to a silica gel column chromatography to produce 4.24 g of 2-(6-chloro-3-ethylsulfonylpyridin-2-yl)-5-(trifluoromethylsulfanyl)benzoxazole and 0.68 g of 2-(6-chloro-3-ethylsulfonylpyridin-2-yl)-5-(trifluoromethylsulfinyl)benzoxazole.

2-(6-Chloro-3-ethylsulfonylpyridin-2-yl)-5-(trifluoromethylsulfanyl)benzoxazole

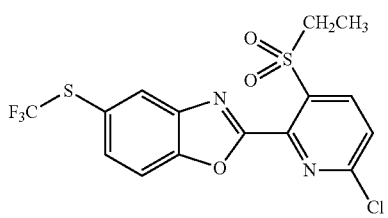 [SMILES: CCS(=O)(=O)c1ccc(Cl)nc1-c1nc2cc(SC(F)(F)F)ccc2o1]

$^1$H-NMR (CDCl$_3$) δ: 8.52 (1H, d), 8.18 (1H, s), 7.80-7.72 (3H, m), 4.03 (2H, d), 1.43 (3H, t).

2-(6-Chloro-3-ethylsulfonylpyridin-2-yl)-5-(trifluoromethylsulfinyl)benzoxazole

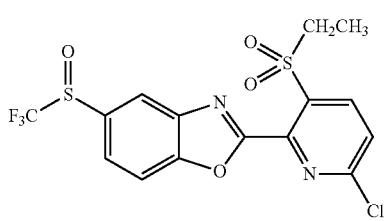 [SMILES: CCS(=O)(=O)c1ccc(Cl)nc1-c1nc2cc(S(=O)C(F)(F)F)ccc2o1]

$^1$H-NMR (CDCl$_3$) δ: 8.53 (1H, d), 8.36 (1H, s), 7.94 (1H, d), 7.89 (1H, d), 7.76 (1H, d), 4.01 (2H, q), 1.44 (3H, t).

Production Example 5 (5)

A mixture of 0.30 g of 2-(6-chloro-3-ethylsulfonylpyridin-2-yl)-5-(trifluoromethylsulfanyl)benzoxazole, 0.14 ml of tetrahydrofurfurylamine, 0.24 ml of diisopropylethylamine and 0.5 ml of NMP was stirred at room temperature for 1 day. Water was added to the reaction mixture, and the mixture was extracted with ethyl acetate. The organic layer was dried over anhydrous sodium sulfate and concentrated under reduced pressure to produce 0.28 g of [5-ethylsulfonyl-6-(5-trifluoromethylsulfinylbenzoxazol-2-yl)-pyridin-2-yl]-(tetrahydrofuran-2-ylmethyl)-amine (hereinafter, referred to as Compound of Present Invention 36)

Compound of Present Invention 36

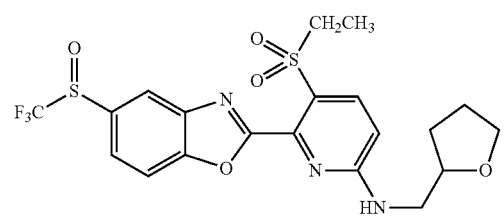 [SMILES: CCS(=O)(=O)c1ccc(NCC2CCCO2)nc1-c1nc2cc(S(=O)C(F)(F)F)ccc2o1]

$^1$H-NMR (CDCl$_3$) δ: 8.30 (1H, s), 8.07 (1H, d), 7.89-7.84 (2H, m), 6.65 (1H, d), 5.67 (1H, s), 4.12-4.10 (1H, m), 3.91-3.88 (1H, m), 3.79-3.73 (4H, m), 3.39-3.32 (1H, m), 2.06-2.01 (1H, m), 1.98-1.90 (2H, m), 1.65-1.60 (1H, m), 1.38 (3H, t).

Production Example 6 (1)

To a mixture of 10.0 g of 3,6-dichloropicolinic acid, 0.16 ml of DMF and 90 mL of toluene was added 7.20 ml of thionyl chloride, and the mixture was stirred under heating reflux for 2 hours. The reaction mixture cooled to room temperature was concentrated under reduced pressure to produce 10.88 g of 3,6-dichloropicolinoyl chloride.

A mixture of 3, 6-dichloropicolinoyl chloride produced above and 60 ml of THF was added to a mixture of 8.79 g of 2-amino-4-trifluoromethylsulfanylphenol and 40 ml of THF, under ice cooling, and the mixture was stirred at room temperature for 3 hours. Water and a saturated aqueous sodium bicarbonate solution were added to the reaction mixture, under ice cooling, and the mixture was extracted with ethyl acetate. The organic layer was dried over anhydrous sodium sulfate and concentrated under reduced pressure. The resulting residue was subjected to a silica gel column chromatography to produce 16.22 g of 3,6-dichloro-N-[2-hydroxy-5-(trifluoromethyl)phenyl]picolinamide.

3,6-Dichloro-N-[2-hydroxy-5-(trifluoromethyl)phenyl]picolinamide

$^1$H-NMR (CDCl$_3$) δ: 9.96 (1H, s), 8.82 (1H, s), 7.89 (1H, d), 7.62 (1H, d), 7.52 (1H, d), 7.44 (1H, dd), 7.14 (1H, d).

Production Example 6 (2)

A mixture of 10.0 g of 3,6-dichloro-N-[2-hydroxy-5-(trifluoromethyl)phenyl]picolinamide, 1.08 g of p-toluenesulfonic acid monohydrate and 40 ml of xylene was stirred under heating reflux for 3 hours while dehydrating using a Dean-Stark apparatus. Water and a saturated aqueous sodium bicarbonate solution were added to the reaction mixture cooled to room temperature, and the mixture was extracted with ethyl acetate. The organic layer was dried over anhydrous sodium sulfate and concentrated under reduced pressure. To the resulting residue was added 20 mL of isopropanol, and the mixture was stirred at 60° C. for 2 hours and at room temperature for 1 hour. The precipitated solid was filtered to produce 6.19 g of 2-(3,6-dichloropyridin-2-yl)-5-(trifluoromethyl)benzoxazole.

2-(3,6-Dichloropyridin-2-yl)-5-(trifluoromethyl)benzoxazole

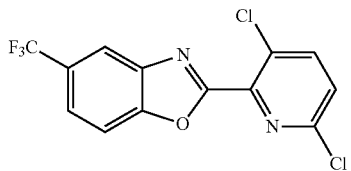 [SMILES: FC(F)(F)c1ccc2oc(-c3nc(Cl)ccc3Cl)nc2c1]

$^1$H-NMR (CDCl$_3$) δ:8.22 (1H, s), 7.92 (1H, d), 7.81 (1H, d), 7.75 (1H, d), 7.49 (1H, d).

Production Example 6 (3)

To a mixture of 7.50 g of 2-(3,6-dichloropyridin-2-yl)-5-(trifluoromethyl)benzoxazole and 32 ml of THF was added 1.08 g of 55% sodium hydride (oily), then 1.67 ml of ethyl mercaptan was added thereto over 30 minutes, under ice cooling, and the mixture was stirred at room temperature for 3 hours. The reaction mixture was added to ice water, and the precipitated solid was filtered. The resulting solid was washed with water and hexane and dried under reduced pressure to produce 6.46 g of 2-(6-chloro-3-ethylsulfanylpyridin-2-yl)-5-(trifluoromethyl)benzoxazole.

2-(6-Chloro-3-ethylsulfanylpyridin-2-yl)-5-(trifluoromethyl)benzoxazole

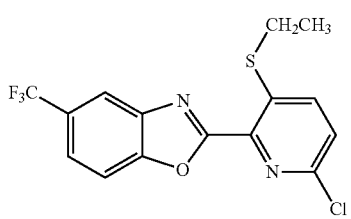 [SMILES: CCSc1ccc(Cl)nc1-c1nc2cc(C(F)(F)F)ccc2o1]

$^1$H-NMR (CDCl$_3$) δ: 8.23 (1H, s), 7.80 (1H, d), 7.71 (1H, d), 7.44 (1H, d), 3.06 (2H, q), 1.47 (3H, t).

Production Example 6 (4)

To a mixture of 2.0 g of 2-(6-chloro-3-ethylsulfanylpyridin-2-yl)-5-(trifluoromethyl)benzoxazole and 20 ml of chloroform was added 2.82 g of m-chloroperbenzoic acid (purity of 65% or more) under ice cooling, and the mixture was stirred at room temperature overnight. A 10% aqueous sodium thiosulfate solution and a saturated sodium bicarbonate solution were added to the reaction mixture, and the mixture was extracted with chloroform. The organic layer was dried over anhydrous sodium sulfate and concentrated under reduced pressure to produce 2.04 g of 2-(6-chloro-3-ethylsulfonylpyridin-2-yl)-5-(trifluoromethyl)benzoxazole.

2-(6-Chloro-3-ethylsulfonylpyridin-2-yl)-5-(trifluoromethyl)benzoxazole

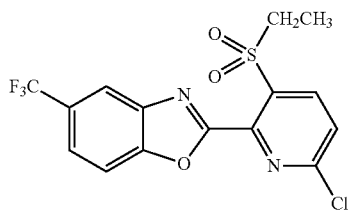 [SMILES: CCS(=O)(=O)c1ccc(Cl)nc1-c1nc2cc(C(F)(F)F)ccc2o1]

$^1$H-NMR (CDCl$_3$) δ: 8.53 (1H, d), 8.15 (1H, s), 7.83-7.72 (3H, m), 4.02 (2H, q), 1.44 (3H, t).

Production Example 6 (5)

To a mixture of 0.20 g of 2-(6-chloro-3-ethylsulfonylpyridin-2-yl)-5-(trifluoromethyl)benzoxazole, 77 mg of 6-chloro-3-pyridinemethylamine and 2 ml of NMP was added 79 mg of diisopropylethylamine, and the mixture was stirred at room temperature for 5 hours. Thereafter, 90 mg of 6-chloro-3-pyridinemethylamine was added thereto, and the mixture was stirred at room temperature overnight. Water was added to the reaction mixture, under ice cooling, and the mixture was extracted with ethyl acetate. The organic layer was dried over anhydrous sodium sulfate and concentrated under reduced pressure. The resulting residue was subjected to a silica gel column chromatography to produce 0.22 g of (6-chloropyridin-3-yl)-[5-ethylsulfonyl-6-(5-trifluoromethylbenzoxazol-2-yl)-pyridin-2-yl]amine (hereinafter, referred to as Compound of Present Invention 38).

Compound of Present Invention 38

$^1$H-NMR (CDCl$_3$) δ: 8.42 (1H, d), 8.15 (1H, d), 8.12 (1H, d), 7.78-7.67 (3H, m), 7.32 (1H, d), 6.65 (1H, d), 5.61 (1H, s), 4.69 (2H, d), 3.80 (2H, q), 1.39 (3H, t).

Production Example 7

To a mixture of 0.25 g of 2-(6-chloro-3-ethylsulfonylpyridin-2-yl)-5-(trifluoromethyl)benzoxazole, 80 mg of O-methylhydroxylamine hydrochloride and 2 ml of NMP was added 194 mg of triethylamine, and the mixture was stirred at room temperature for 4 hours, then stirred at 40° C. for 2 hours. To the reaction mixture cooled to room temperature were added 0.26 g of O-methylhydroxylamine hydrochloride and 0.87 g of diisopropylethylamine, and the mixture was stirred at 40° C. for 6 hours. Water was added to the reaction mixture, under ice cooling, and the mixture was extracted with ethyl acetate. The organic layer was dried over anhydrous sodium sulfate and concentrated under reduced pressure. The resulting residue was subjected to a silica gel column chromatography to produce 0.14 g of N-[5-ethylsulfonyl-6-(5-trifluoromethylbenzoxazol-2-yl]-pyridin-2-yl]amine-O-methylhydroxylamine (hereinafter, referred to as Compound of Present Invention 42).

Compound of Present Invention 42

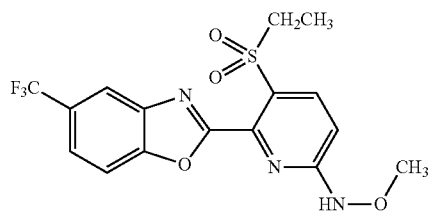 [SMILES: CCS(=O)(=O)c1ccc(NOC)nc1-c1nc2cc(C(F)(F)F)ccc2o1]

$^1$H-NMR (CDCl$_3$) δ: 8.39 (1H, dd), 8.12 (1H, d), 7.99 (1H, s), 7.75 (1H, d), 7.72 (1H, dd), 7.21 (1H, d), 3.89-3.83 (5H, m), 1.41 (3H, t).

Production Example 8 (1)

To a mixture of 1.0 g of 2-(6-chloro-3-ethylsulfonylpyridin-2-yl)-5-(trifluoromethyl)benzoxazole and 6.5 ml of NMP was added 1.55 ml of a 28% aqueous ammonia solution, and the mixture was stirred at room temperature for a day. To the reaction mixture was added 1.55 ml of a 28% aqueous ammonia solution, and the mixture was stirred at room temperature for a day. Water was added to the reaction mixture, and the precipitated solid was filtered, and dried under reduced pressure. The resulting residue was subjected to a silica gel column chromatography to produce 0.14 g of 5-ethylsulfonyl-6-(5-trifluoromethylbenzoxazol-2-yl)-pyridin-2-ylamine.

5-Ethylsulfonyl-6-(5-trifluoromethylbenzoxazol-2-yl)-pyridin-2-ylamine

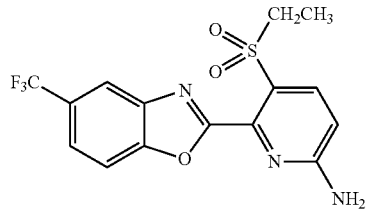 [SMILES: CCS(=O)(=O)c1ccc(N)nc1-c1nc2cc(C(F)(F)F)ccc2o1]

$^1$H-NMR (CDCl$_3$) δ: 8.18 (1H, d), 8.11 (1H, d), 7.75 (1H, d), 7.71 (1H, d), 6.74 (1H, d), 5.22 (2H, s), 3.82 (2H, q), 1.40 (3H, t).

Production Example 8 (2)

To a mixture of 0.20 g of 5-ethylsulfonyl-6-(5-trifluoromethylbenzoxazol-2-yl)-pyridin-2-ylamine and 5 ml of toluene was added 0.72 ml of N,N-dimethylformamide dimethyl acetal, and the mixture was stirred under heating reflux for 3 hours. The reaction mixture cooled to room temperature was concentrated under reduced pressure, and the resulting residue was subjected to silica gel column chromatography to produce 0.20 g of N'-[5-ethylsulfonyl-6-(5-trifluoromethylbenzoxazol-2-yl]-pyridin-2-yl]-N,N-dimethylformamidine (hereinafter, referred to as Compound of Present Invention 58).

Compound of Present Invention 58

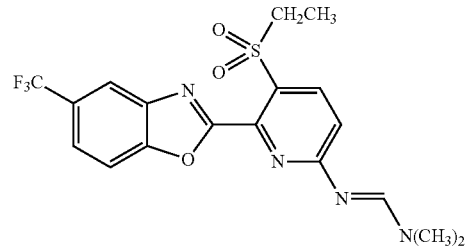 [SMILES: CCS(=O)(=O)c1ccc(/N=C/N(C)C)nc1-c1nc2cc(C(F)(F)F)ccc2o1]

$^1$H-NMR (CDCl$_3$) δ: 8.64 (1H, s), 8.22 (1H, d), 8.11 (1H, d), 7.75 (1H, d), 7.71 (1H, d), 7.16 (1H, d), 3.77 (2H, q), 3.16 (6H, s), 1.39 (3H, t).

The compounds described in the production examples described above and the compounds produced by the production method according to the method described in the production examples described above are shown in [Table 20] to [Table 23]. The compounds of the present invention represented by the formula (1B):

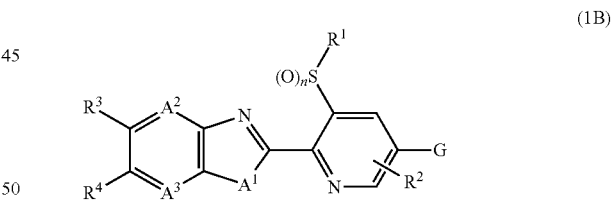

(1B)

wherein $A^1$, $A^2$, $A^3$, $R^1$, $R^2$, $R^3$, $R^4$, G and n represent the combinations shown in [Table 22] to [Table 23] shown below.

TABLE 22

| Compound of present invention | $A^1$ | $A^2$ | $A^3$ | $R^1$ | $R^2$ | $R^3$ | $R^4$ | G | n |
|---|---|---|---|---|---|---|---|---|---|
| 1 | NMe | CH | N | Et | H | CF$_3$ | H | ![](benzyl carbamate) •—NH—C(O)—O—CH$_2$—Ph | 2 |

TABLE 22-continued

| Compound of present invention | A¹ | A² | A³ | R¹ | R² | R³ | R⁴ | G | n |
|---|---|---|---|---|---|---|---|---|---|
| 2 | NMe | CH | N | Et | H | CF₃ | H | —N(S(O)₂CH₃)₂ | 2 |
| 3 | NMe | CH | N | Et | H | CF₃ | H | —N=CH—N(CH₃)₂ | 2 |
| 4 | NMe | CH | N | Et | H | CF | H | —NH—S(O)₂CH₃ | 2 |
| 5 | NMe | CH | N | Et | H | CF₃ | H | —NH—C(O)—N(CH₃)₂ | 2 |
| 6 | NMe | CH | N | Et | H | CF₃ | H | —NH—C(O)—C(O)—OCH₂CH₃ | 2 |
| 7 | NMe | CH | N | Et | H | CF₃ | H | —NH—C(O)-cyclopentyl | 2 |
| 8 | NMe | CH | N | Et | H | CF₃ | H | —NH—C(O)-cyclobutyl | 2 |
| 9 | NMe | CH | N | Et | H | CF₃ | H | —NH-cyclopropyl | 2 |
| 10 | NMe | CH | N | Et | H | CF₃ | H | —NH—C(O)-3-furyl | 2 |
| 11 | NMe | CH | N | Et | H | CF₃ | H | —N(C(O)OC(CH₃)₃)₂ | 2 |
| 12 | NMe | CH | N | Et | H | CF₃ | H | —NH—C(O)-2-furyl | 2 |
| 13 | NMe | CH | N | Et | H | CF₃ | H | —N(S(O)₂CH₃)(CH₃) | 2 |
| 14 | NMe | CH | N | Et | H | CF₃ | H | —NH—C(O)—C(O)—OCH₃ | 2 |

TABLE 22-continued

| Compound of present invention | A¹ | A² | A³ | R¹ | R² | R³ | R⁴ | G | n |
|---|---|---|---|---|---|---|---|---|---|
| 15 | NMe | CH | N | Et | H | CF₃ | H | •—NH—HN—C(=O)—OCH₃ | 2 |

TABLE 23

| Compound of present invention | A¹ | A² | A³ | R¹ | R² | R³ | R⁴ | G | n |
|---|---|---|---|---|---|---|---|---|---|
| 16 | NMe | CH | N | Et | H | CF₃ | H | •—NH—C(=O)—C(=O)—N(CH₃)₂ | 2 |
| 17 | NMe | CH | N | Et | H | CF₃ | H | •—N(cyclopropyl)—C(=O)—CH₃ | 2 |
| 18 | NMe | CH | N | Et | H | CF₃ | H | •—N(cyclopropyl)—C(=O)—OCH₃ | 2 |
| 19 | NMe | CH | N | Et | H | CF₃ | H | •—NH—NH₂ | 2 |
| 20 | NMe | CH | N | Et | H | CF₃ | H | •—NH—CH₂—(tetrahydrofuran-3-yl) | 2 |
| 21 | NMe | CH | N | Et | H | CF₃ | H | •—NH—CH₂—(6-chloropyridin-3-yl) | 2 |
| 22 | NMe | CH | N | Et | H | CF₃ | H | •—NH—C(=O)—cyclopropyl | 2 |
| 23 | NMe | CH | N | Et | H | CF₃ | H | •—NH—C(=O)—(tetrahydrofuran-2-yl) | 2 |
| 24 | NMe | CH | N | Et | H | CF₃ | H | •—NH—C(=O)—(pyridin-2-yl) | 2 |
| 25 | NMe | CH | N | Et | H | CF₃ | H | •—NH—CH₂—phenyl | 2 |

TABLE 23-continued

| Compound of present invention | A¹ | A² | A³ | R¹ | R² | R³ | R⁴ | G | n |
|---|---|---|---|---|---|---|---|---|---|
| 26 | NMe | CH | N | Et | H | $CF_3$ | H | 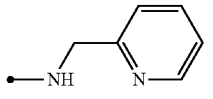 | 2 |
| 27 | NMe | CH | N | Et | H | $CF_3$ | H | 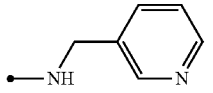 | 2 |
| 28 | O | CH | CH | Et | H | $CF_3S(O)_2$ | H | 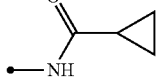 | 2 |
| 29 | O | CH | CH | Et | H | $CF_3S(O)_2$ | H | 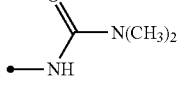 | 2 |
| 47 | O | CH | CH | Et | H | $CF_3S(O)$ | H | 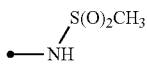 | 2 |

The compounds of the present invention represented by the formula (1C):

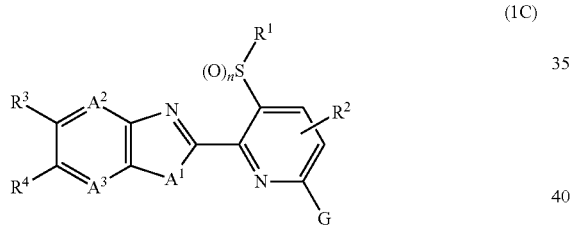

wherein A¹, A², A³, R¹, R², R³, R⁴, G and n represent the combinations shown in [Table 24] to [Table 25] shown below.

TABLE 24

| Compound of present invention | A¹ | A² | A³ | R¹ | R² | R³ | R⁴ | G | n |
|---|---|---|---|---|---|---|---|---|---|
| 30 | NMe | CH | N | Et | H | $CF_3$ | H | 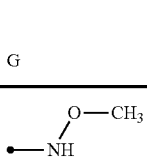 | 2 |
| 31 | NMe | CH | N | Et | H | $CF_3$ | H | 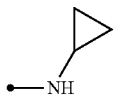 | 2 |
| 32 | O | CH | CH | Et | H | $CF_3S(O)$ | H | 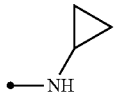 | 2 |

TABLE 24-continued

| Compound of present invention | A¹ | A² | A³ | R¹ | R² | R³ | R⁴ | G | n |
|---|---|---|---|---|---|---|---|---|---|
| 33 | O | CH | CH | Et | H | CF$_3$S(O) | H | -NH-NH-C(=O)-OCH$_3$ | 2 |
| 34 | O | CH | CH | Et | H | CF$_3$S(O) | H | -NH-CH$_2$-phenyl | 2 |
| 35 | O | CH | CH | Et | H | CF$_3$S | H | -NH-(4-pyridyl) | 2 |
| 36 | O | CH | CH | Et | H | CF$_3$S(O) | H | -NH-CH$_2$-(tetrahydrofuran-2-yl) | 2 |
| 37 | O | CH | CH | Et | H | CF$_3$S(O) | H | -NH-CH$_2$-(tetrahydrofuran-3-yl) | 2 |
| 38 | O | CH | CH | Et | H | CF$_3$ | H | -NH-CH$_2$-(6-chloropyridin-3-yl) | 2 |
| 39 | O | CH | CH | Et | H | CF$_3$ | H | -N(CH$_3$)-C(=O)-cyclopropyl | 2 |
| 40 | O | CH | CH | Et | H | CF$_3$ | H | -NH-S(O)$_2$CH$_3$ | 2 |
| 41 | O | CH | CH | Et | H | CF$_3$S(O) | H | -N=S(CH$_2$CH$_3$)$_2$ | 2 |
| 42 | O | CH | CH | Et | H | CF$_3$ | H | -NH-O-CH$_3$ | 2 |
| 43 | O | CH | CH | Et | H | CF$_3$ | H | -N(CH$_3$)-O-CH$_3$ | 2 |
| 44 | O | CH | CH | Et | H | CF$_3$S | H | -NH-C(=O)-cyclopropyl | 2 |

TABLE 25

| Compound of present invention | A¹ | A² | A³ | R¹ | R² | R³ | R⁴ | G | n |
|---|---|---|---|---|---|---|---|---|---|
| 45 | O | CH | CH | Et | H | CF$_3$S(O) | H | •—NH—C(O)-cyclopropyl | 2 |
| 46 | O | CH | CH | Et | H | CF$_3$S(O) | H | •—NH—CH$_2$-(6-chloropyridin-3-yl) | 2 |
| 48 | O | CH | CH | Et | H | CF$_3$S(O) | H | •—NH—S(O)$_2$CH$_3$ | 2 |
| 49 | O | CH | CH | Et | H | CF$_3$S(O) | H | •—NH—S(O)$_2$CF$_3$ | 2 |
| 50 | O | CH | CH | Et | H | CF$_3$S | H | •—N=C(Ph)$_2$ | 0 |
| 51 | O | CH | CH | Et | H | CF$_3$S(O) | H | •—N=C(Ph)$_2$ | 2 |
| 52 | O | CH | CH | Et | H | CF$_3$ | H | •—NH—S(O)$_2$CH$_3$ | 0 |
| 53 | O | CH | CH | Et | H | CF$_3$ | H | •—N=C(Ph)$_2$ | 0 |
| 54 | O | CH | CH | Et | H | CF$_3$ | H | •—N=C(Ph)$_2$ | 2 |
| 55 | O | CH | CH | Et | H | CF$_3$ | H | •—NH—S(O)$_2$CF$_3$ | 0 |
| 56 | O | CH | CH | Et | H | CF$_3$ | H | •—N(CH$_3$)—S(O)$_2$CF$_3$ | 0 |
| 57 | O | CH | CH | Et | H | CF$_3$ | H | •—N(CH$_3$)—S(O)$_2$CF$_3$ | 2 |
| 58 | O | CH | CH | Et | H | CF$_3$ | H | •—N=CH—N(CH$_3$)$_2$ | 2 |

TABLE 25-continued

| Compound of present invention | A¹ | A² | A³ | R¹ | R² | R³ | R⁴ | G | n |
|---|---|---|---|---|---|---|---|---|---|
| 59 | O | CH | CH | Et | H | CF₃S | H | 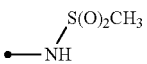 | 0 |
| 60 | O | CH | CH | Et | H | CF₃S(O) | H | 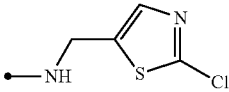 | 2 |

¹H-NMR data of the compound of the present invention shown in [Table 22] to [Table 25] is shown below.

Compound of Present Invention 1
¹H-NMR (CDCl₃) δ: 9.06 (1H, d), 8.74 (1H, d), 8.59 (1H, d), 8.29 (1H, d), 7.46-7.37 (5H, m), 7.30 (1H, brs), 5.28 (2H, s), 3.86 (3H, s), 3.83 (2H, q), 1.35 (3H, t).

Compound of Present Invention 6
¹H-NMR (CDCl₃) δ: 9.39 (1H, d), 9.29 (1H, brs), 8.78-8.76 (2H, m), 8.31 (1H, dd), 4.50 (2H, q), 3.93-3.87 (5H, m), 1.48 (3H, t), 1.40 (3H, t).

Compound of Present Invention 7
¹H-NMR (CDCl₃) δ: 9.51 (1H, d), 8.75 (1H, d), 8.59 (1H, d), 8.30 (1H, d), 8.29 (1H, s), 3.94 (2H, q), 3.89 (3H, s), 2.84-2.74 (1H, m), 2.02-1.87 (4H, m), 1.84-1.74 (2H, m), 1.68-1.58 (2H, m), 1.40 (3H, t).

Compound of Present Invention 8
¹H-NMR (CDCl₃) δ: 9.52 (1H, d), 8.76 (1H, d), 8.58 (1H, d), 8.31 (1H, d), 8.09 (1H, s), 3.94 (2H, q), 3.89 (3H, s), 3.31-3.20 (1H, m), 2.48-2.37 (2H, m), 2.31-2.20 (2H, m), 2.07-1.92 (2H, m), 1.40 (3H, t).

Compound of Present Invention 9
¹H-NMR (CDCl₃) δ: 8.72 (1H, d), 8.42 (1H, d), 8.27 (1H, d), 7.77 (1H, d), 4.83 (1H, brs), 3.85-3.78 (5H, m), 2.66-2.58 (1H, m), 1.37 (3H, t), 1.0-0.92 (2H, m), 0.69-0.63 (2H, m)

Compound of Present Invention 10
¹H-NMR (CDCl₃) δ: 9.62 (1H, s), 8.77 (1H, d), 8.67 (1H, d), 8.39-8.36 (1H, m), 8.31 (1H, d), 8.18 (1H, d), 7.54-7.52 (1H, m), 6.84 (1H, d), 3.96 (2H, q), 3.92 (3H, s), 1.39 (3H, t)

Compound of Present Invention 11
¹H-NMR (CDCl₃) δ: 8.80 (1H, d), 8.77 (1H, d), 8.37 (1H, d), 8.32 (1H, d), 3.93-3.84 (5H, m), 1.51 (18H, s), 1.38 (3H, t).

Compound of Present Invention 12
¹H-NMR (CDCl₃) δ: 9.59 (1H, d), 8.83 (1H, s), 8.79-8.75 (2H, m), 8.31 (1H, d), 7.60 (1H, d), 7.38 (1H, d), 6.63 (1H, dd), 3.93 (2H, q), 3.92 (3H, s), 1.39 (3H, t).

Compound of Present Invention 13
¹H-NMR (CDCl₃) δ: 9.05 (1H, d), 8.77 (1H, d), 8.45 (1H, d), 8.31 (1H, d), 3.95-3.86 (5H, m), 3.52 (3H, s), 3.05 (3H, s), 1.40 (3H, t).

Compound of Present Invention 14
¹H-NMR (CDCl₃) δ: 9.46 (1H, d), 9.44 (1H, brs), 8.78-8.75 (2H, m), 8.31 (1H, d), 4.04 (3H, s), 3.93 (2H, q), 3.91 (3H, s), 1.40 (3H, t).

Compound of Present Invention 15
¹H-NMR (CDCl₃) δ: 8.74 (1H, d), 8.53 (1H, d), 8.28 (1H, d), 7.89 (1H, d), 6.80 (1H, brs), 6.32 (1H, d), 3.87-3.79 (8H, m), 1.36 (3H, t).

Compound of Present Invention 16
¹H-NMR (CDCl₃) δ: 10.20 (1H, s), 9.31 (1H, d), 8.91 (1H, d), 8.76 (1H, dd), 8.31 (1H, dd), 3.91-3.85 (5H, m), 3.56 (3H, s), 3.17 (3H, s), 1.39 (3H, t).

Compound of Present Invention 17
¹H-NMR (CDCl₃) δ: 9.00 (1H, d), 8.76 (1H, d), 8.44 (1H, d), 8.30 (1H, d), 3.92 (3H, s), 3.87 (2H, q), 3.28-3.21 (1H, m), 2.51 (3H, s), 1. (3H, t), 1.28-1.20 (2H, m), 0.80-0.74 (2H, m).

Compound of Present Invention 18
¹H-NMR (CDCl₃) δ: 9.04 (1H, d), 8.76 (1H, d), 8.48 (1H, d), 8.30 (1H, d), 3.91 (3H, s), 3.89-3.82 (5H, m), 3.15-3.12 (1H, m), 1.39 (3H, t), 1.09 (2H, m), 0.71-0.65 (2H, m).

Compound of Present Invention 19
¹H-NMR (CDCl₃) δ: 8.72 (1H, d), 8.47 (1H, d), 8.28 (1H, d), 7.88 (1H, d) 6.12 (1H, brs), 3.86-3.77 (7H, m), 1.36 (3H, t).

Compound of Present Invention 20
¹H-NMR (CDCl₃) δ: 8.72 (1H, dd), 8.29-8.26 (2H, m), 7.57 (1H, d 1H, t), 4.01-3.68 (9H, m), 3.28 (2H, dd), 2.67-2.58 (1H, m), 2.22-2.13 (1H, m), 1.77-1.68 (1H, m), 1.36 (3H, t).

Compound of Present Invention 21
¹H-NMR (CDCl₃) δ: 8.72 (1H, s), 8.42 (1H, s), 8.30 (1H, d), 8.27 (1H, 7.69 (1H, dd), 7.61 (1H, d), 7.35 (1H, d), 5.44 (1H, t), 4.51 (2H, d), 3.89-3.77 (5H, m), 1.29 (3H, t).

Compound of Present Invention 22
¹H-NMR (CDCl₃) δ: 9.42 (1H, d), 9.19 (1H, s), 8.75 (1H, d), 8.67 (1H, d), 8.30 (1H, d), 3.93 (2H, q), 3.88 (3H, s), 1.69-1.62 (1H, m), 1.39 (3H, t), 1.14-1.10 (2H, m), 0.93-0.87 (2H, m).

Compound of Present Invention 23
¹H-NMR (CDCl₃) δ: 9.39 (1H, d), 9.03 (1H, brs), 8.75 (1H, d), 8.71 (1H, d), 8.30 (1H, d), 4.55 (1H, dd), 4.14-4.07 (1H, m), 4.02-3.97 (1H, m), 3.92-3.85 (5H, m), 2.49-2.38 (1H, m), 2.26-2.17 (1H, m), 2.08-1.93 (2H, m), 1.39 (3H, t).

Compound of Present Invention 24
¹H-NMR (CDCl₃) δ: 10.53 (1H, s), 9.51 (1H, d), 8.94 (1H, d), 8.76 (1H, d), 8.71-8.68 (1H, m), 8.37-8.33 (1H, m), 8.31 (1H, d), 8.03-7.98 (1H, m) 7.62-7.58 (1H, m), 3.92-3.84 (5H, m), 1.42 (3H, t)

Compound of Present Invention 25
¹H-NMR (CDCl₃) δ: 8.71 (1H, d), 8.32-8.29 (1H, m), 8.25 (1H, d), 7.59-7.57 (1H, m), 7.42-7.32 (5H, m), 5.00-4.88 (1H, m), 4.52-4.47 (2H, m), 3.83 (3H, s), 3.76 (2H, q), 1.26 (3H, t)

Compound of Present Invention 26
¹H-NMR (CDCl₃) δ: 8.71 (1H, d), 8.65-8.61 (1H, m), 8.42-8.40 (1H, m), 8.26 (1H, d), 7.78-7.72 (1H, m), 7.65 (1H, d), 7.35 (1H, d), 7.31-7.27 (1H, m), 6.14-6.08 (1H, m), 4.59 (2H, d), 3.86-3.76 (5H, m), 1.34 (3H, t).

Compound of Present Invention 27
¹H-NMR (CDCl₃) δ: 8.71 (1H, d), 8.67 (1H, d), 8.58 (1H, dd), 8.32 (1H, d), 8.26 (1H, d), 7.74-7.70 (1H, m), 7.62 (1H, d), 7.34 (1H, dd), 5.30 (1H, t), 4.53 (2H, d), 3.83 (3H, s), 3.79 (2H, q), 1.28 (3H, t).

Compound of Present Invention 28
¹H-NMR (DMSO-D₆) δ: 11.25 (1H, s), 9.22 (1H, d), 8.89 (1H, d), 8.80 (1H, d), 8.38 (1H, d), 8.31 (1H, dd), 3.96 (2H, q), 1.94-1.84 (1H, m), 1.28 (3H, t), 1.02-0.88 (4H, m)

Compound of Present Invention 29
¹H-NMR (DMSO-D₆) δ: 1.83 (1H, brs), 9.13 (1H, d), 8.90 (1H, d), 8.80 (1H, d), 8.38 (1H, d), 8.31 (1H, dd), 3.99 (2H, q), 3.40-3.27 (6H, m), 1.32 (3H, t).

Compound of Present Invention 30
¹H-NMR (CDCl₃) δ: 8.73 (1H, dd), 8.29 (1H, dd), 8.14 (1H, d), 6.73 (1H, d), 5.18 (3H, s), 3.85 (3H, s), 3.58 (2H, q), 1.31 (3H, t).

Compound of Present Invention 31
¹H-NMR (CDCl₃) δ: 8.72 (1H, s), 8.28 (1H, s), 8.19 (1H, d), 6.97 (1H, d), 5.65 (1H, brs), 3.83 (3H, s), 3.58 (2H, q), 2.70-2.62 (1H, m), t), 0.98-0.92 (2H, m), 0.70-0.64 (2H, m).

Compound of Present Invention 32
¹H-NMR (CDCl₃) δ: 8.29 (1H, s), 8.24 (1H, d), 7.91-7.81 (2H, m) H, d), 5.79 (1H, s), 3.78 (2H, q), 2.70-2.61 (1H, m), 1.40 (3H, t), 0.98-0.90 (2H, m), 0.70-0.62 (2H, m).

Compound of Present Invention 33
¹H-NMR (CDCl₃) δ: 8.31 (1H, s), 8.26 (1H, d), 7.92-7.80 (2H, m) H, s), 7.14 (1H, s), 6.97 (1H, d), 3.85-3.65 (5H, m), 1.39 (3H, t)

Compound of Present Invention 34
¹H-NMR (CDCl₃) δ: 8.30 (1H, s), 8.11 (1H, d), 7.88-7.85 (2H, m) 0.30 (5H, m), 6.62 (1H, d), 5.74 (1H, s), 4.63 (2H, d), 3.77 (2H, 3H, t).

Compound of Present Invention 35
¹H-NMR (DMSO-DE) δ: 10.00 (1H, s), 8.38-8.36 (3H, m), 8.11 (1H, d), 7.97-7.95 (1H, m), 7.87-7.84 (3H, m), 7.22 (1H, d), 3.05 (2H, q), 1.27 (3H, t).

Compound of Present Invention 37
¹H-NMR (CDCl₃) δ: 8.30 (1H, s), 8.12 (1H, d), 7.93-7.84 (2H, m), 6.64 (1H, d), 5.47 (1H, brs), 3.99-3.91 (1H, m), 3.88-3.82 (1H, m), 3.80-3.71 (3H, m), 3.68-3.62 (1H, m), 3.49-3.39 (2H, m), 2.67-2.56 (1H, m), 2.18-2.07 (1H, m), 1.75-1.64 (1H, m), 1.39 (3H, t).

Compound of Present Invention 39
¹H-NMR (CDCl₃) δ: 8.44 (1H, d), 8.15 (1H, t), 8.12 (1H, d), 7.78-7.75 (2H, m), 3.91 (2H, q), 3.72 (3H, s), 2.01-1.99 (1H, m), 1.42 (3H, t), 1.22-1.20 (2H, m), 1.00-0.98 (2H, m)

Compound of Present Invention 40
¹H-NMR (DMSO-D₆) δ: 11.78 (1H, s), 8.43 (2H, d), 8.17 (1H, d), 7.95 (1H, d), 7.40 (1H, d), 3.79 (2H, q), 3.42 (3H, s), 1.25 (3H, t).

Compound of Present Invention 41
¹H-NMR (CDCl₃) δ: 8.28 (1H, s), 7.89 (1H, d), 7.85 (2H, d), 6.83 (1H, d), 3.67 (2H, q), 3.09-3.01 (4H, m), 1.38-1.36 (9H, m).

Compound of Present Invention 43
¹H-NMR (CDCl₃) δ: 8.25 (1H, d), 8.11 (1H, t), 7.75 (1H, d), 7.71 (1H, dd), 7.21 (1H, d), 3.82 (3H, s), 3.79 (2H, q), 3.44 (3H, s), 1.38 (3H, t).

Compound of Present Invention 44
¹H-NMR (CDCl₃) δ: 8.69 (1H, s), 8.56 (1H, d), 8.48 (1H, d), 8.17 (1H, d), 7.76 (1H, dd), 7.69 (1H, d), 3.89 (2H, q), 1.61-1.59 (1H, m), 1.41 (3H, t), 1.19-1.15 (2H, m), 0.99-0.97 (2H, m).

Compound of Present Invention 45
¹H-NMR (CDCl₃) δ: 9.07 (1H, s), 8.57 (1H, d), 8.47 (1H, d), 8.32 (1H, s), 7.86 (1H, d), 7.78 (1H, d), 3.86 (2H, q), 1.71-1.69 (1H, m), 1.40 (3H, t) 1.18-1.14 (2H, m), 0.98-0.96 (2H, m).

Compound of Present Invention 46
¹H-NMR (CDCl₃) δ: 8.40 (1H, d), 8.31 (1H, s), 8.11 (1H, d), 7.89 (1H, dd), 7.86 (1H, dd), 7.68 (1H, dd), 7.31 (1H, d), 6.66 (1H, d), 5.77 (1H, s), 4.68 (2H, d), 3.79 (2H, q), 1.39 (3H, t).

Compound of Present Invention 47
¹H-NMR (DMSO-D₆) δ: 9.98 (1H, s), 9.01 (1H, d), 8.88 (1H, d), 8.77 (H), 8.36 (1H, d), 8.30 (1H, d), 3.91 (2H, q), 1.27 (3H, t).

Compound of Present Invention 48
¹H-NMR (CDCl₃) δ: 8.49 (1H, d), 8.35 (1H, s), 7.90 (2H, s), 7.48 (1H, 3.94 (2H, q), 3.40 (3H, s), 1.43 (3H, t).

Compound of Present Invention 49
¹H-NMR (DMSO-D₆) δ: 8.47 (1H, d), 8.25 (1H, dd), 8.09 (1H, d), dd), 7.36 (1H, d), 3.66 (2H, q), 1.22 (3H, t).

Compound of Present Invention 50
¹H-NMR (CDCl₃) δ: 8.24 (1H, s), 7.83 (2H, d), 7.69 (2H, d), 7.52-7.50 (2H, m), 7.42 (2H, t), 7.29-77.1 (5H, m), 6.58 (1H, d), 2.96 (2H, q), 1.38 (3H, t).

Compound of Present Invention 51
¹H-NMR (CDCl₃) δ: 8.32 (1H, s), 8.24 (1H, d), 7.89-7.84 (2H, m) 0.44 (10H, m), 6.80 (1H, d), 3.91 (2H, q), 1.36 (3H, t).

Compound of Present Invention 52
¹H-NMR (CDCl₃) δ: 8.23 (1H, t), 7.82 (1H, d), 7.78 (1H, d), 7.72 (1H, dd), 7.49 (1H, d), 7.19 (1H, s), 3.27 (3H, s), 3.05 (2H, q), 1.44 (3H, t).

Compound of Present Invention 53
¹H-NMR (CDCl₃) δ: 8.20 (1H, t), 7.84 (2H, d), 7.74 (1H, d), 7.66 (1H, dd), 7.52-7.51 (2H, m), 7.42 (2H, t), 7.30-7.22 (5H, m), 6.59 (1H, d), 2.96 (2H, q), 1.37 (3H, t).

Compound of Present Invention 54
¹H-NMR (CDCl₃) δ: 8.23 (1H, d), 8.11 (1H, t), 7.76-7.70 (2H, m), 7.51-7.35 (10H, m), 6.77 (1H, d), 3.93 (2H, q), 1.36 (3H, t).

Compound of Present Invention 56
¹H-NMR (CDCl₃) δ: 8.24 (1H, t), 7.80-7.78 (2H, m), 7.72 (1H, dd), 7.64 (1H, d), 3.70 (3H, t), 3.07 (2H, q), 1.47 (3H, t).

Compound of Present Invention 57
¹H-NMR (CDCl₃) δ: 8.56 (1H, d), 8.16 (1H, s), 8.00 (1H, d), 7.79-7.78 (2H, m), 3.96 (2H, q), 3.72 (3H, s), 1.44 (3H, t).

Compound of Present Invention 59
¹H-NMR (CDCl₃) δ: 8.26 (1H, s), 7.82 (1H, d, J=8.9 Hz), 7.73 (2H, dd, J=2.5, 1.1 Hz), 7.48 (1H, d, J=8.9 Hz), 3.26 (3H, s), 3.05 (2H, q, J=7.4 Hz), 1.45 (3H, t, J=7.4 Hz).

Compound of Present Invention 60
¹H-NMR (CDCl3) δ: 8.33 (1H, d, J=0.7 Hz), 8.13 (1H, d, J=8.8 Hz), 7.91 (1H, dd, J=8.6, 0.5 Hz), 7.88 (1H, dd, J=8.6, 0.9 Hz), 7.48 (1H, s), 6.69 (1H, d, J=9.1 Hz), 5.77 (1H, t, J=6.0 Hz), 4.80 (2H, d, J=5.9 Hz), 3.81 (2H, q, J=7.5 Hz), 1.40 (3H, t, J=7.4 Hz).

Next, formulation examples of the compound of the present invention are shown. The part means part by weight.

Formulation Example 1

10 parts of any one of Compounds of Present Invention 1 to 60 is dissolved in a mixture of 35 parts of xylene and 35 parts of N,N-dimethylformamide, 14 parts of polyoxyethylenestyrylphenyl ether and 6 parts of calcium dodecylbenzenesulfonate are added thereto. The mixture is mixed to produce each emulsifiable concentrate.

Formulation Example 2

4 parts of sodium lauryl sulfate, 2 parts of calcium lignosulfonate, 20 parts of synthetic hydrous silicon oxide fine powder and 54 parts of diatomaceous earth are mixed, and 20 parts of any one of Compounds of Present Invention 1 to 60 is further added thereto. The mixture is mixed to produce each wettable powder.

Formulation Example 3

1 part of synthetic hydrous silicon oxide fine powder, 2 parts of calcium lignosulfonate, 30 parts of bentonite and 65 parts of kaolin clay are added to 2 parts of any one of Compounds of Present Invention 1 to 60. Subsequently, an appropriate amount of water is added to this mixture, and the mixture is further stirred, granulated with a granulator, and forced-air dried to produce each granule.

Formulation Example 4

1 part of any one of Compounds of Present Invention 1 to 60 is dissolved in an appropriate amount of acetone, and 5 parts of synthetic hydrous silicon oxide fine powder, 0.3 parts of PAP and 93.7 parts of Fubasami clay are added thereto. The mixture is sufficiently stirred and mixed to evaporate and eliminate acetone to produce each dust formulation.

Formulation Example 5

35 parts of a mixture of polyoxyethylene alkyl ether sulfate ammonium salt and white carbon (weight ratio 1:1), 10 parts of any one of Compounds of Present Invention 1 to 60 and 55 parts of water are mixed, and finely pulverized by wet grinding method to produce each flowable.

Formulation Example 6

0.1 parts of any one of Compounds of Present Invention 1 to 60 is dissolved in 5 parts of xylene and 5 parts of trichloroethane, and the mixture is mixed with 89.9 parts of deodorized kerosene to produce each oil solution.

Formulation Example 7

10 mg of any one of Compounds of Present Invention 1 to 60 is dissolved in 0.5 ml of acetone, and this solution is applied to 5 g of solid feed powder for animal (solid feed powder for breeding CE-2, product of CLEA Japan, Inc.), and the mixture is uniformly mixed. Subsequently, acetone is evaporated to dryness to produce each poisonous bait.

Formulation Example 8

0.1 parts of any one of Compounds of Present Invention 1 to 60 and 49.9 parts of Neothiozol (Chuo Kasei Co., Ltd.) are filled into an aerosol can, and an aerosol valve is attached, then the container is filled with 25 parts of dimethyl ether and 25 parts of LPG and shaken, and an actuator is attached to produce an oil-based aerosol.

Formulation Example 9

0.6 parts of any one of Compounds of Present Invention 1 to 60, 0.01 parts of BHT (2, 6-di-tert-butyl-4-methylphenol), 5 parts of xylene, 3.39 parts of deodorized kerosene and 1 part of emulsifier {RHEODOL MO-60 (manufactured by Kao Corporation)} are mixed and dissolved, and the resulting solution and 50 parts of distilled water are filled into an aerosol container. A valve is attached to the container, then 40 parts of a propellant (LPG) is filled under pressure through the valve to produce an aqueous aerosol.

Formulation Example 10

0.1 g of any one of Compounds of Present Invention 1 to 60 is dissolved in 2 ml of propylene glycol, and a porous ceramic plate with a size of 4.0 cm×4.0 cm and 1.2 cm in thickness is impregnated with the solution to produce a heating type smoking agent.

Formulation Example 11

5 parts of any one of Compounds of Present Invention 1 to 60 and 95 parts of an ethylene-methyl methacrylate copolymer (a ratio of methyl methacrylate in the copolymer: 10% by weight, Acryft WD301, manufactured by SUMITOMO CHEMICAL Co., Ltd.) are melt-kneaded with a closed pressurizing kneader (manufactured by Moriyama Works), and the resulting kneaded matter is extruded from a molding machine through a molding die to produce a rod-shaped molded body with a size of 15 cm in length and 3 mm in diameter.

Formulation Example 12

5 parts of any one of Compounds of Present Invention 1 to 60 and 95 parts of a soft vinyl chloride resin are melt-kneaded with a closed pressurizing kneader (manufactured by Moriyama Works), and the resulting kneaded matter is extruded from a molding machine through a molding die to produce a rod-shaped molded body with a size of 15 cm in length and 3 mm in diameter.

Formulation Example 13

100 mg of any one of Compounds of Present Invention 1 to 60, 68.75 mg of lactose, 237.5 mg of corn starch, 43.75 mg of microcrystalline cellulose, 18.75 mg of polyvinylpyrrolidone, 28.75 mg of sodium carboxymethyl starch and 2.5 mg of magnesium stearate are mixed, and the resulting mixture was compressed to an appropriate size to produce a tablet.

Formulation Example 14

25 mg of any one of Compounds of Present Invention 1 to 60, 60 mg of lactose, 25 mg of corn starch, 6 mg of carmellose calcium and an appropriate amount of 5% hydroxypropyl methylcellulose are mixed, and the resulting mixture is filled into a hard shell gelatin capsule or a hydroxypropyl methylcellulose capsule to produce an encapsulated formulation.

Formulation Example 15

Distilled water is added to 1000 mg of any one of Compounds of Present Invention 1 to 60, 500 mg of fumaric acid, 2000 mg of sodium chloride, 150 mg of methylparaben, 50 mg of propylparaben, 25000 mg of granulated sugar, 13000 mg of sorbitol (70% solution), 100 mg of Veegum K (Vanderbilt Co.), 35 mg of flavor and 500 mg of colorant, such that a final volume is 100 ml, and the mixture is mixed to produce a suspension for oral administration.

Formulation Example 16

5% by weight of any one of Compounds of Present Invention 1 to 60 is dissolved in 5% by weight of polysorbate 85, 3% by weight of benzyl alcohol and 30% by weight of propylene glycol, and a phosphate buffer is added to this solution so as to have a pH of 6.0 to 6.5, then water is added until it reaches the final volume to produce a liquid formulation for oral administration.

Formulation Example 17

5% by weight of aluminum distearate is dispersed in 57% by weight of fractionated palm oil and 3% by weight of polysorbate 85 by heating. This dispersion is cooled to room temperature, and 25% by weight of saccharin is dispersed in an oily vehicle thereof. To the dispersion is distributed 10% by weight of any one of Compounds of Present Invention 1 to 60 to produce a paste formulation for oral administration.

Formulation Example 18

Any one of Compounds of Present Invention 1 to 60 in an amount of 5% by weight and 95% by weight of limestone filler are mixed, and a granule for oral administration is produced using wet granulation method.

Formulation Example 19

Any one of Compounds of Present Invention 1 to 60 in an amount of 5 parts is dissolved in 80 parts of diethylene glycol monoethyl ether, and 15 parts of propylene carbonate is mixed therewith to produce a spot-on solution.

Formulation Example 20

10 parts of any one of Compounds of Present Invention 1 to 60 is dissolved in 70 parts of diethylene glycol monoethyl ether, and 20 parts of 2-octyl dodecanol is mixed therewith to produce a pour-on solution.

Formulation Example 21

NIKKOL TEALS-42 (Nikko Chemicals Co., Ltd., 42% aqueous solution of triethanolamine lauryl sulfate) in an amount of 60 parts and 20 parts of propylene glycol are added to 0.5 parts of any one of Compounds of Present Invention 1 to 60, and the mixture is sufficiently stirred and mixed until it becomes a uniform solution, then 19.5 parts of water is added and further sufficiently stirred and mixed to produce a shampoo agent as a uniform solution.

Formulation Example 22

Any one of Compounds of Present Invention 1 to 60 in an amount of 0.15% by weight, 95% by weight of animal feed and 4.85% by weight of a mixture of secondary calcium phosphate, diatomaceous earth, Aerosil and carbonate (or chalk) are sufficiently stirred and mixed to produce a feed premix for animal.

Formulation Example 23

7.2 g of any one of Compounds of Present Invention 1 to 60 and 92.8 g of VOSCO S-55 (manufactured by Maruishi Pharmaceutical Co., Ltd.) are dissolved and mixed at 100° C., poured into a suppository mold, and cooled and solidified to produce a suppository.

Test Example 1

The formulations of Compounds of Present Invention 1 to 17, 19 to 27, 30 to 34, 36 to 39, 41 to 46, 48 to 49, 51, 54 and 57 as produced in Formulation Example 5 were diluted with water, so as to have a concentration of the active ingredient of 500 ppm, to prepare each test drug solution.

On the other hand, a cucumber seedling (the first true leaf stage) planted in a plastic cup was inoculated with about 30 *Aphis gossypii* (whole stage), and left for a day. The test drug solution was sprayed in an amount of 20 ml on the seedling.

Six days after spraying, the number of surviving *Aphis gossypii* parasitic on the leaves of the cucumber was examined, and the control value was calculated according to the following equation:

$$\text{Control value (\%)} = \{1-(Cb \times Tai)/(Cai \times Tb)\} \times 100$$

wherein the symbols represent as follows:
Cb: the number of insects in a non-treated section before treatment
Cai: the number of surviving parasitic insects in a non-treated section on observation
Tb: the number of insects in a treated section before treatment
Tai: the number of surviving parasitic insects in a treated section on observation
wherein the non-treated section refers to a section where the test drug solution prepared by diluting the formulation produced as in Formulation Example 5 but not containing the compound of the present invention with the same amount of water as in the treated section was sprayed.

As a result, in the treated section where the test drug solution containing each of Compounds of Present Invention 1 to 17, 19 to 27, 30 to 34, 36 to 39, 41 to 46, 48 to 49, 51, 54 and 57 was used, the control value was 90% or more.

Test Example 2

The formulations of Compounds of Present Invention 2, 4 to 5, 8 to 9, 13, 15 to 16, 19, 22 to 23, 30 to 33 and 41 as produced in Formulation Example 5 were diluted with water, so as to have a concentration of the active ingredient of 500 ppm, to prepare each test drug solution.

On the other hand, a cucumber seedling (the second true leaf stage) planted in a plastic cup was drenched at its foot with 5 ml of the test drug solution, and kept in a greenhouse at 25° C. for 7 days. On the cucumber leaf surface was inoculated about 30 *Aphis gossypii* (whole stage), and further kept in the greenhouse for 6 days, then the number of surviving *Aphis gossypii* parasitic on the leaves of the cucumber was examined, and the control value was calculated according to the following equation:

$$\text{Control value (\%)} = \{1-(Cb \times Tai)/(Cai \times Tb)\} \times 100$$

wherein the symbols represent as follows:
Cb: the number of insects in a non-treated section before treatment
Cai: the number of surviving parasitic insects in a non-treated section on observation
Tb: the number of insects in a treated section before treatment
Tai: the number of surviving parasitic insects in a treated section on observation wherein the non-treated section refers to a section where the test drug solution prepared by diluting the formulation produced as in Formulation Example 5 but not not containing the compound of the present invention with the same amount of water as in the treated section was sprayed.

As a result, in the treated section where the test drug solution containing each of Compounds of Present Invention 2, 4 to 5, 8 to 9, 13, 15 to 16, 19, 22 to 23, 30 to 33 and 41 was used, the control value was 90% or more.

Test Example 3

The formulations of Compounds of Present Invention 3, 15 to 16, 19, 22 to 23, 30 to 34, 36 to 39, 41 to 46, 48, 51 and 54 as produced in Formulation Example 5 were diluted with water, so as to have a concentration of the active ingredient of 500 ppm, to prepare each test drug solution.

On a rice seedling in the second leaf stage planted in a polyethylene cup was sprayed 10 ml of each test drug solution. After air-drying, 20 third-fourth instar larvae of *Nilaparvata lugens* were released, and kept in the greenhouse at 25° C. After 6 days, the number of surviving *Nilaparvata lugens* parasitic on the rice was examined, and the control value was calculated according to the following equation:

$$\text{Control value (\%)} = \{1-(Cb \times Tai)/(Cai \times Tb)\} \times 100$$

wherein the symbols represent as follows:

Cb: the number of insects in a non-treated section before treatment

Cai: the number of surviving parasitic insects in a non-treated section on observation Tb: the number of insects in a treated section before treatment Tai: the number of surviving parasitic insects in a treated section on observation wherein the non-treated section refers to a section where the test drug solution prepared by diluting the formulation produced as in Formulation Example 5 but not not containing the compound of the present invention with the same amount of water as in the treated section was sprayed.

As a result, in the treated section where the test drug solution containing each of Compounds of Present Invention 3, 15 to 16, 19, 22 to 23, 30 to 34, 36 to 39, 41 to 46, 48, 51 and 54 was used, the control value was 90% or more.

Test Example 4

The formulations of Compounds of Present Invention 3, 5 to 6, 8, 11, 15 to 16, 19 to 20, 22 to 23, 30 to 34, 39, 41 to 43 and 45 as produced in Formulation Example 5 were diluted with water, so as to have a concentration of the active ingredient of 500 ppm, to prepare each test drug solution.

On the other hand, a rice seedling (2 weeks after sowing, the second leaf stage) planted in a plastic cup was drenched at its foot with 5 ml of each test drug solution, and kept in a greenhouse at 25° C. for 7 days. Twenty third-fourth instar larvae of *Nilaparvata lugens* were released, and further kept in the greenhouse for 6 days, then the number of surviving *Nilaparvata lugens* parasitic on the rice leaves was examined, and the control value was calculated according to the following equation:

$$\text{Control value (\%)} = \{1-(Cb \times Tai)/(Cai \times Tb)\} \times 100$$

wherein the symbols represent as follows:

Cb: the number of insects in a non-treated section before treatment

Cai: the number of surviving parasitic insects in a non-treated section on observation Tb: the number of insects in a treated section before treatment Tai: the number of surviving parasitic insects in a treated section on observation wherein the non-treated section refers to a section where the test drug solution prepared by diluting the formulation produced as in Formulation Examples 3, 5 to 6, 8, 11, 15 to 16, 19 to 20, 22 to 23, 30 to 34, 39, 41 to 43 and 45 but not containing the compound of the present invention with the same amount of water as in the treated-section was sprayed.

As a result, in the treated-section where the test drug solution containing Compound of Present Invention 5 was used, the controlling value was 90% or more.

Test Example 5

The formulation of the compound of the present invention as produced in Formulation Example 5 was diluted with water, so as to have a concentration of the active ingredient of 500 ppm, to prepare a test drug solution.

On the other hand, *Bemisia tabaci* adult is released on a tomato seedling (the third true leaf stage) planted in a polyethylene cup, and made to lay eggs for about 72 hours. The tomato seedling is kept in a greenhouse for 8 days, and when instar larvae hatch from the eggs, the above test drug solution is sprayed at a rate of 20 ml/cup, and the cup is kept in a greenhouse at 25° C. After 7 days, the number of surviving instar larvae on the tomato leaves is examined, and the controlling value is calculated according to the following equation:

$$\text{Control value (\%)} = \{1-(Cb \times Tai)/(Cai \times Tb)\} \times 100$$

wherein the symbols represent as follows:

Cb: the number of instar larvae in a non-treated section before treatment

Cai: the number of surviving instar larvae in a non-treated section on observation Tb: the number of instar larvae in a treated section before treatment Tai: the number of surviving instar larvae in a treated section on observation wherein the non-treated section refers to a section where the test drug solution prepared by diluting the formulation obtained as in Formulation Example 5 but not containing the compound of the present invention with the same amount of water as in the treated section was sprayed.

As a result, in the treated-section where the test drug solution of the compound of the present invention is used, an excellent controlling value is produced.

Test Example 6

The formulations of Compounds of Present Invention 1, 6 to 9, 11, 14 to 16, 19, 22 to 24, 30 to 32, 34 to 39, 41 to 43 and 45 to 46 as produced in Formulation Example 5 were diluted with water, so as to have a concentration of the active ingredient of 500 ppm, to prepare each test drug solution.

On the other hand, on cabbage at the third leaf stage planted in a polyethylene cup was sprayed, at a rate of 20 mL/cup, the test drug solution. After the drug solution was dried, the foliage part was cut off, and then placed in a 50 mL volume cup. Five second instar larvae of *Plutella xylostella* were released into the cup, and the cup was sealed with a lid. After the cup was kept at 25° C. for 5 days, the number of dead insects was counted. The death rate was calculated according to the following equation:

Death rate (%)=(Number of dead insects/Number of tested insects)×100

As a result, in the treated section where the test drug solution containing each of Compounds of Present Invention 1, 6 to 9, 11, 14 to 16, 19, 22 to 24, 30 to 32, 34 to 39, 41 to 43 and 45 to 46 was used, the death rate was 80% or more.

Test Example 7

The formulations of Compounds of Present Invention 1, 3, 7 to 9, 11, 15 to 17, 19 to 22, 24 to 26 and 30 to 31 produced in Formulation Example 5 were diluted with water, so as to have a concentration of the active ingredient of 500 ppm, to prepare a test spray solution.

On the other hand, an apple tree was planted in a plastic cup, and grown until the seventh-eighth true leaf was spread. To the apple tree was sprayed, at a rate of 20 mL/cup, the test drug solution. After the drug solution was dried, 60 first-instar larvae of *Adoxophyes orana fasciata* were released, and covered with a plastic cup the bottom of which was cut off and on which a filter paper was put, with the plastic cup cover placed upside-down. After 7 days, the number of dead insects was counted, and the death rate was calculated according to the following equation:

Death rate (%)=(Number of dead insects/Number of tested insects)×100

As a result, in the treated section where the test drug solution containing each of Compounds of Present Invention 1, 3, 7 to 9, 11, 15 to 17, 19 to 22, 24 to 26 and 30 to 31 was used, the death rate was 90% or more.

Test Example 8

The formulations of Compounds of Present Invention 1, 9, 15 to 16, 19, 22, 24, 31 to 32, 34, 41 and 45 to 46 as produced in Formulation Example 5 were diluted with water, so as to have a concentration of the active ingredient of 500 ppm, to prepare each test drug solution.

A filter paper having a diameter of 5.5 cm was spread on the bottom of a polyethylene cup having the same diameter and 0.7 ml of the test drug solution was added dropwise onto the filter paper, and 30 mg of sucrose was uniformly placed as bait. Into the polyethylene cup, 10 female imagoes of *Musca domestica* were released, and the cup was sealed with a lid. After 24 hours, the life and death of *Musca domestica* was examined, the number of dead insects was counted, and the death rate was calculated according to the following equation.

Death rate (%)=(Number of dead insects/Number of tested insects)×100

As a result, in the treated section where the test drug solution containing each of Compounds of Present Invention 1, 9, 15 to 16, 19, 22, 24, 31 to 32, 34, 41 and 45 to 46 was used, the death rate was 100%.

Test Example 9

The formulations of Compounds of Present Invention 9, 15 to 16, 19, 22, 30 to 32, 34, 41 and 45 to 46 as produced in Formulation Example 5 were diluted with water, so as to have a concentration of the active ingredient of 500 ppm, to prepare each test drug solution.

A filter paper having a diameter of 5.5 cm was spread on the bottom of a polyethylene cup having the same diameter and 0.7 ml of the test drug solution was added dropwise onto the filter paper, and 30 mg of sucrose was uniformly placed as bait. Into the polyethylene cup, 2 male imagoes of *Blattella germanica* were released, and the cup was sealed with a lid. After 6 days, the life and death of *Blattella germanica* was examined, the number of dead insects was counted, and the death rate was calculated according to the following equation.

Death rate (%)=(Number of dead insects/Number of tested insects)×100

As a result, in the treated section where the test drug solution containing each of Compounds of Present Invention 9, 15 to 16, 19, 22, 30 to 32, 34, 41 and 45 to 46 was used, the death rate was 100%.

Test Example 10

The formulations of Compounds of Present Invention 1, 4, 6 to 12, 14 to 16, 19, 22 to 24, 30 to 32, 34, 36 to 39, 41 to 43 and 45 to 46 as produced in Formulation Example 5 were diluted with water, so as to have a concentration of the active ingredient of 500 ppm, to prepare each test drug solution.

0.7 ml of the test drug solution was added to 100 ml of ion-exchanged water (active ingredient concentration: 3.5 ppm) Twenty last-instar larvae of *Culex pipiens pallens* were released into the solution. One day later, the life and death of the *Culex pipiens pallens* was examined, and the number of dead insects was counted to calculate the death rate.

Death rate (%)=(Number of dead insects/Number of tested insects)×100

As a result, in the treated section where the test drug solution containing each of Compounds of Present Invention 1, 4, 6 to 12, 14 to 16, 19, 22 to 24, 30 to 32, 34, 36 to 39, 41 to 43 and 45 to 46 was used, the death rate was 95% or more.

Test Example 11

Two milligrams of each of Compounds of Present Invention 8 to 9, 20, 22 and 31 to 32 was weighed out in a screw tube (Maruemu No. 5; 27×55 mm), and 0.2 mL of acetone was added thereto, and the screw tube was sealed with a cap to dissolve the compound. The screw tube was rotated and inverted to uniformly coat the drug solution onto the whole inner wall of the tube. After removing the cap, the solution was air-dried for about 2 hours, then unfed nymphal ticks, *Haemaphysalis longicornis* (5 ticks/group) were released, and the tube was sealed with the cap. After 2 days, the number of dead insects was counted, and the death rate was calculated according to the following equation:

Death rate (%)=100×(Number of dead insects/Number of tested insects)

As a result, in the treated section where the test drug solution containing each of Compounds of Present Invention 8 to 9, 20, 22 and 31 to 32 was used, the death rate was 100%.

Test Example 12

The formulations of Compounds of Present Invention 3, 7, 28, 32 to 34, 36 to 46, 48 to 49, 51 and 54 as produced in Formulation Example 1 were diluted with water, so as to have a concentration of the active ingredient of 500 ppm, to prepare each test drug solution.

On the other hand, on cucumber at the third leaf stage planted in a polyethylene cup was sprayed, at a rate of 30 mL/cup, the test drug solution. After the drug solution was dried, the second leaf was cut off, and then placed in a 200 mL volume cup. Ten second instar larvae of *Aulacophora femoralis* were released into the cup, and the cup was sealed with a lid. After the cup was kept at 25° C. for 5 days, the number of dead insects was counted. The death rate was calculated according to the following equation:

Death rate (%)=(Number of dead insects/Number of tested insects)×100

As a result, in the treated section where the test drug solution containing each of Compounds of Present Invention 3, 7, 28, 32 to 34, 36 to 46, 48 to 49, 51 and 54 was used, the death rate was each 80% or more.

Test Example 13

The formulation of the compound of the present invention as produced in Formulation Example 1 was diluted with water, so as to have a concentration of the active ingredient of 500 ppm, to prepare a test drug solution.

On the other hand, artificial feed for *Diabrotica virgifera virgifera* is prepared according to the procedures of Pleau, et al. (Entomologia Experimentalis et Applicata 105: 1-11, 2002), and 2 mL of the feed is put in each well of a 24-well microplate (manufactured by Becton Dickinson). The test drug solution described above is sprayed onto the artificial feed at a rate of 40 μL/well, and after the drug solution is dried, five first-instar *Diabrotica virgifera virgifera* were released per 1 well, and the well is sealed by being covered with parafilm (manufactured by Bemis Company, Inc.). The cup is kept at 25° C., and after 3 days from the treatment, the number of dead insects is counted. The death rate is calculated according to the following equation:

Death rate (%)=(Number of dead insects/Number of tested insects)×100

As a result, in the treated-section where the compound of the present invention is used, a control effect is recognized.

INDUSTRIAL APPLICABILITY

The compound of the present invention has a control effect on pests and is useful as an active ingredient of a pest control agent.

The invention claimed is:
1. A fused heterocyclic compound represented by formula (1) or an N-oxide thereof:

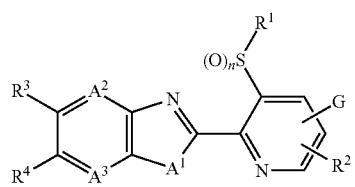

(1)

wherein
$A^1$ represents $NR^5$, an oxygen atom, or a sulfur atom,
$A^2$ represents a nitrogen atom or $CR^6$,
$A^3$ represents a nitrogen atom or $CR^7$, $R^1$ represents a C1 to C6 alkyl group optionally substituted with one or more atoms or groups selected from the group consisting of halogen atoms and cyclopropyl groups, wherein the cyclopropyl group is optionally substituted with one or more halogen atoms or one or more C1 to C3 alkyl groups, a C2 to C6 alkenyl group optionally substituted with one or more halogen atoms, a C2 to C6 alkynyl group optionally substituted with one or more halogen atoms, or a C3 to C6 cycloalkyl group optionally substituted with one or more atoms or groups selected from the group consisting of halogen atoms and C1 to C6 alkyl groups optionally substituted with one or more halogen atoms, $R^2$ represents a halogen atom or a hydrogen atom,
G represents a group represented by group G1, group G2, group G3, group G4, group G5, group G6 or group G7 of the following formulae:

(G1)

(G2)

(G3)

(G4)

(G5)

(G6)

(G7)

wherein
Q represents an oxygen atom or a sulfur atom,
p represents 0 or 1,
$R^{10}$ represents a C1 to C6 chain hydrocarbon group optionally substituted with one or more atoms or groups selected from group U, a phenyl group optionally substituted with one or more atoms or groups selected from group W, a hydrogen atom, a C1 to C6 chain hydrocarbon group substituted with one or more atoms or groups selected from group Z, a C3 to C9 alicyclic hydrocarbon group optionally substituted with one or more atoms or groups selected from group V, a 4-, 5- or 6-membered heterocyclic group optionally substituted with one or more atoms or groups selected from group W, $CO_2R^8$, $C(O)R^8$, or $C(O)NR^8R^9$, $R^{11}$ represents $R^{25}$, $R^{26}$, $OR^{27}$, $OR^{28}$, $SR^{29}$, $NR^{30}R^{31}$ or $C(O)R^{32}$, wherein $R^{25}$ represents a C1 to C6 chain hydrocarbon group substituted with one or more atoms or groups selected from group Z, a C3 to C9 alicyclic hydrocarbon group optionally substituted with one or more atoms or groups selected from group V, or a 4-, 5- or 6-membered heterocyclic group optionally substituted with one or more atoms or groups selected from group W; $R^{26}$ represents a C1 to C6 chain hydrocarbon group optionally substituted with one or more atoms or groups selected from group U, a phenyl group optionally substituted with one or more atoms or groups selected from group W, or a hydrogen atom; $R^{27}$ represents a C1 to C6 chain hydrocarbon group substituted with one or more atoms or groups selected from group Z, a C3 to C9 alicyclic hydrocarbon group optionally substituted with one or more atoms or groups selected from group V, or a 4-, 5- or 6-membered heterocyclic group optionally substituted with one or more atoms or groups selected from group W; $R^{28}$ represents a C1 to C6 chain hydrocarbon group optionally substituted with one or more atoms or groups selected from group U, a phenyl group optionally substituted with one or more atoms or groups selected from group W, or a hydrogen atom; $R^{29}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 5- or 6-membered heterocyclic group optionally substituted with one or more atoms or groups selected from group W, or a hydrogen atom; $R^{30}$ and $R^{31}$ are the same or different and represent a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, $SO_2R^8$, $CO_2R^8$, $C(O)R^8$, or a hydrogen atom; and $R^{32}$ represents a C1 to C6 chain hydrocarbon group optionally substituted with one or more atoms or groups selected from group Y, $OR^8$, $NR^8R9$, or a hydrogen atom, when $R^{11}$ represents $R^{25}$, $OR^{27}$, $SR^{29}$, $NR^{30}R^{31}$, or $C(O)R^{32}$, $R^{10}$ represents a C1 to C6 chain hydrocarbon group optionally substituted with one or more atoms or groups selected from group U, a phenyl group optionally substituted with one or more atoms or groups selected from group W, a hydrogen atom, a C1 to C6 chain hydrocarbon group substituted with one or more atoms or groups selected from group Z, a C3 to C9 alicyclic hydrocarbon group optionally substituted with one or more atoms or groups selected from group V, a 4-, 5- or 6-membered heterocyclic group optionally substituted with one or more atoms or groups selected from group W, $CO_2R^8$, $C(O)R^8$, or $C(O)NR^8R^9$, when $R^{11}$ represents $R^{26}$ or $OR^{28}$, $R^{10}$ represents a C1 to C6 chain hydrocarbon group substituted with one or more atoms or groups selected from group Z, a C3 to C9 alicyclic hydrocarbon group optionally substituted with one or more atoms or groups selected from group V, a 4-, 5- or 6-membered heterocyclic group optionally substituted with one or more atoms or groups selected from group W, $CO_2R^8$, $C(O)R^8$, or $C(O)NR^8R^9$, $R^{12}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, a hydrogen atom, $SO_2R^8$, $CO_2R^8$, $C(O)R^8$, or $C(O)NR^8R^9$, $R^{13}$ represents $R^{33}$, wherein $R^{33}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, or a 4-, 5- or 6-membered heterocyclic group optionally substituted with one or more atoms or groups selected from group W, $OR^{34}$, wherein $R^{34}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, or a hydrogen atom, or $NR^{35}R^{36}$, wherein $R^{35}$ and $R^{36}$ are the same or different and represent a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, or a hydrogen atom, $R^{14}$ and $R^{15}$ are the same or different and represent a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, a hydrogen atom, $SO_2R^8$, $CO_2R^8$, $C(O)R^8$, or $C(O)NR^8R^9$, $R^{16}$ represents $R^{37}$, wherein $R^{37}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, or a hydrogen atom, C(O)R$^{38}$, wherein R$^{38}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, or a hydrogen atom, CO$_2$R$^{39}$, wherein R$^{39}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, or a hydrogen atom, C(O)SR$^{40}$, wherein R$^{40}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, or a 4-, 5- or 6-membered heterocyclic group optionally substituted with one or more atoms or groups selected from group W, C(O)NR$^{41}$R$^{42}$, wherein R$^{41}$ and R$^{42}$ are the same or different and represent a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally h substituted with one or more atoms or groups selected from group W, a 4-, 5- or 6-membered heterocyclic group optionally substituted with one or more atoms or groups selected from group W, or a hydrogen atom, SO$_2$R$^{43}$, wherein R$^{43}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, or a 4-, 5- or 6-membered heterocyclic group optionally substituted with one or more atoms or groups selected from group W, S(O)$_2$OR$^{44}$, wherein R$^{44}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, or a 4-, 5- or 6-membered heterocyclic group optionally substituted with one or more atoms or groups selected from group W, or S(O)$_2$NR$^{45}$R$^{46}$, wherein R$^{45}$ and R$^{46}$ are the same or different and represent a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, or a hydrogen atom, R$^{17}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, a hydrogen atom, SO$_2$R$^8$, CO$_2$R$^8$, C(O)R$^8$, or C(O)NR$^8$R$^9$, R$^{18}$ represents R$^{47}$, wherein R$^{47}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, or a hydrogen atom, C(Q)R$^{48}$, wherein R$^{48}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, or a hydrogen atom, C(Q)OR$^{49}$, wherein R$^{49}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, or a hydrogen atom, or C(Q)NR$^{50}$R$^{51}$, wherein R$^{50}$ and R$^{51}$ are the same or different and represent a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, or a hydrogen atom, R$^{19}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 5- or 6-membered heterocyclic group optionally substituted with one or more atoms or groups selected from group W, or a hydrogen atom, $R^{20}$ represents $R^{52}$, wherein $R^{52}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, or a hydrogen atom, $OR^{53}$, wherein $R^{53}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, or a 4-, 5- or 6-membered heterocyclic group optionally substituted with one or more atoms or groups selected from group W, or $NR^{54}R^{55}$, wherein $R^{54}$ and $R^{55}$ are the same or different and represent a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, or a hydrogen atom, $R^{21}$ and $R^{22}$ are the same or different and represent a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, or a 4-, 5- or 6-membered heterocyclic group optionally substituted with one or more atoms or groups selected from group W, $R^{23}$ represents a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, or a hydrogen atom, $R^{24}$ represents a C1 to C6 chain hydrocarbon group substituted with one or more atoms or groups selected from group Z, a C3 to C9 alicyclic hydrocarbon group optionally substituted with one or more atoms or groups selected from group V, or a 4-, 5- or 6-membered heterocyclic group optionally substituted with one or more atoms or groups selected from group W, $R^3$ and $R^4$ are the same or different and represent a C1 to C6 chain hydrocarbon group optionally substituted with one or more atoms or groups selected from group U, $OR^8$, $S(O)_mR^8$, a halogen atom, or a hydrogen atom, $R^5$ represents a C1 to C6 chain hydrocarbon group optionally substituted with one or more atoms or groups selected from group X, $CO_2R^8$, $C(O)R^8$, a C3 to C9 alicyclic hydrocarbon group optionally substituted with one or more atoms or groups selected from group V, or a hydrogen atom, $R^6$ and $R^7$ are the same or different and represent a C1 to C6 chain hydrocarbon group optionally substituted with one or more halogen atoms, $OR^8$, $S(O)_mR^8$, $NR^8R^9$, $CO_2R^8$, $C(O)R^8$, a cyano group, a nitro group, a halogen atom, or a hydrogen atom, $R^8$ and $R^9$ are the same or different and represent a C1 to C6 chain hydrocarbon group optionally substituted with one or more atoms or groups selected from group Y, a C3 to C9 alicyclic hydrocarbon group optionally substituted with one or more atoms or groups selected from group V, a phenyl group optionally substituted with one or more atoms or groups selected from group W, a 4-, 5- or 6-membered heterocyclic group optionally substituted with one or more atoms or groups selected from group W, or a hydrogen atom, and each m independently represents 0, 1, or 2, and n represents 0, 1, or 2, wherein when m is 1 or 2 in $S(O)_mR^8$, $R^8$ does not represent a hydrogen atom;

group U is selected from the group consisting of C1 to C6 alkoxy groups optionally substituted with one or more halogen atoms, C2 to C6 alkenyloxy groups optionally substituted with one or more halogen atoms, C2 to C6 alkynyloxy groups optionally substituted with one or more halogen atoms, C1 to C6 alkylsulfanyl groups optionally substituted with one or more halogen atoms, C1 to C6 alkylsulfinyl groups optionally substituted with one or more halogen atoms, C1 to C6 alkylsulfonyl groups optionally substituted with one or more halogen atoms, C2 to C6 alkylcarbonyl groups optionally substituted with one or more halogen atoms, C2 to C6 alkoxycarbonyl groups optionally substituted with one or more halogen atoms, C3 to C9 cycloalkyl groups optionally substituted with one or more halogen atoms or one or more C1 to C3 alkyl groups, cyano groups, hydroxy groups, and halogen atoms, group V is selected from the group consisting of C1 to C6 chain hydrocarbon groups optionally substituted with one or more halogen atoms, C1 to C6 alkoxy groups optionally substituted with one or more halogen atoms, C2 to C6 alkenyloxy groups optionally substituted with one or more halogen atoms, C2 to C6 alkynyloxy groups optionally substituted with one or more halogen atoms, and halogen atoms, group W is selected from the group consisting of C1 to C6 chain hydrocarbon groups optionally substituted with one or more halogen atoms, C1 to C6 alkoxy groups optionally substituted with one or more halogen atoms, C1 to C6 alkylsulfanyl groups optionally substituted with one or more halogen atoms, C1 to C6 alkylsulfinyl groups optionally substituted with one or more halogen atoms, C1 to C6 alkylsulfonyl groups optionally substituted with one or more halogen atoms, C1 to C6 alkylamino groups optionally substituted with one or more halogen atoms, C2 to C8 dialkylamino groups optionally substituted with one or more halogen atoms, C2 to C6 alkylcarbonyl groups optionally substituted with one or more halogen atoms, C2 to C6 alkoxycarbonyl groups optionally substituted with one or more halogen atoms, halogen atoms, cyano groups, and nitro groups, group X is selected from the group consisting of C3 to C9 cycloalkyl groups optionally substituted with one or more halogen atoms, C1 to C6 alkoxy groups optionally substituted with one or more halogen atoms, C2 to C6 alkenyloxy groups optionally substituted with one or more halogen atoms, C2 to C6 alkynyloxy groups optionally substituted with one or more halogen atoms, C1 to C6 alkylsulfanyl groups optionally substituted with one or more halogen atoms, C1 to C6 alkylsulfinyl groups optionally substituted with one or more halogen atoms, C1 to C6 alkylsulfonyl groups optionally substituted with one or more halogen atoms, C2 to C6 alkylcarbonyl groups optionally substituted with one or more halogen atoms, C2 to C6 alkoxycarbonyl groups optionally substituted with one or more halogen atoms, hydroxy groups, halogen atoms, and cyano groups, group Y is selected from the group consisting of C3 to C9 alicyclic hydrocarbon groups optionally substituted with one or more atoms or groups selected from group V, C1 to C6 alkoxy groups optionally substituted with one or more halogen atoms, C2 to C6 alkenyloxy groups optionally substituted with one or more halogen atoms, C2 to C6 alkynyloxy groups optionally substituted with one or more halogen atoms, C1 to C6 alkylsulfanyl groups optionally substituted with one or more halogen atoms, C1 to C6 alkylsulfinyl groups optionally substituted with one or more halogen atoms, C1 to C6 alkylsulfonyl groups optionally substituted with one or more halogen atoms, C1 to C6 alkylaminosulfonyl groups optionally substituted with one or more halogen atoms, C2 to C8 dialkylaminosulfonyl groups optionally substituted with one or more halogen atoms, C1 to C6 alkylamino groups optionally substituted with one or more halogen atoms, C2 to C8 dialkylamino groups optionally substituted with one or more halogen atoms, C2 to C6 alkylcarbonylamino groups optionally substituted with one or more halogen atoms, C2 to C6 alkoxycarbonylamino groups optionally substituted with one or more halogen atoms, C2 to C6 alkylcarbonyl groups optionally substituted with one or more halogen atoms, C2 to C6 alkoxycarbonyl groups optionally substituted with one or more halogen atoms, C2 to C6 alkylaminocarbonyl groups optionally substituted with one or more halogen atoms, C3 to C10 dialkylaminocarbonyl groups optionally substituted with one or more halogen atoms, cyano groups, hydroxy groups, and halogen atoms, and group Z is selected from the group consisting of phenyl groups optionally substituted with one or more atoms or groups selected from group W, 4-, 5- or 6-membered heterocyclic groups optionally substituted with one or more atoms or groups selected from group W, C1 to C6 alkylamino groups optionally substituted with one or more halogen atoms, C2 to C8 dialkylamino groups optionally substituted with one or more halogen atoms, C2 to C6 alkylcarbonylamino groups optionally substituted with one or more halogen atoms, C2 to C6 alkoxycarbonylamino groups optionally substituted with one or more halogen atoms, C2 to C6 alkylaminocarbonyl groups optionally substituted with one or more halogen atoms, and C3 to C10 dialkylaminocarbonyl groups optionally substituted with one or more halogen atoms.

2. The fused heterocyclic compound according to claim 1, wherein $A^1$ is $NR^5$.

3. The fused heterocyclic compound according to claim 1, wherein $A^1$ is an oxygen atom.

4. The fused heterocyclic compound according to claim 1, wherein $A^1$ is a sulfur atom.

5. The fused heterocyclic compound according to claim 1, wherein $A^2$ is $CR^6$, and $A^3$ is a nitrogen atom.

6. The fused heterocyclic compound according to claim 1, wherein $A^2$ is $CR^6$, and $A^3$ is $CR^7$.

7. The fused heterocyclic compound according to claim 1, wherein G is group G1.

8. The fused heterocyclic compound according to claim 1, wherein G is group G2.

9. The fused heterocyclic compound according to claim 1, wherein G is group G3.

10. The fused heterocyclic compound according to claim 1, wherein G is group G4.

11. The fused heterocyclic compound according to claim 1, wherein G is group G5.

12. The fused heterocyclic compound according to claim 1, wherein G is group G6.

13. The fused heterocyclic compound according to claim 1, wherein G is group G7.

14. The fused heterocyclic compound according to claim 1, wherein G is group G1, and $R^{11}$ is $R^{25}$, $OR^{27}$, $SR^{29}$, $NR^{30}R^{31}$, or $C(O)R^{32}$.

15. The fused heterocyclic compound according to claim 1, wherein G is group G1, and $R^{11}$ is $R^{26}$ or $OR^{28}$.

16. The fused heterocyclic compound according to claim 1 represented by formula (1A), or an N-oxide thereof:

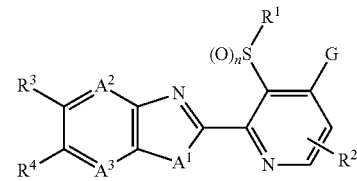

(1A)

wherein symbols represent the same meaning as in the formula (1).

17. The fused heterocyclic compound according to claim 1 represented by formula (1B), or an N-oxide thereof:

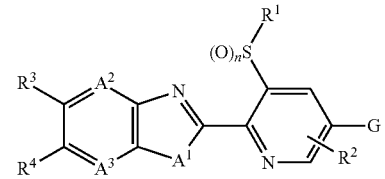

(1B)

wherein symbols represent the same meaning as in the formula (1).

18. The fused heterocyclic compound according to claim 1 represented by formula (1C), or an N-oxide thereof:

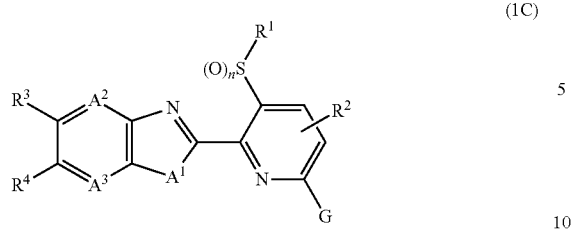
(1C)
wherein symbols represent the same meaning as in the formula (1).
19. A pest control agent comprising the fused heterocyclic compound according to claim 1, and an inert carrier.
20. A method for controlling pests comprising applying an effective amount of the fused heterocyclic compound according to claim 1 to a pest or a pest-infested area.
* * * * *